United States Patent
Deng et al.

(10) Patent No.: US 12,012,396 B2
(45) Date of Patent: *Jun. 18, 2024

(54) HDAC INHIBITOR SOLID STATE FORMS

(71) Applicant: Viracta Subsidiary, Inc., Cardiff, CA (US)

(72) Inventors: Xiaohu Deng, San Diego, CA (US); Wanping Mai, San Diego, CA (US); Robert C. McRae, Solana Beach, CA (US); Biljana Nadjsombati, Irvine, CA (US)

(73) Assignee: Viracta Subsidiary, Inc., Cardiff (CA)

( * ) Notice: Subject to any disclaimer, the term of this patent is extended or adjusted under 35 U.S.C. 154(b) by 0 days.

This patent is subject to a terminal disclaimer.

(21) Appl. No.: 18/364,074

(22) Filed: Aug. 2, 2023

(65) Prior Publication Data

US 2024/0166628 A1 May 23, 2024

Related U.S. Application Data

(63) Continuation of application No. 18/080,570, filed on Dec. 13, 2022, now Pat. No. 11,760,748, which is a continuation of application No. PCT/US2021/057106, filed on Oct. 28, 2021.

(60) Provisional application No. 63/106,811, filed on Oct. 28, 2020.

(51) Int. Cl.
*C07D 401/14* (2006.01)
*A61K 31/506* (2006.01)
*A61K 31/522* (2006.01)

(52) U.S. Cl.
CPC .......... *C07D 401/14* (2013.01); *A61K 31/506* (2013.01); *A61K 31/522* (2013.01); *C07B 2200/13* (2013.01)

(58) Field of Classification Search
None
See application file for complete search history.

(56) References Cited

U.S. PATENT DOCUMENTS

| 11,760,748 B2 | 9/2023 | Deng et al. |
| 11,780,822 B2 | 10/2023 | Deng et al. |
| 2010/0152155 A1 | 6/2010 | Moffat et al. |
| 2019/0091221 A1 | 3/2019 | Berenson et al. |
| 2019/0216818 A1 | 7/2019 | Woody |
| 2019/0290646 A1 | 9/2019 | Woody et al. |
| 2023/0023953 A1 | 1/2023 | Deng et al. |
| 2023/0382888 A1 | 11/2023 | Deng et al. |

FOREIGN PATENT DOCUMENTS

| TW | 202134232 A | 9/2021 |
| WO | WO-2006123121 A1 | 11/2006 |
| WO | WO-2011113013 A2 | 9/2011 |
| WO | WO-2018013962 A1 | 1/2018 |
| WO | WO-2018013975 A1 | 1/2018 |
| WO | WO-2019140296 A1 | 7/2019 |
| WO | WO-2019201123 A1 | 10/2019 |
| WO | WO-2020243326 A1 | 12/2020 |
| WO | WO-2021071809 A1 | 4/2021 |
| WO | WO-2021113694 A1 | 6/2021 |
| WO | WO-2022094122 A1 | 5/2022 |
| WO | WO-2023003972 A1 | 1/2023 |

OTHER PUBLICATIONS

Banerji, U. et al., "A Phase I Pharmacokinetic and Pharmacodynamic Study of CHR-3996, an Oral Class I Selective Histone Deacetylase Inhibitor in Refractory Solid Tumors", Clin Cancer Res, 2012, vol. 18, No. 9, pp. 2687-2694.
Huang et al.: Separation and Purification of β-Carotene from Chlorophyll Factory Residues. Chemical Engineering & Technology 31(6):922-927. DOI:10.1002/ceat.200800039 (2008).
Moffat, et al. Discovery of 2-(6-{[(6-fluoroquinolin-2-yl)methyl]amino}bicyclo[3.1.0]hex-3-yl)-N-hydroxypyrimidine-5-carboxamide (CHR-3996), a class I selective orally active histone deacetylase inhibitor.J Med Chem. Dec. 23, 2010;53(24):8663-78. Epub Nov. 16, 2010.
Moffat, et al. Supporting Information: Discovery of 2-(6-([(6-fluoroquinolin-2-yl)methyl]amino)bicyclo[3.1.0]hex-3-yl)-N-hydroxypyrimidine-5-carboxamide (CHR-3996), a class I selective orally active histone deacetylase inhibitor. Nov. 2010. Retrieved from the internet: https://pubs.acs.org/doi/suppl/10.1021/jm101177s/suppl_file/jm101177s_si_001.pdf.
PCT/US2021/057106 International Search Report and Written Opinion dated Feb. 3, 2022.
U.S. Appl. No. 18/080,570 Non-Final Office Action dated May 10, 2023.
U.S. Appl. No. 18/080,570 Notice of Allowance dated Jul. 21, 2023.
Zhou et al. Inhibition of Histone Deacetylase Activity Aggravates Coxsackievirus B3-Induced Myocarditis by Promoting Viral Replication and Myocardial Apoptosis. Journal of Virology, Oct. 2015, vol. 89, No. 20. 10512-10523.

*Primary Examiner* — Joseph R Kosack
*Assistant Examiner* — Jed A Kucharczk
(74) *Attorney, Agent, or Firm* — Wilson Sonsini Goodrich & Rosati

(57) ABSTRACT

The present disclosure relates to the crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide and methods of making the same. The crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide is useful in preparation of pharmaceutical compositions and dosage forms for the treatment of cancer, immune disorders and inflammation.

18 Claims, 35 Drawing Sheets

FIG. 2

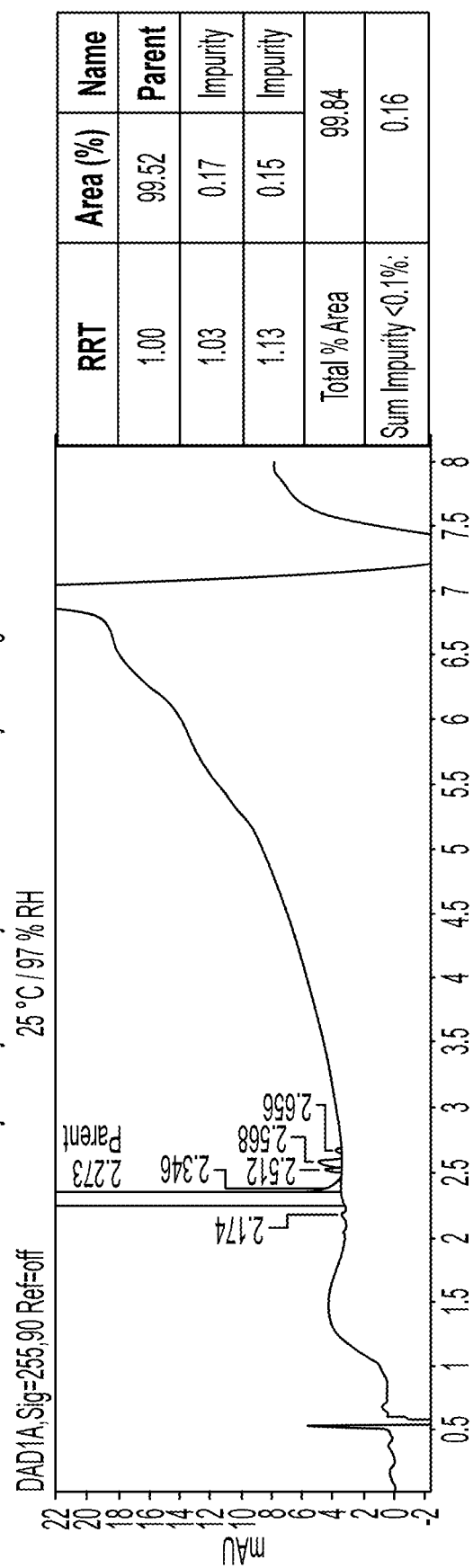
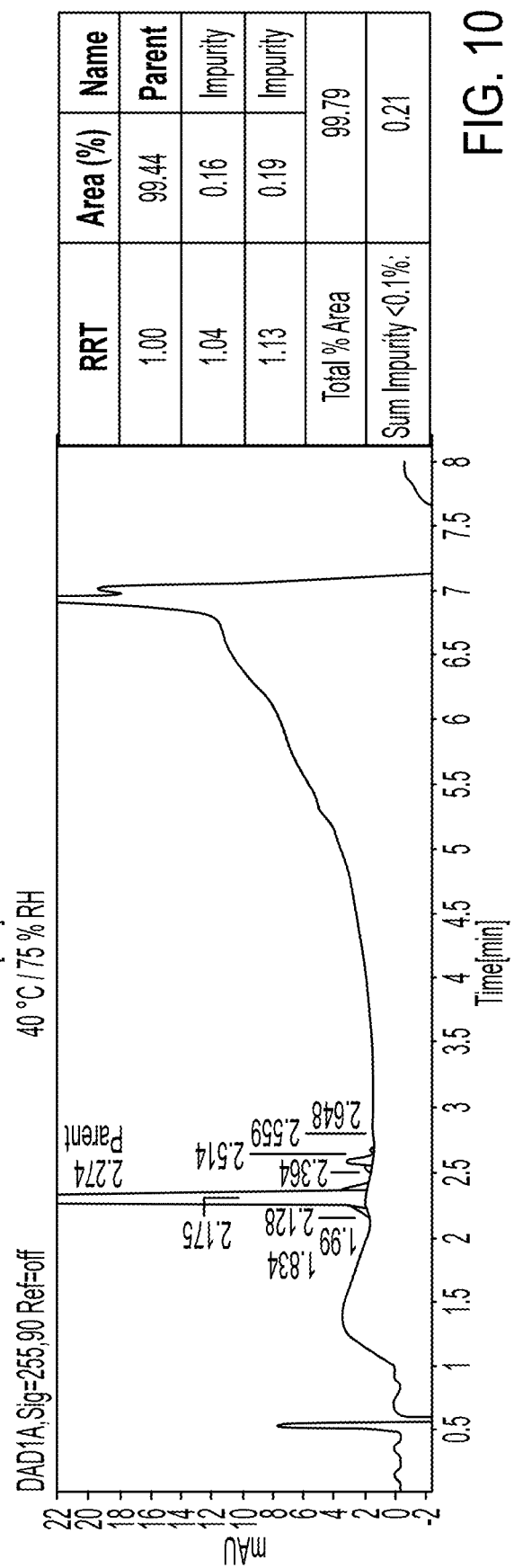
FIG. 10

HDAC INHIBITOR SOLID STATE FORMS

CROSS-REFERENCE TO RELATED APPLICATION

This application is a continuation of U.S. patent application Ser. No. 18/080,570, filed Dec. 13, 2022, which is a continuation of International Application No. PCT/US2021/057106, filed Oct. 28, 2021, which claims benefit of U.S. Patent Application No. 63/106,811 filed on Oct. 28, 2020, each of which is incorporated herein by reference in its entirety.

BACKGROUND OF THE INVENTION

The present disclosure relates to pharmaceutically acceptable salt forms of a histone deacetylase inhibitor compound and pharmaceutical compositions of said salt form, as well as the use of said compound in pharmaceutical compositions and medicine.

SUMMARY OF THE INVENTION

One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 3.7°±0.3. One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 3.7°±0.3, and 14.9°±0.3. One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 3.7°±0.3, 7.5°±0.3, and 14.9°±0.3.

One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate form 1 salt is characterized by at least one X-ray diffraction pattern reflection selected from a 2 theta value of 3.7°±0.3, 7.5°±0.3, 14.9°±0.3, 17.3°±0.3, 19.7°±0.3, 22.5°±0.3, 22.9°±0.3, or 30.1°±0.3. One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate form 1 salt is characterized by at least two X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, or 30.1°±0.3. One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate form 1 salt is characterized by at least three X-ray diffraction pattern reflections selected from a 2 theta value of 3.7°±0.3, 7.5°±0.3, 14.9°±0.3, 17.3°±0.3, 19.7°±0.3, 22.5°+0.3, 22.9°±0.3, or 30.1°±0.3. One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate form 1 salt is characterized by at least four X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, or 30.1°±0.3. One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate form 1 salt is characterized by at least five X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, or 30.1°±0.3.

One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 1.

One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 3.

One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by a single exothermic event with an onset temperature at about 222.1° C.±5.0 (433 J/g) or an exothermic peak at 225.8° C.±5.0.

One embodiment provides a crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the DSC pattern as shown in FIG. 3.

One embodiment provides an amorphous mesylate salt of N-hydroxy 2-{6-[(6-fluoro-quinolin-2-ylmethyl)-amino]-3-aza-bicyclo[3.1.0]hex-3-yl}pyrimidine-5-carboxamide.

One embodiment provides a solid form of N-hydroxy 2-{6-[(6-fluoro-quinolin-2-ylmethyl)-amino]-3-aza-bicyclo[3.1.0]hex-3-yl}pyrimidine-5-carboxamide wherein the amount of other crystalline or amorphous forms is 5% (w/w) or less.

One embodiment provides a solid form of N-hydroxy 2-{6-[(6-fluoro-quinolin-2-ylmethyl)-amino]-3-aza-bicyclo[3.1.0]hex-3-yl}pyrimidine-5-carboxamide, wherein the solid form is substantially free of impurities.

One embodiment provides a solid form of N-hydroxy 2-{6-[(6-fluoro-quinolin-2-ylmethyl)-amino]-3-aza-bicyclo[3.1.0]hex-3-yl}pyrimidine-5-carboxamide, wherein the amount of impurities is 3% or less.

One embodiment provides a pharmaceutical composition comprising any one of the compositions described herein, and one or more pharmaceutically acceptable excipients or carriers. One embodiment provides a pharmaceutical composition further comprising one or more additional active pharmaceutical ingredient (API). One embodiment provides a pharmaceutical composition, wherein the additional API is valganciclovir.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The features of the invention are set forth with particularity in the appended claims. A better understanding of the features of the present invention will be obtained by reference to the following detailed description that sets forth illustrative embodiments, in which the principles of the invention are utilized, and the accompanying drawings of which:

FIG. 2 shows the ¹H NMR spectra of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 10 shows the HPLC analysis of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide after storage under the indicated conditions.

DETAILED DESCRIPTION OF THE INVENTION

Figure 1:
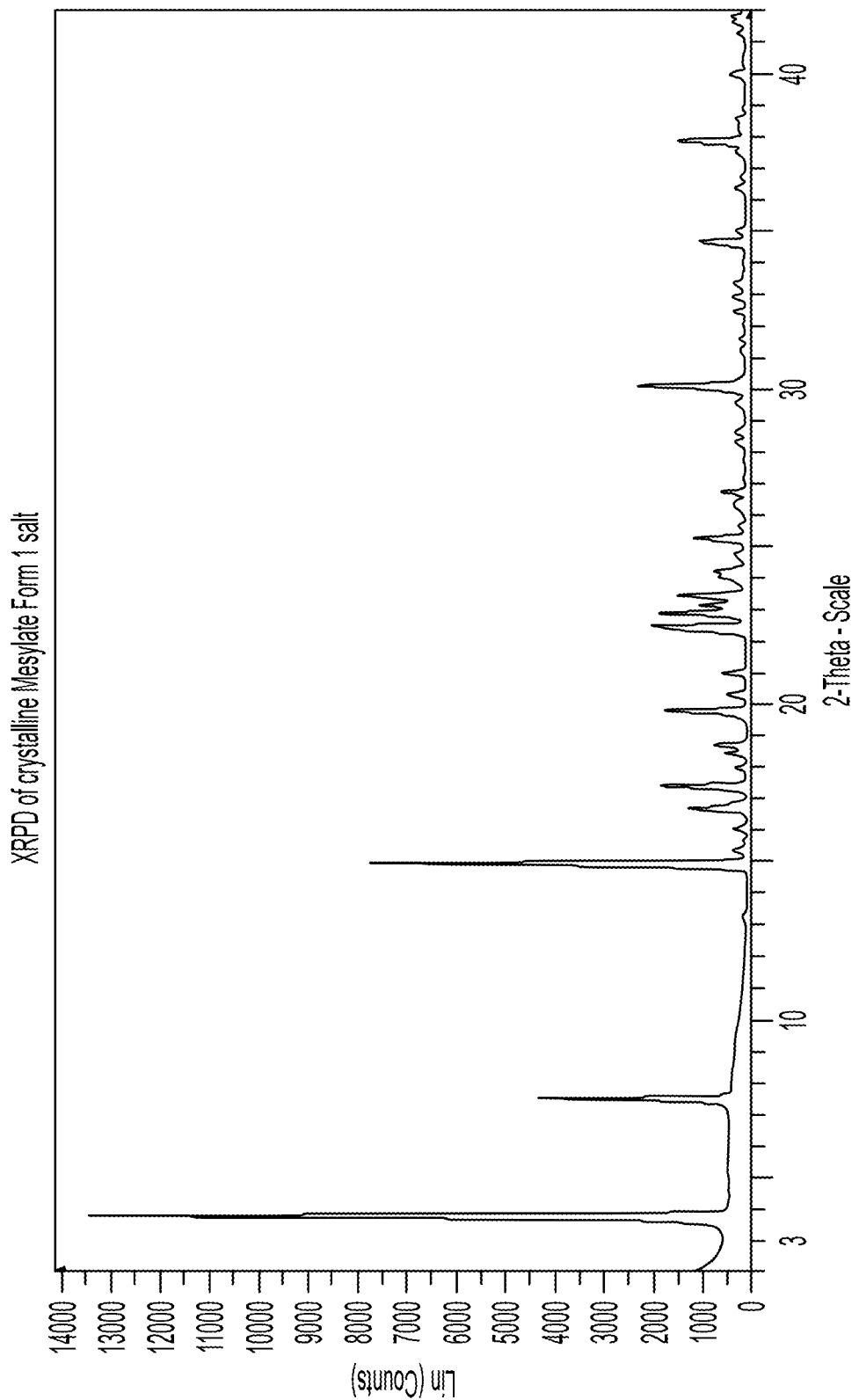
FIG. 1 shows the X-ray powder diffractogram of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Compounds that are histone deacetylase (HDAC) inhibitors have the potential to provide therapeutically effective pharmaceutical compositions that would be expected to have beneficial and improved pharmaceutical properties for the treatment of epigenetic related conditions or disorders such as cancer and other proliferative disorders.

Discussed herein is N-hydroxy-2-{6-[(6-fluoro-quinolin-2-ylmethyl)-amino]-3-aza-bicyclo[3.1.0]hex-3-yl}pyrimidine-5-carboxamide and referred to herein as Compound 1. Compound 1 is also known as nanatinostat, VRx-3996, or CHR-3996. It has been previously described in patents and patent applications, e.g. U.S. Pat. No. 7,932,246 and U.S. patent application Ser. No. 15/959,482, each of which is incorporated by reference in their entirety.

Compound 1

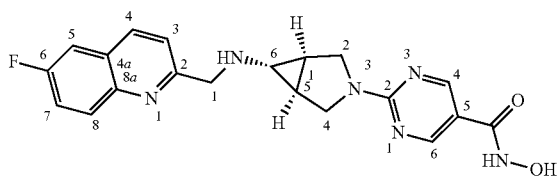

As a selective inhibitor of HDAC, Compound 1 is useful in the treatment of conditions in which HDAC has demonstrated a role in epigenetic regulation and pathology, such as cancer, immune disorders and inflammation. Two critical aspects in the development of Compound 1 as a useful therapy for such diseases and disorders are the discovery of practical methods for the preparation of Compound 1, and the discovery of pharmaceutically acceptable forms of Compound 1 and pharmaceutical compositions comprising said forms.

Definitions

As used herein, the term "crystalline," "highly crystalline," "crystalline solid form," or "highly crystalline solid form" refers to a solid form which is substantially free of any amorphous solid state form. In some embodiments, the crystalline solid form is a single solid state form, e.g. crystalline mesylate Form 1 salt. One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

As used herein, the term "partially crystalline" or "partially crystalline material" refers to an ad-mixture of two or more solid state forms. In some embodiments, partially crystalline refers to an ad-mixture of an amorphous solid form and at least one crystalline solid form. Partially crystalline material is not amorphous.

In some embodiments, crystallinity of a solid form is determined by X-Ray Powder Diffraction (XRPD). In some embodiments, crystallinity of a solid form is determined by solid state NMR.

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

The term "hydrate" and "solvate" are meant to describe crystalline Compound 1 forms that include an amount of water or solvent, as supported by data derived from differential scanning calorimetry (DSC) experiments, thermogravimetric analysis (TGA) experiments, X-ray diffraction experiments, and/or the procedure for generating the solid crystalline form. In some embodiments, a solvate crystalline form or hydrate crystalline form comprises at least 1.5%, 1.75%, 2.0%, 2.5%, 3.0%, 4.0%, 5.0%, 6.0%, 7.0%, 8.0%, 9.0%, 10.0%, 15.0%, or 20.0% of the total weight of the sample as water, solvent, or a combination thereof, as determined by TGA. In some embodiments, a solvate crystalline form or hydrate crystalline form exhibits at least one DSC endotherm onset before or within 30° C. of the boiling point of water or the solvent(s) used in the generation of the crystalline form. For example, a hydrate crystalline form may have a DSC endotherm onset at 108° C., with the endotherm peak positioned at 124° C.

Crystalline solid forms termed a "solvate," or "hydrate" are not meant to be limiting. For example, a solvate or hydrate can comprise a combination of water and solvent in the crystalline solid form.

The term "type," "form," and "pattern" are meant to be used interchangeably and are meant to refer to a particular crystalline material with properties described herein. For example, "crystalline hydrate Type A," "crystalline hydrate Form A," and "XRPD Pattern A" refer to the same crystalline matter.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range.

The term "substantially similar" as used herein means an analytical spectrum, such as XRPD pattern, DSC thermogram, or TGA thermogram, which resembles the reference spectrum to a great degree in both the peak locations and peak intensity.

Characterization of Compounds and Solid State Forms

In one embodiment, the present invention provides solid state forms of the mesylate salt of N-hydroxy 2-{6-[(6-fluoro-quinolin-2-ylmethyl)-amino]-3-aza-bicyclo[3.1.0]hex-3-yl}pyrimidine-5-carboxamide. In one embodiment, the crystalline forms are characterized by the interlattice plane intervals determined by a X-ray powder diffraction (XRPD) diffractogram. The diffractogram is typically represented by a diagram plotting the intensity of the peaks versus the location of the peaks, i.e., diffraction angle 2Θ (two-theta) in degrees. The characteristic peaks of a given compound can be selected according to the peak locations and their relative intensity to distinguish compounds and crystalline structures from others. Amorphous solid state forms were also characterized by XRPD. Amorphous solid state forms exhibit an absence of interlattice plane intervals.

Both crystalline and amorphous solid state forms were identified for the mesylate salt of N-hydroxy 2-{6-[(6-fluoro-quinolin-2-ylmethyl)-amino]-3-aza-bicyclo[3.1.0]hex-3-yl}pyrimidine-5-carboxamide. Amorphous solid state forms as described herein are specifically denoted as such.

Those skilled in the art recognize that the measurements of the XRD peak locations and/or intensity for a given crystalline form of the same compound will vary within a margin of error. The values of degree 2Θ allow appropriate error margins. Typically, the error margins are represented by "±". For example, the degree 2Θ of "8.716±0.3" denotes a range from 8.716+0.3, i.e., 9.016, to 8.716−0.3, i.e., 8.416. Depending on the sample preparation techniques, the calibration techniques applied to the instruments, human operational variation, and etc., those skilled in the art recognize that the margin of error for a XRD can be ±0.5; +0.4; +0.3; +0.2; +0.1; +0.05; or less. Additional details of the methods and equipment used for the XRD analysis are described in the Examples section.

In one embodiment, the crystalline forms are characterized by Differential Scanning Calorimetry (DSC) and Thermogravimetric Analysis (TGA). The DSC thermogram is typically expressed by a diagram plotting the normalized heat flow in units of Watts/gram ("W/g") versus the measured sample temperature in degree Celsius (C). The DSC thermogram is generally evaluated for extrapolated onset and end (outset) temperatures, peak temperature, and heat of fusion. The single maximum value of a DSV thermogram is often used as the characteristic peak to distinguish one crystalline form from another crystalline form. The TGA thermogram is typically expressed by a diagram plotting the weight loss percentage (%) versus the measured sample temperature in degree C. In the figures disclosed herein, DSC and TGA thermograms have been plotted sharing an X axis (temperature), but have distinct Y axes of weight % and heat flow corresponding respectively to TGA and DSC measurements.

Those skilled in the art recognize that the measurements of the DSC and TGA thermograms for a given crystalline form of the same compound will vary within a margin of error. The values of a single maximum value, expressed in degree C., allow appropriate error margins. Typically, the error margins are represented by "±". For example, the single maximum value of "53.1° C.±10.0" denotes a range from 53.1° C.+10.0, i.e., 63.1° C., to about 53.1° C.−10.0, i.e., 43.1° C. Depending on the sample preparation techniques, crystallization conditions, calibration techniques applied to the instruments, human operational variations, and etc., those skilled in the art recognize that the appropriate margin of error for a single maximum value can be ±10.0; ±7.5; ±5.0; ±2.5; ±2; ±1.5; ±1; ±0.5; or less for any of the powder diffraction reflections described herein.

Crystalline mesylate Form 1 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 7.5°±0.3.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 3.7°±0.3, and 14.9°±0.3.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 3.7°±0.3, 7.5°±0.3, and 14.9°±0.3.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 1 salt is characterized by at least one X-ray diffraction pattern reflection selected from a 2 theta value of 3.7°±0.3, 7.5°±0.3, 14.9°±0.3, 17.3° 0.3, 19.7°±0.3, 22.5°±0.3, 22.9°±0.3, and 30.1°±0.3. Another embodiment provides the crystalline form further characterized by at least two X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, and 30.1°±0.3.

Another embodiment provides the crystalline form further characterized by at least three X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, and 30.1°±0.3. Another embodiment provides the crystalline form further characterized by at least four X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, and 30.1°±0.3. Another embodiment provides the crystalline form further characterized by at least five X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, and 30.1°±0.3.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 1 salt is characterized by exhibits an X-ray powder diffraction reflection at a 2-theta value of 22.9°±0.3. In some embodiments, the crystalline form exhibits an X-ray powder diffraction reflection at a 2-theta value of 3.7°±0.3 and 16.7°±0.3. In some embodiments, the crystalline form exhibits an X-ray powder diffraction reflection at a 2-theta value of 7.5°±0.3 and 19.7°±0.3. In some embodiments, the crystalline form exhibits an X-ray powder diffraction reflection at a 2-theta value of 17.3°±0.3, 23.4°±0.3, and 25.3°±0.3. In some embodiments, the crystalline form exhibits an X-ray powder diffraction reflection at a 2-theta value of 14.9°±0.3, 22.5°±0.3, 23.1°±0.3, 24.0°±0.3, 24.2°±0.3, and 30.1°±0.3.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 1 salt is characterized by at least one X-ray diffraction pattern reflection selected from a 2 theta value of 3.7°±0.3, 7.5°±0.3, 14.9°±0.3, 16.7°±0.3, 17.3°±0.3, 19.7°±0.3, 22.5°±0.3, 22.9°±0.3, 23.1°±0.3, 23.4°±0.3, 24.0°±0.3, 24.2°±0.3, 25.3°±0.3, and 30.1°±0.3. In some embodiments, the crystalline mesylate Form 1 salt is characterized by at least two X-ray diffraction pattern reflections selected from a 2 theta value of 3.7°±0.3, 7.5°±0.3, 14.9°±0.3, 16.7°±0.3, 17.3° 0.3, 19.7°±0.3, 22.5°±0.3, 22.9°±0.3, 23.1°±0.3, 23.4°±0.3, 24.0°±0.3, 24.2°±0.3, 25.3°±0.3, and 30.1°±0.3. In some embodiments, the crystalline mesylate Form 1 salt is characterized by at least three X-ray diffraction pattern reflections selected from a 2 theta value of 3.7°±0.3, 7.5°±0.3, 14.9°±0.3, 16.7°±0.3, 17.3°±0.3, 19.7°±0.3, 22.5°±0.3, 22.9°±0.3, 23.1°±0.3, 23.4°±0.3, 24.0°±0.3, 24.2°±0.3, 25.3°±0.3, and 30.1°±0.3. In some embodiments, the crystalline mesylate Form 1 salt is characterized by at least four X-ray diffraction pattern reflections selected from a 2 theta value of 3.7°±0.3, 7.5°±0.3, 14.9°±0.3, 16.7°±0.3, 17.3°±0.3, 19.7°±0.3, 22.5°±0.3, 22.9°±0.3, 23.1°±0.3, 23.4°±0.3, 24.0°±0.3, 24.2°±0.3, 25.3°±0.3, and 30.1°±0.3. In some embodiments, the crystalline mesylate Form 1 salt is characterized by at least five X-ray diffraction pattern reflections selected from a 2 theta value of 3.7°±0.3, 7.5°±0.3, 14.9°±0.3, 16.7°±0.3, 17.3°±0.3, 19.7°±0.3, 22.5°±0.3, 22.9°±0.3, 23.1°±0.3, 23.4°±0.3, 24.0°±0.3, 24.2°±0.3, 25.3°±0.3, and 30.1° 0.3.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 1.

Figure 3:
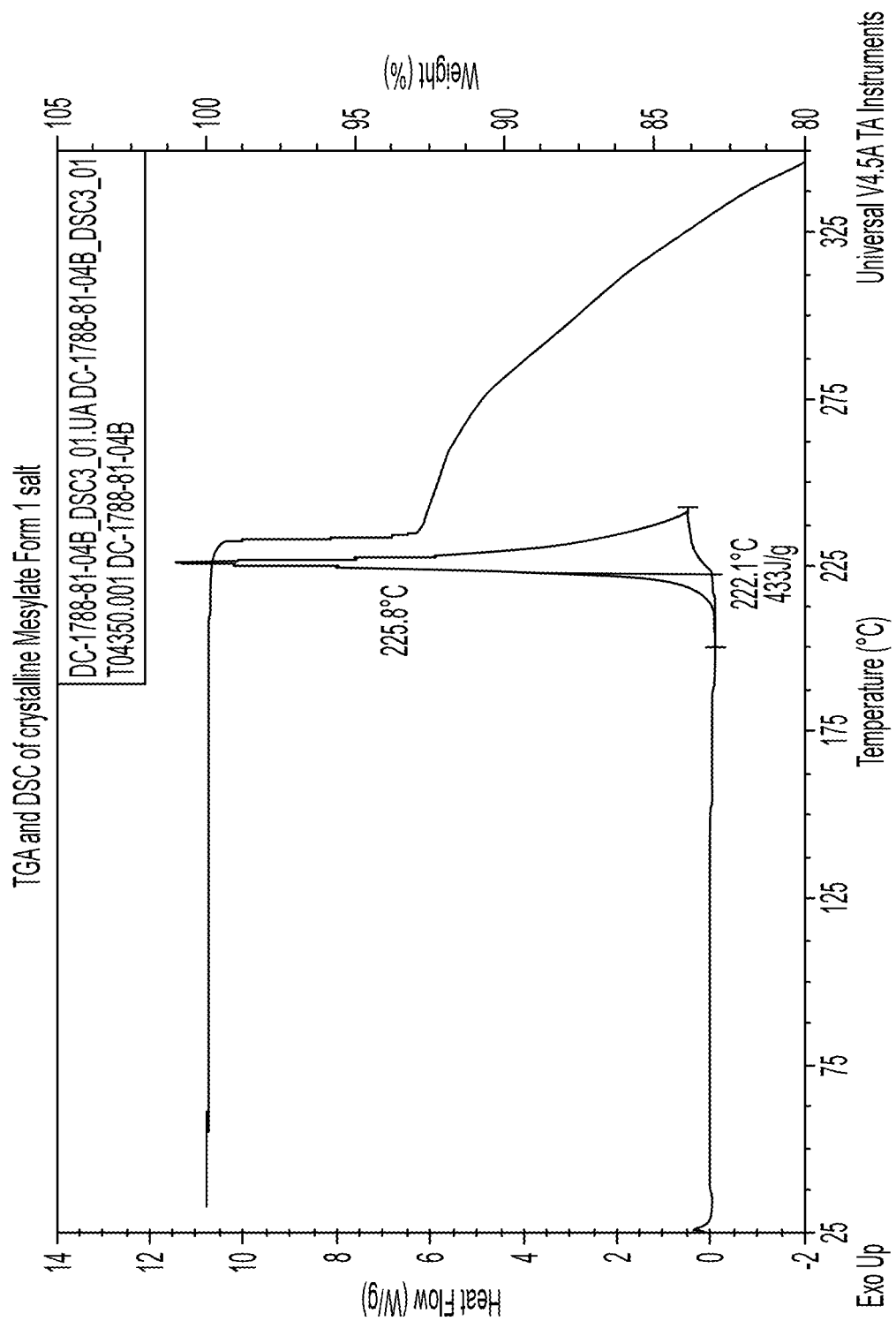
FIG. 3 shows the thermal gravimetric analysis pattern of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 3. In some embodiments, the crystalline form exhibits less than 0.5%±0.5 weight loss up to 225° C.±10.0 as determined by thermogravimetric analysis.

Provided herein is crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by a single exothermic event with an onset temperature at 222.1° C.+5.0 (433 J/g) and an exothermic peak at 225.8° C.±5.0 as shown in FIG. 3.

Provided herein is the crystalline mesylate Form 1 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.250% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Crystalline mesylate Form 2 salt of N-Hydroxy 2-{6-[(6-fluoro-quinolin-2-ylmethyl)-amino]-3-aza-bicyclo[3.1.0] hex-3-yl}pyrimidine-5-carboxamide Provided herein is crystalline mesylate Form 2 salt of N-hydroxy 2-{6-[(6-fluoro-quinolin-2-ylmethyl)-amino]-3-aza-bicyclo[3.1.0] hex-3-yl}pyrimidine-5-carboxamide.

Provided herein is crystalline mesylate Form 2 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 2 salt is characterized by exhibits an X-ray powder diffraction reflection at a 2-theta value of 14.6°±0.3. In some embodiments, the crystalline form exhibits an X-ray powder diffraction reflection at a 2-theta value of 24.3°±0.3 and 26.9°±0.3. In some embodiments, the crystalline form exhibits an X-ray powder diffraction reflection at a 2-theta value of 14.8°±0.3, 18.4°±0.3 and 19.5°±0.3. In some embodiments, the crystalline form exhibits an X-ray powder diffraction reflection at a 2-theta value of 16.4°±0.3, 20.5°±0.3, 21.9°±0.3, 23.5°±0.3, and 41.8°±0.3.

Provided herein is crystalline mesylate Form 2 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 2 salt is characterized by at least one X-ray diffraction pattern reflection selected from a 2 theta value of 14.6°±0.3, 14.8°±0.3, 16.4°±0.3, 18.4°±0.3, 19.5°±0.3, 20.5°±0.3, 21.9°±0.3, 23.5°±0.3, 24.3°±0.3, 26.9°±0.3, and 41.8°±0.3. In some embodiments, the crystalline mesylate Form 2 salt is characterized by at least two X-ray diffraction pattern reflections selected from a 2 theta value of 14.6°±0.3, 14.8°±0.3, 16.4°±0.3, 18.4°±0.3, 19.5°±0.3, 20.5°±0.3, 21.9°±0.3, 23.5°±0.3, 24.3°±0.3, 26.9°±0.3, and 41.8°±0.3. In some embodiments, the crystalline mesylate Form 2 salt is characterized by at least three X-ray diffraction pattern reflections selected from a 2 theta value of 14.6°±0.3, 14.8°±0.3, 16.4°±0.3, 18.4°±0.3, 19.5°±0.3, 20.5°±0.3, 21.9°±0.3, 23.5°±0.3, 24.3°±0.3, 26.9°±0.3, and 41.8°±0.3. In some embodiments, the crystalline mesylate Form 2 salt is characterized by at least four X-ray diffraction pattern reflections selected from a 2 theta value of 14.6°±0.3, 14.8°±0.3, 16.4°±0.3, 18.4°±0.3, 19.5°±0.3, 20.5°±0.3, 21.9°±0.3, 23.5°±0.3, 24.3°±0.3, 26.9°±0.3, and 41.8°±0.3. In some embodiments, the crystalline mesylate Form 2 salt is characterized by at least five X-ray diffraction pattern reflections selected from a 2 theta value of 14.6°±0.3, 14.8°±0.3, 16.4°±0.3, 18.4°±0.3, 19.5°±0.3, 20.5°±0.3, 21.9°±0.3, 23.5°±0.3, 24.3°±0.3, 26.9°±0.3, and 41.8°±0.3.

Figure 13:
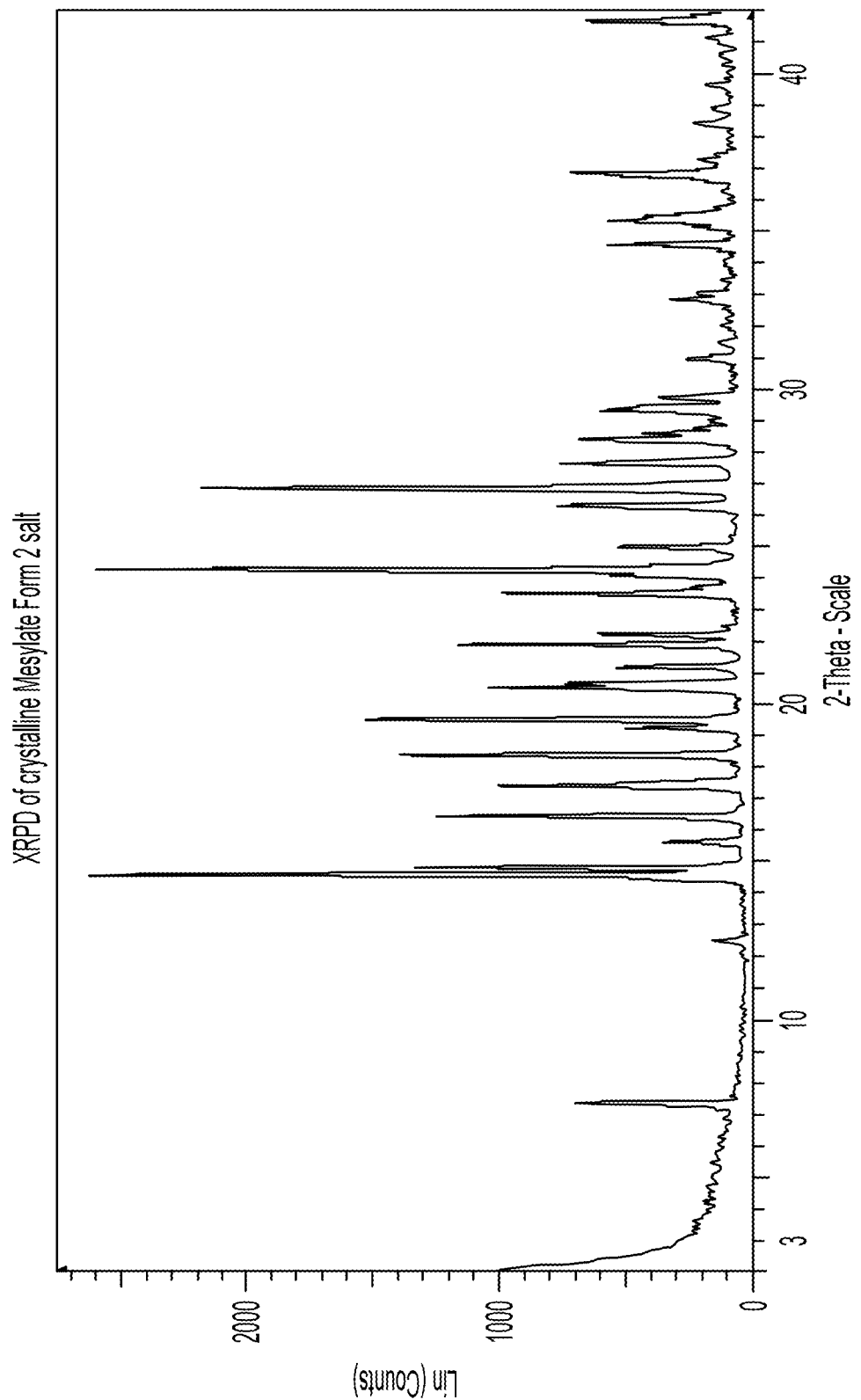
FIG. 13 shows the XRPD of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 2 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 13.

Figure 14:
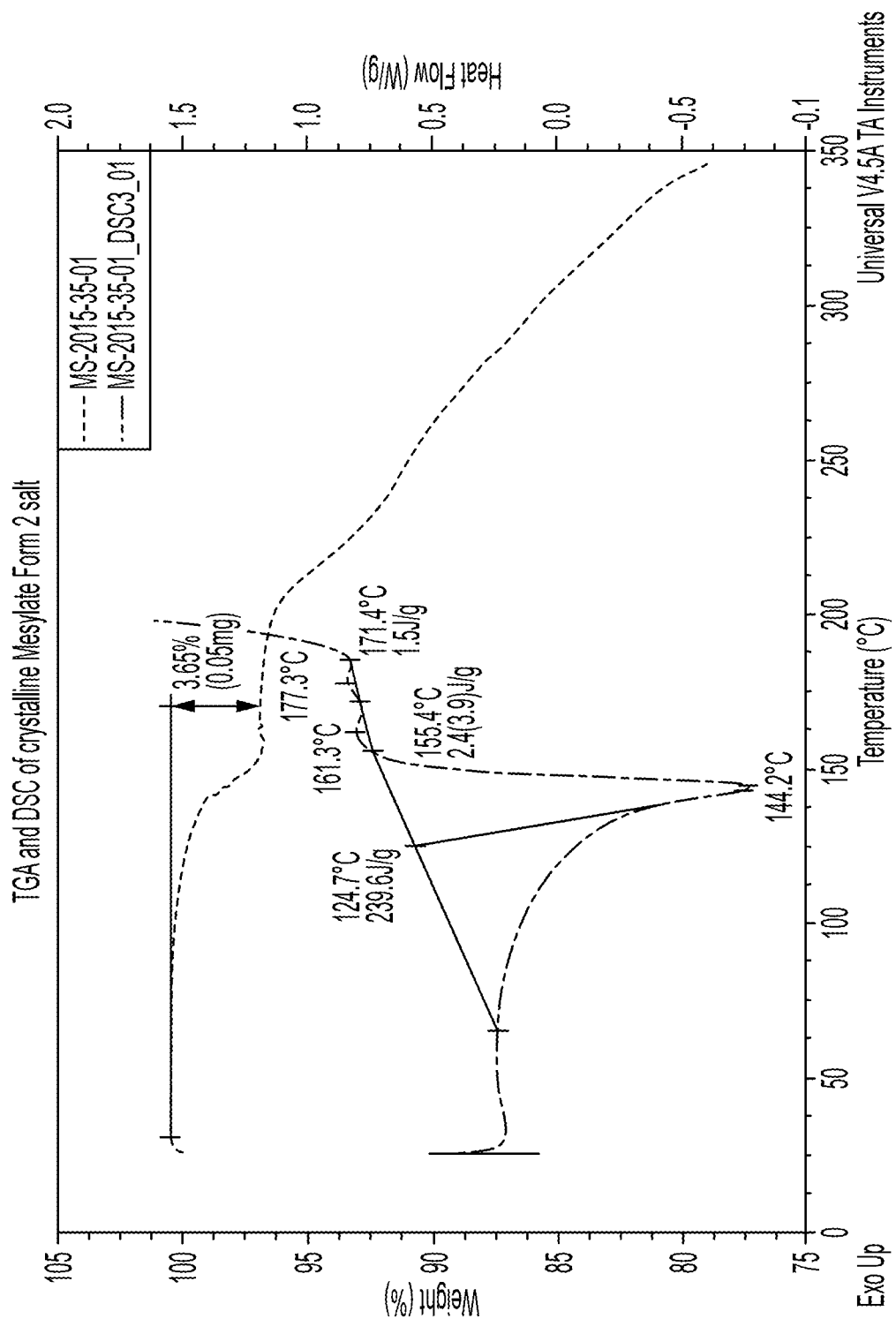
FIG. 14 shows the TGA and DSC of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 2 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 14. In some embodiments, the crystalline form exhibits less than 3.7%±0.5 weight loss up to 170° C.±10.0 as determined by thermogravimetric analysis.

Provided herein is crystalline mesylate Form 2 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by a single endothermic event with an onset temperature at 124.7° C.+5.0 (239.6 J/g) and an endothermic peak at 144.2° C.±5.0 as shown in FIG. 14.

Provided herein is the crystalline mesylate Form 2 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5%

Crystalline mesylate Form 3 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 3 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 3 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 3 salt is characterized by exhibits an X-ray powder diffraction reflection at a 2-theta value of 9.5°±0.3. In some embodiments, the crystalline form exhibits an X-ray powder diffraction reflection at a 2-theta value of 10.3°±0.3 and 19.4°±0.3. In some embodiments, the crystalline form exhibits an X-ray powder diffraction reflection at a 2-theta value of 14.8°±0.3 and 24.8°±0.3. In some embodiments, the crystalline form exhibits an X-ray powder diffraction reflection at a 2-theta value of 6.3°±0.3, 16.5°±0.3, 23.3°±0.3, and 27.2°±0.3.

Provided herein is crystalline mesylate Form 3 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 3 salt is characterized by at least one X-ray diffraction pattern reflection selected from a 2 theta value of 6.30° 0.3, 9.5°±0.3, 10.3°±0.3, 14.8°±0.3, 16.5°±0.3, 19.4°±0.3, 23.3° 0.3, 24.8°±0.3, and 27.2°±0.3. In some embodiments, the crystalline mesylate Form 3 salt is characterized by at least two X-ray diffraction pattern reflections selected from a 2 theta value of 6.3° 0.3, 9.5°±0.3, 10.3°±0.3, 14.8°±0.3, 16.5°±0.3, 19.4°±0.3, 23.3°±0.3, 24.8°±0.3, and 27.2°±0.3. In some embodiments, the crystalline mesylate Form 3 salt is characterized by at least three X-ray diffraction pattern reflections selected from a 2 theta value of 6.30 0.3, 9.5°±0.3, 10.3 0±03, 14.8°±0.3, 16.5°±0.3, 19.4°±0.3, 23.3°±03, 24.8°±0.3, and 27.2°±0.3. In some embodiments, the crystalline mesylate Form 3 salt is characterized by at least four X-ray diffraction pattern reflections selected from a 2 theta value of 6.30 0.3, 9.5°±0.3, 10.3°±0.3, 14.8°±0.3, 16.5°±0.3, 19.4° 00.3, 23.3° 0.3, 24.8° 0.3, and 27.2° 0.3. In some embodiments, the crystalline mesylate Form 3 salt is characterized by at least five X-ray diffraction pattern reflections selected from a 2 theta value of 6.3°0.3, 9.5°±0.3, 10.3°±0.3, 14.8°±0.3, 16.5°±0.3, 19.4° 0.3, 23.3° 0.3, 24.8°±0.3, and 27.2°±0.3.

Figure 17:
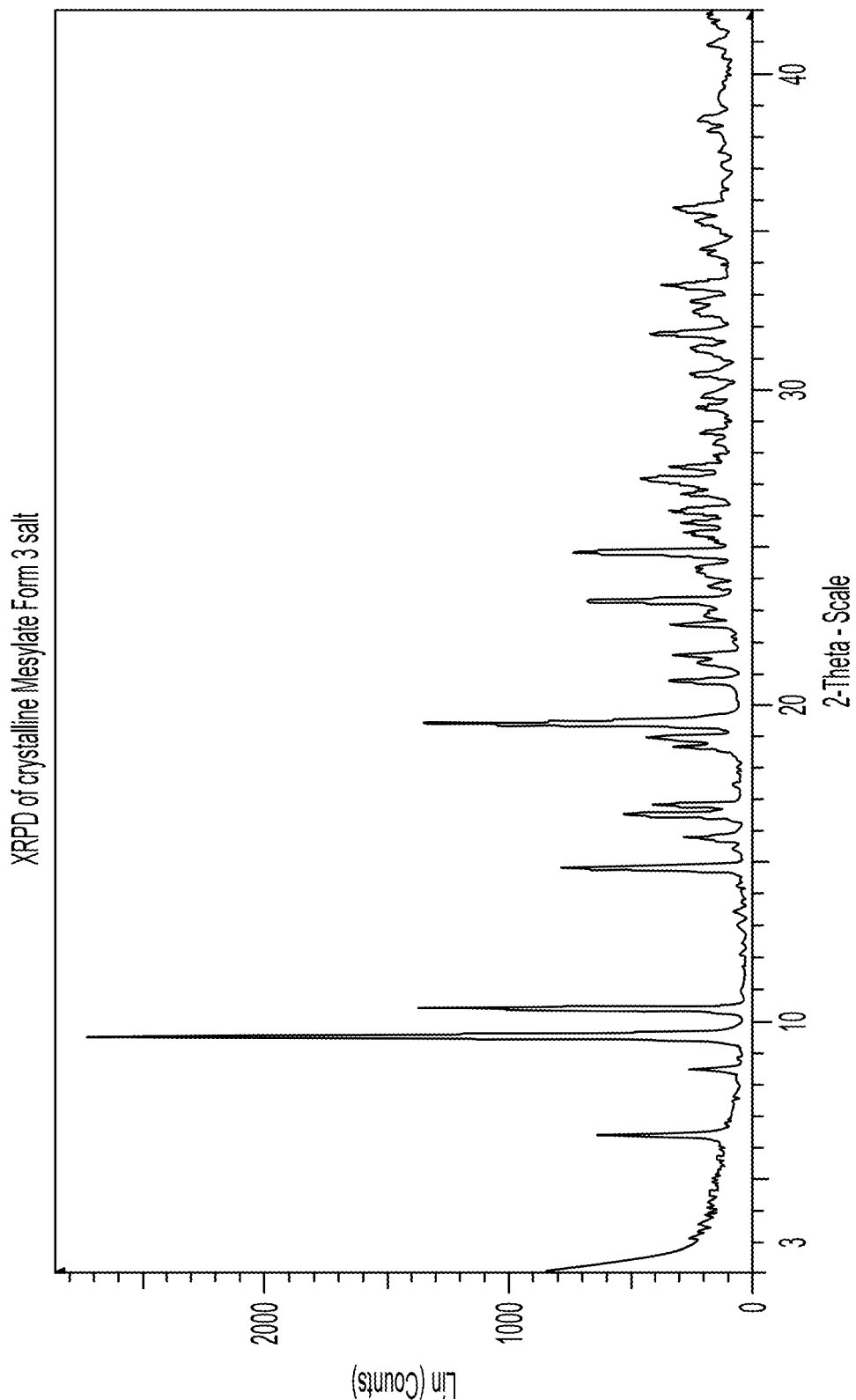
FIG. 17 shows the XRPD of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 3 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 17.

Figure 18:
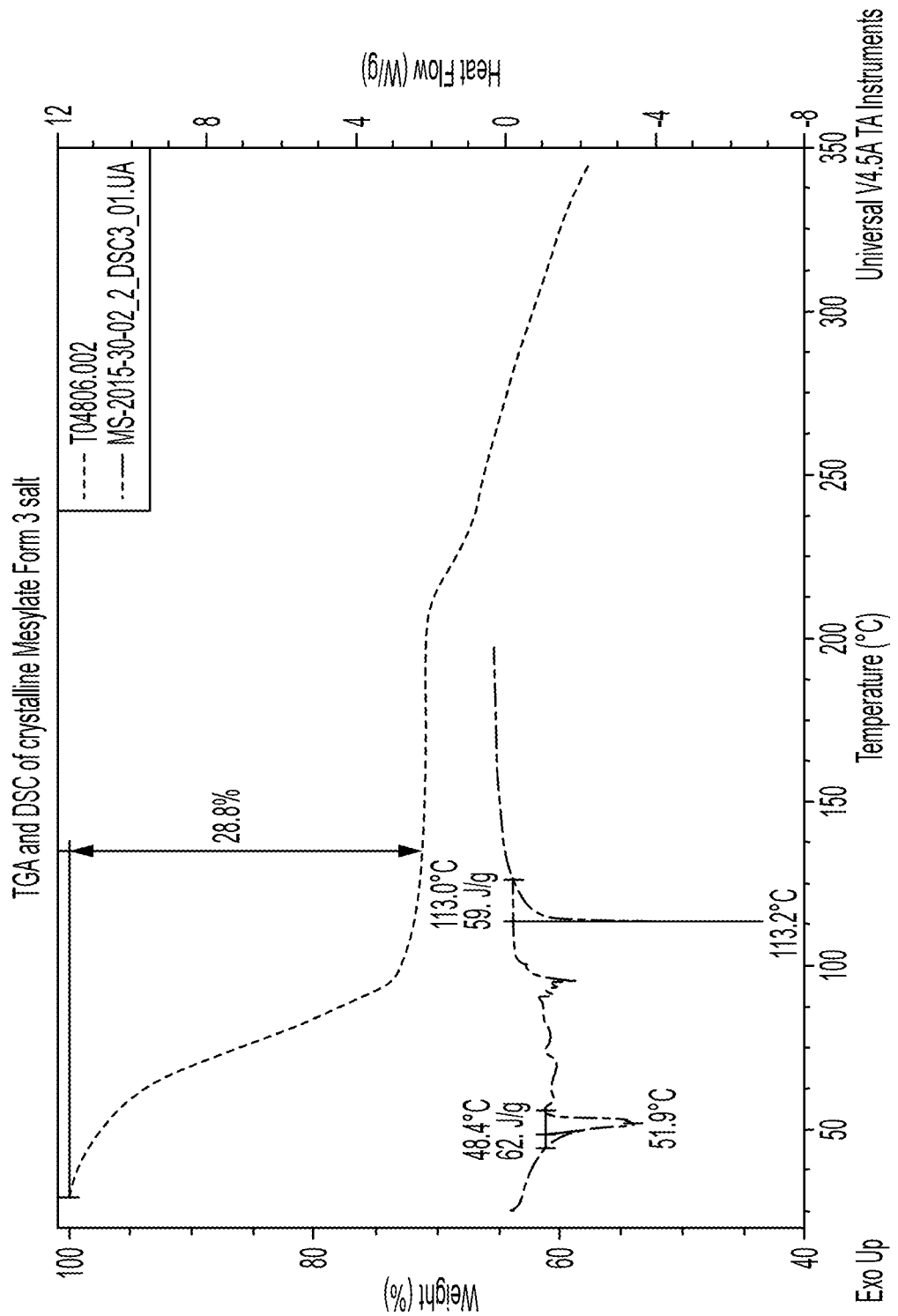
FIG. 18 shows the TGA and DSC of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 3 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 18. In some embodiments, the crystalline form exhibits less than 28.8%±0.5 weight loss up to 135° C.+10.0 as determined by thermogravimetric analysis.

Provided herein is crystalline mesylate Form 3 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by an endothermic event with an onset temperature at 48.2° C.±5.0 (62 J/g) and an endothermic peak at 51.9° C.±5.0; and an endothermic event with an onset temperature at 113.0° C.±5.0 (59 J/g) and an endothermic peak at 113.2° C.±5.0 as shown in FIG. 18.

Provided herein is the crystalline mesylate Form 3 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Crystalline mesylate Form 4 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 4 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 4 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 4 salt is characterized by exhibits an X-ray powder diffraction reflection at a 2-theta value of 3.5°±0.3. In some embodiments, the crystalline form exhibits an X-ray powder diffraction reflection at a 2-theta value of 10.3° 0.3, 17.2°±0.3, and 17.7°±0.3. In some embodiments, the crystalline form exhibits an X-ray powder diffraction reflection at a 2-theta value of 22.4°±0.3, 24.7°±0.3, and 26.4°±0.3.

Provided herein is crystalline mesylate Form 4 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 4 salt is characterized by at least one X-ray diffraction pattern reflection selected from a 2 theta value of 3.50° 0.3, 10.3° 0.3, 17.2°±0.3, 17.7°±0.3, 22.4°±0.3, 24.7°±0.3, and 26.4°±0.3. In some embodiments, the crystalline mesylate Form 4 salt is characterized by at least two X-ray diffraction pattern reflections selected from a 2 theta value of 3.5°±0.3, 10.3°±0.3, 17.2°±0.3, 17.7°±0.3, 22.4°±0.3, 24.7°±0.3, and 26.4°±0.3. In some embodiments, the crystalline mesylate Form 4 salt is characterized by at least three X-ray diffraction pattern reflections selected from a 2 theta value of 3.5°±0.3, 10.30 0.3, 17.2°±0.3, 17.7°±0.3, 22.4°±0.3, 24.7°±0.3, and 26.4°±0.3. In some embodiments, the crystalline mesylate Form 4 salt is characterized by at least four X-ray diffraction pattern reflections selected from a 2 theta value of 3.5°±0.3, 10.3°±0.3, 17.2°±0.3, 17.7°±0.3, 22.4°±0.3, 24.7°±0.3, and 26.4°±0.3. In some embodiments, the crystalline mesylate Form 4 salt is characterized by at least five X-ray diffraction pattern reflections selected from a 2 theta value of 3.5°±0.3, 10.30 0.3, 17.2°±0.3, 17.7°±0.3, 22.4°±0.3, 24.7°±0.3, and 26.4°±0.3.

Figure 21:
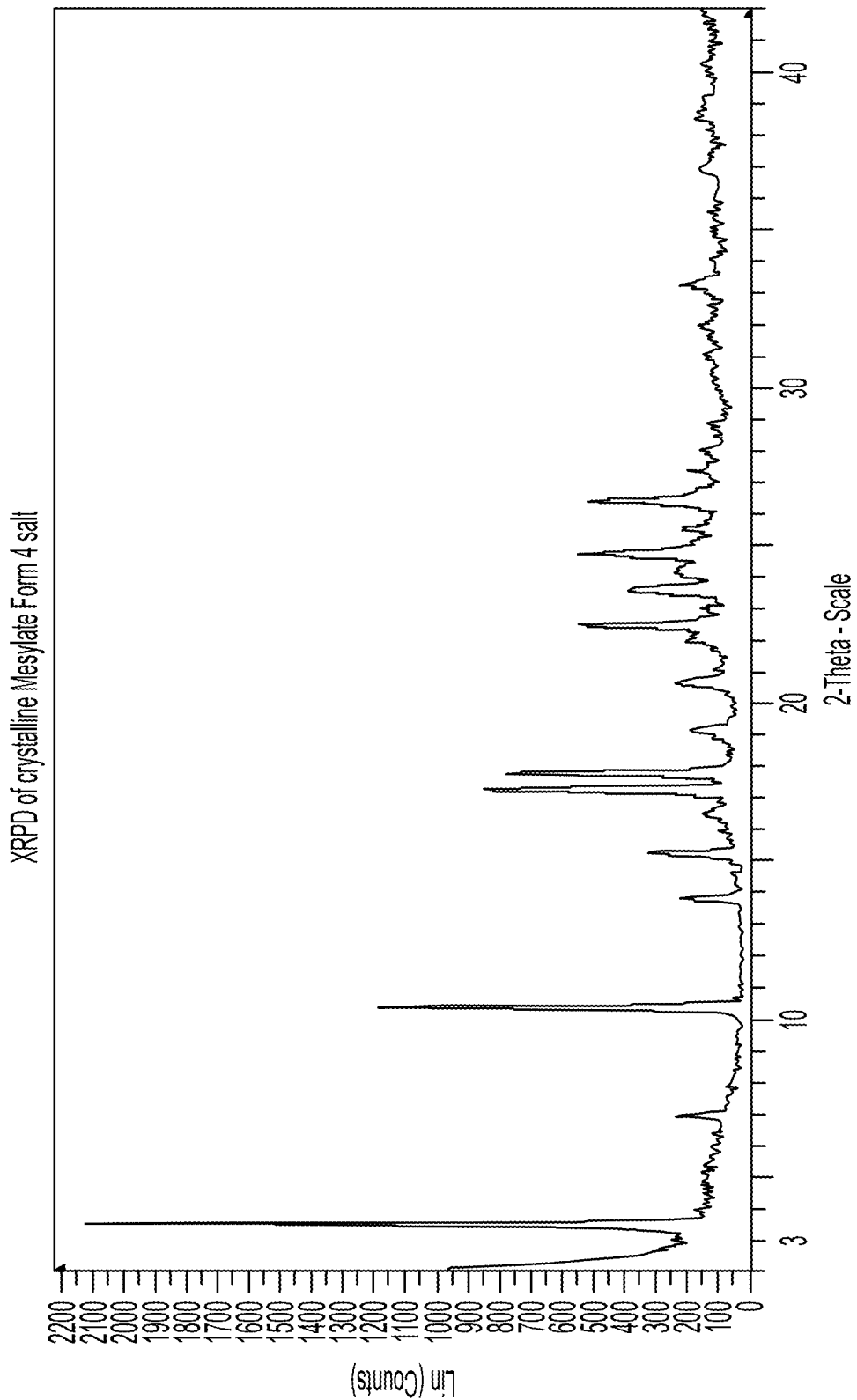
FIG. 21 shows the XRPD of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 4 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 21.

Figure 22:
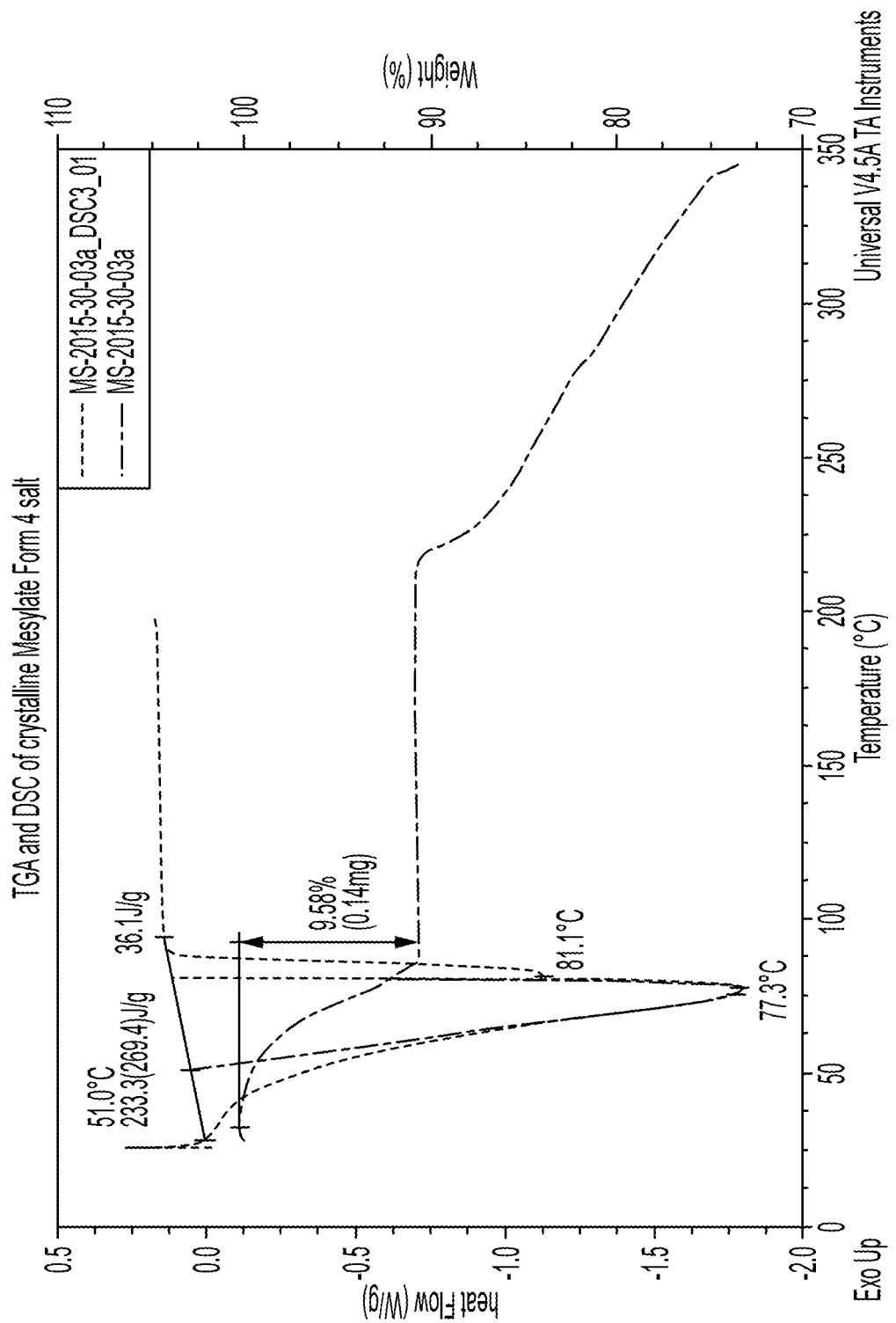
FIG. 22 shows the TGA and DSC of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 4 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 22. In some embodiments, the crystalline form exhibits less than 9.6%±0.5 weight loss up to 92° C.±10.0 as determined by thermogravimetric analysis.

Provided herein is crystalline mesylate Form 4 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by a single endothermic event with an onset temperature at 51.0° C.±5.0 (269 J/g) and an endothermic peak at 77.3° C.±5.0 as shown in FIG. 22.

Provided herein is the crystalline mesylate Form 4 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5%

(w/w), less than about 3% (w/w), less than about 1% (w/w), less than about 0.5% (w/w), or less than about 0.2% (w/w).

Crystalline mesylate Form 5 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 5 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 5 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 5 salt is characterized by exhibits an X-ray powder diffraction reflection at a 2-theta value of 20.7°±0.3. In some embodiments, the crystalline form exhibits an X-ray powder diffraction reflection at a 2-theta value of 15.7°±0.3, 16.8°±0.3 and 18.0°±0.3. In some embodiments, the crystalline form exhibits an X-ray powder diffraction reflection at a 2-theta value of 27.4°±0.3 and 34.6°±0.3. In some embodiments, the crystalline form exhibits an X-ray powder diffraction reflection at a 2-theta value of 21.5°±0.3, 24.3°±0.3, 33.9°±0.3, 36.7°±0.3, and 40.9°±0.3.

Provided herein is crystalline mesylate Form 5 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 5 salt is characterized by at least one X-ray diffraction pattern reflection selected from a 2 theta value of 15.7°±0.3, 16.8°±0.3, 18.0°±0.3, 20.7°±0.3, 21.5°±0.3, 24.3°±0.3, 27.4°±0.3, 33.9°±0.3, 34.6°±0.3, 36.7°±0.3, and 40.9°±0.3. In some embodiments, the crystalline mesylate Form 5 salt is characterized by at least two X-ray diffraction pattern reflections selected from a 2 theta value of 15.7°±0.3, 16.8°±0.3, 18.0°±0.3, 20.7°±0.3, 21.5°±0.3, 24.3°±0.3, 27.4°±0.3, 33.9°±0.3, 34.6°±0.3, 36.7°±0.3, and 40.9°±0.3. In some embodiments, the crystalline mesylate Form 5 salt is characterized by at least three X-ray diffraction pattern reflections selected from a 2 theta value of 15.7°±0.3, 16.8°±0.3, 18.0°±0.3, 20.7°±0.3, 21.5°±0.3, 24.3°±0.3, 27.4°±0.3, 33.9°±0.3, 34.6°±0.3, 36.7°±0.3, and 40.9°±0.3. In some embodiments, the crystalline mesylate Form 5 salt is characterized by at least four X-ray diffraction pattern reflections selected from a 2 theta value of 15.7°±0.3, 16.8°±0.3, 18.0°±0.3, 20.7°±0.3, 21.5°±0.3, 24.3°±0.3, 27.4°±0.3, 33.9°±0.3, 34.6°±0.3, 36.7°±0.3, and 40.9°±0.3. In some embodiments, the crystalline mesylate Form 5 salt is characterized by at least five X-ray diffraction pattern reflections selected from a 2 theta value of 15.7°±0.3, 16.8°±0.3, 18.0°±0.3, 20.7°±0.3, 21.5°±0.3, 24.3°±0.3, 27.4°±0.3, 33.9°±0.3, 34.6°±0.3, 36.7°±0.3, and 40.9°±0.3.

Figure 25:
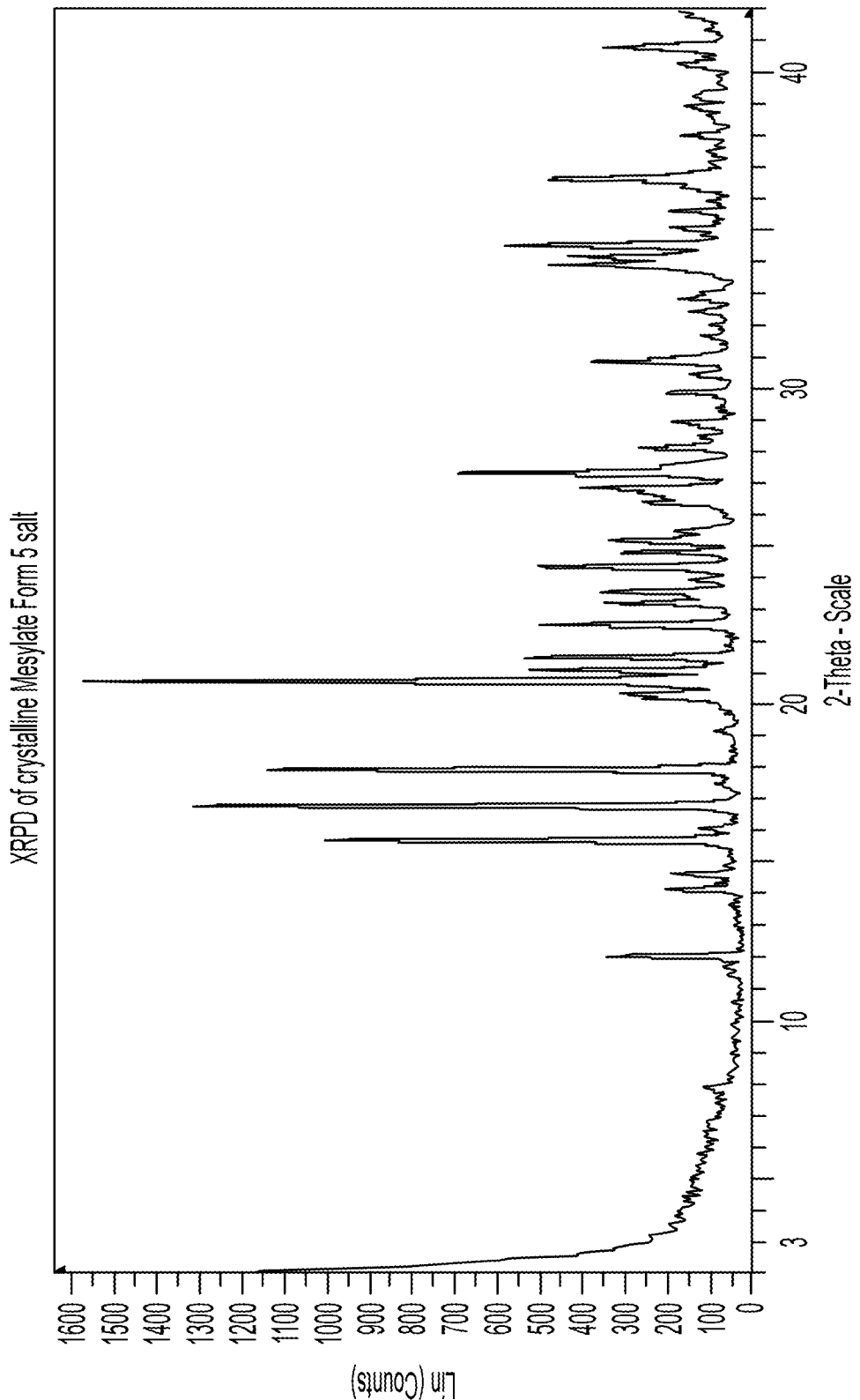
FIG. 25 shows the XRPD of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 5 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 25.

Figure 26:
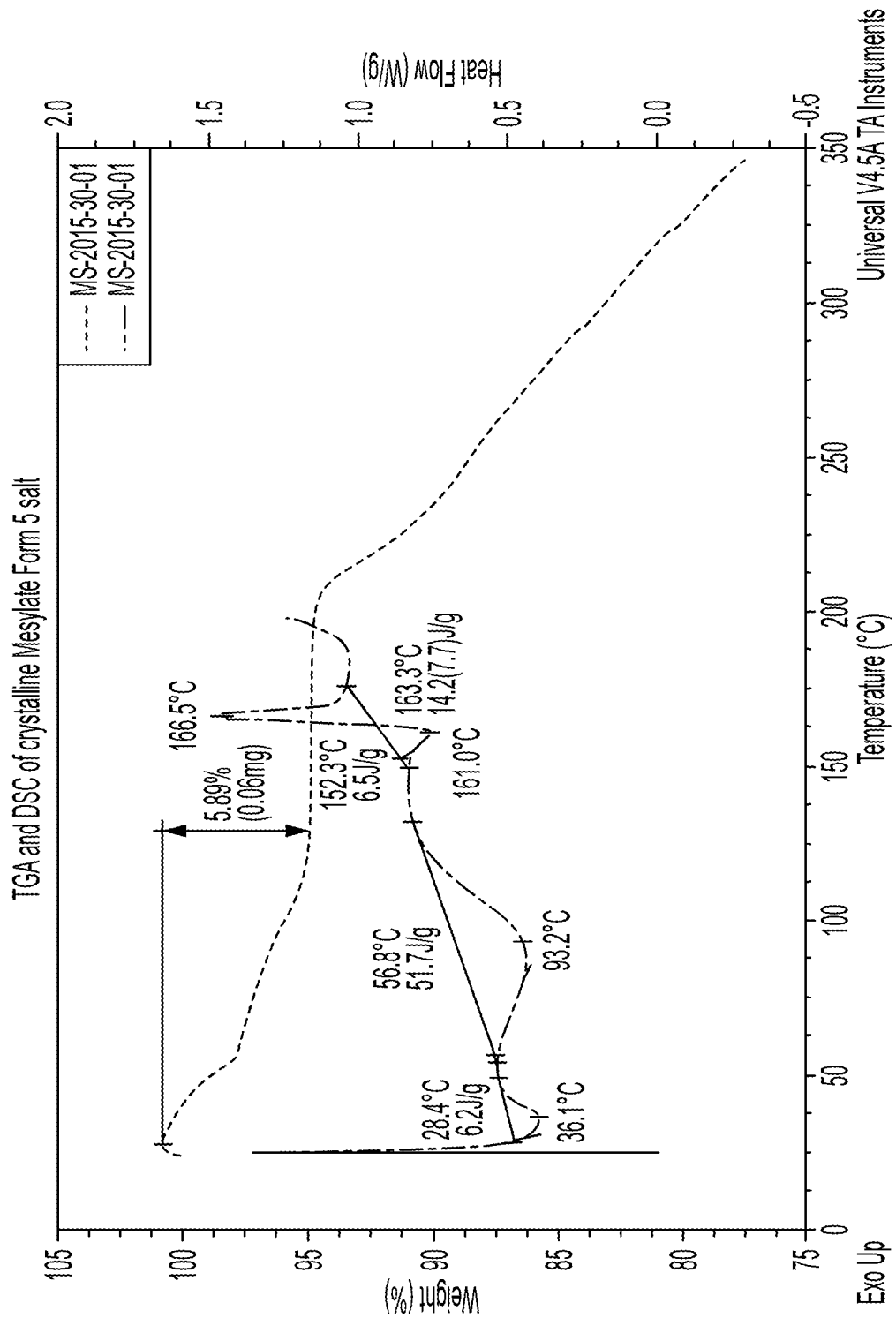
FIG. 26 shows the TGA and DSC of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 5 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 26. In some embodiments, the crystalline form exhibits less than 5.9%±0.5 weight loss up to 130° C.±10.0 as determined by thermogravimetric analysis.

Provided herein is crystalline mesylate Form 5 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by an endothermic event with an onset temperature at 28.4° C.±5.0 (6 J/g) and an endothermic peak at 38.1° C.±5.0; an endothermic event with an onset temperature at 56.8° C.±5.0 (52 J/g) and an endothermic peak at 93.2° C.±5.0; an endothermic event with an onset temperature at 152.3° C.±5.0 (6 J/g) and an endothermic peak at 161° C.±5.0; and an exothermic event with an onset temperature at 163.3° C.±5.0 (14 J/g) and an exothermic peak at 166.5° C. 5.0 as shown in FIG. 26.

Provided herein is the crystalline mesylate Form 5 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6%

(w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Crystalline mesylate Form 6 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 6 salt is characterized by exhibits an X-ray powder diffraction reflection at a 2-theta value of 22.9°±0.3. In some embodiments, the crystalline form exhibits an X-ray powder diffraction reflection at a 2-theta value of 6.7°±0.3 and 16.2°±0.3. In some embodiments, the crystalline form exhibits an X-ray powder diffraction reflection at a 2-theta value of 15.7°±0.3, 20.7°±0.3, and 25.9°±0.3. In some embodiments, the crystalline form exhibits an X-ray powder diffraction reflection at a 2-theta value of 4.3°±0.3, 17.2°±0.3, 25.4°±0.3, and 27.4°±0.3.

Provided herein is crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 6 salt is characterized by at least one X-ray diffraction pattern reflection selected from a 2 theta value of 4.3°±0.3, 6.7°±0.3, 15.7°±0.3, 16.2°±0.3, 17.2°±0.3, 20.7°±0.3, 22.9°±0.3, 25.4°±0.3, 25.9°±0.3, and 27.4°±0.3. In some embodiments, the crystalline mesylate Form 6 salt is characterized by at least two X-ray diffraction pattern reflections selected from a 2 theta value of 4.3° 0.3, 6.7°±0.3, 15.7°±0.3, 16.2°±0.3, 17.2°±0.3, 20.7°±0.3, 22.9°±0.3, 25.4°±0.3, 25.9°±0.3, and 27.4°±0.3. In some embodiments, the crystalline mesylate Form 6 salt is characterized by at least three X-ray diffraction pattern reflections selected from a 2 theta value of 4.3° 0.3, 6.7°±0.3, 15.7°±0.3, 16.2°±0.3, 17.2°±0.3, 20.7°±0.3, 22.9°±0.3, 25.4°±0.3, 25.9°±0.3, and 27.4°±0.3. In some embodiments, the crystalline mesylate Form 6 salt is characterized by at least four X-ray diffraction pattern reflections selected from a 2 theta value of 4.3° 0.3, 6.7°±0.3, 15.7°±0.3, 16.2°±0.3, 17.2°±0.3, 20.7°±0.3, 22.9°±0.3, 25.4°±0.3, 25.9°±0.3, and 27.4°±0.3. In some embodiments, the crystalline mesylate Form 6 salt is characterized by at least five X-ray diffraction pattern reflections selected from a 2 theta value of 4.3°±0.3, 6.7°±0.3, 15.7°±0.3, 16.2°±0.3, 17.2°±0.3, 20.7°±0.3, 22.9°±0.3, 25.4°±0.3, 25.9°±0.3, and 27.4°±0.3.

Figure 29:
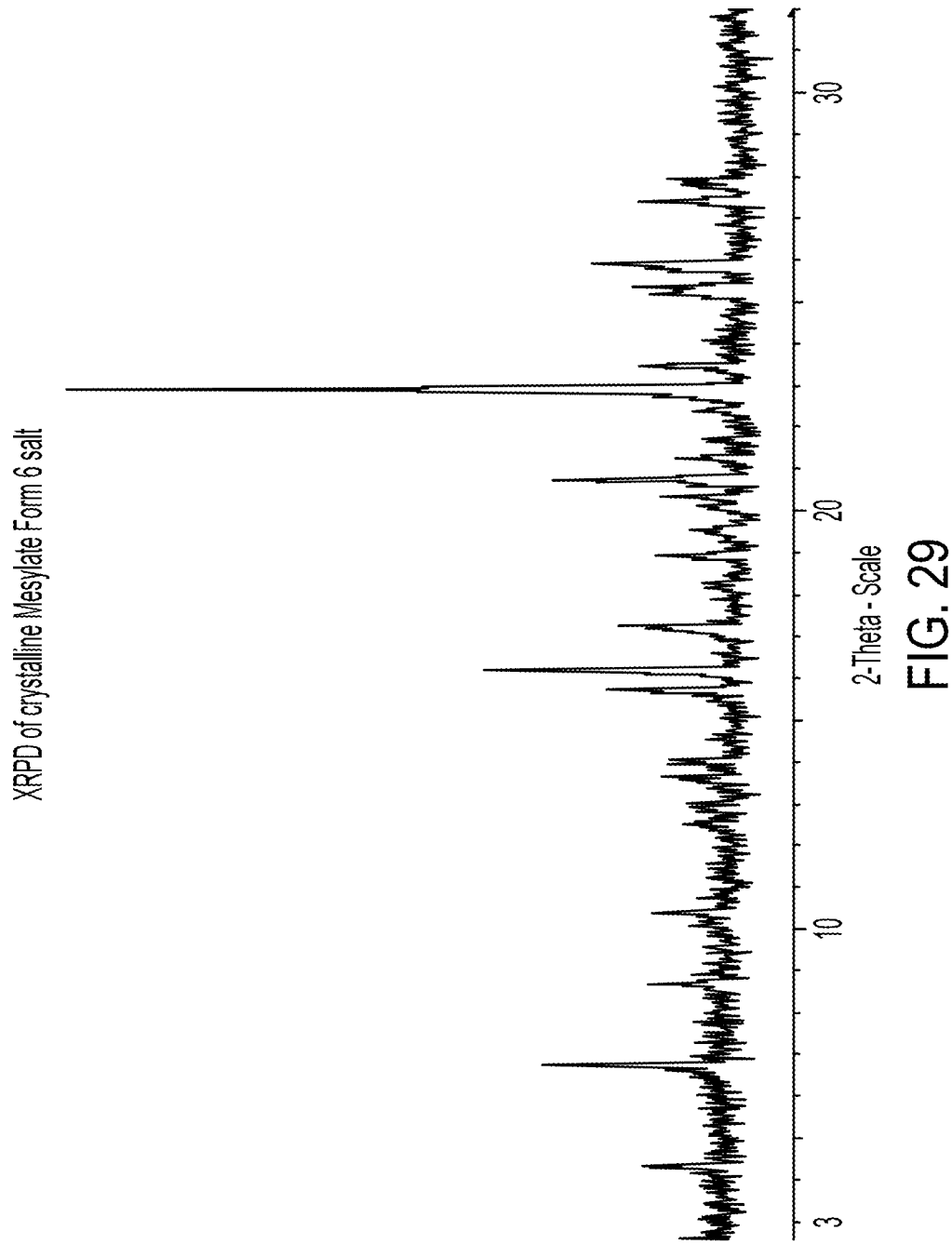
FIG. 29 shows the X-ray powder diffractogram of crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 29.

Figure 30:
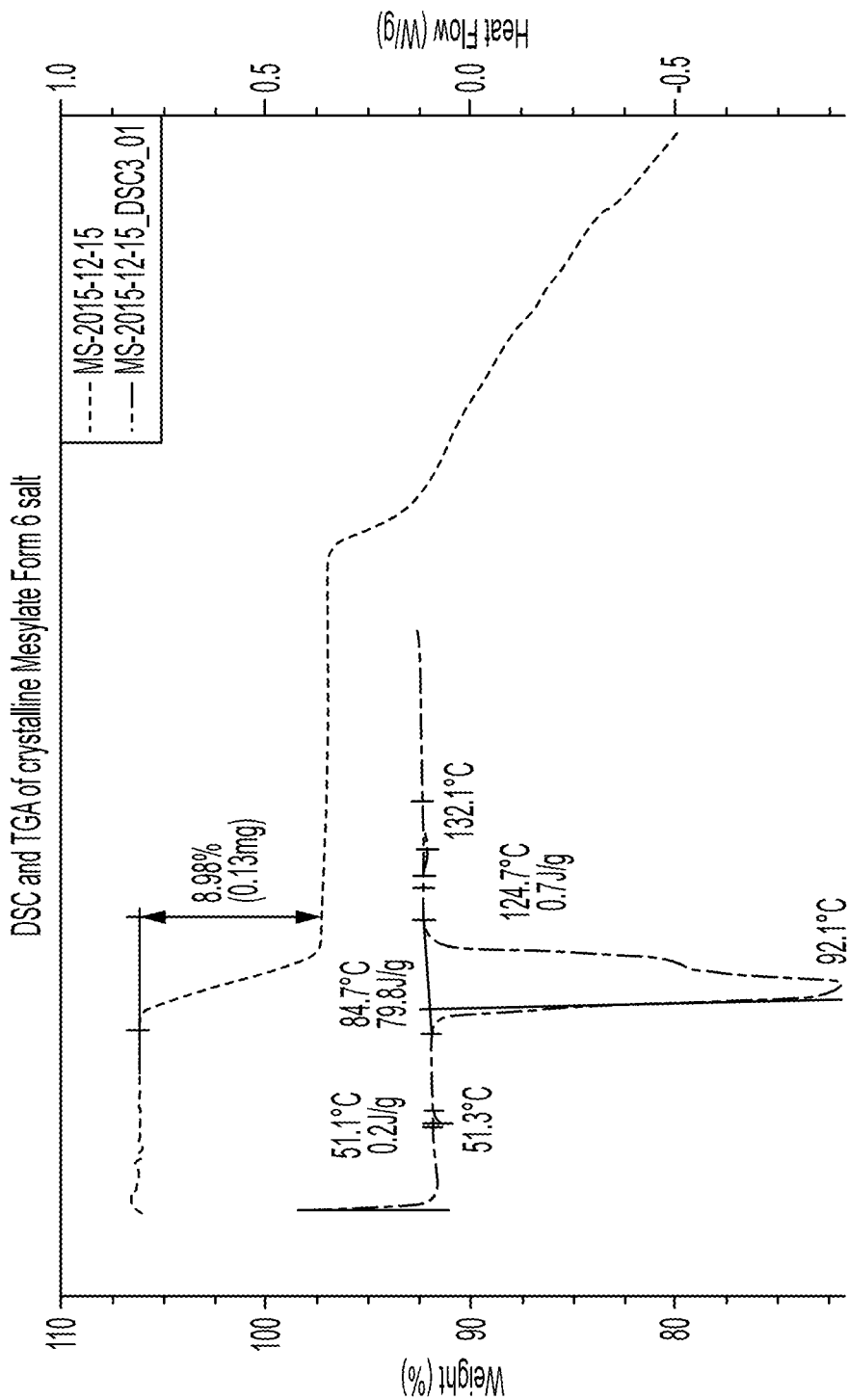
FIG. 30 shows the TGA and DSC pattern of crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 30. In some embodiments, the crystalline form exhibits less than 9.0%±0.5 weight loss up to 113° C.±10.0 as determined by thermogravimetric analysis.

Provided herein is crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by a single endothermic event with an onset temperature at 84.7° C.±5.0 (79.8 J/g) and an endothermic peak at 92.1° C.±5.0 as shown in FIG. 30.

Provided herein is the crystalline mesylate Form 6 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1%

(w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 10% (w/w), less than about 0.50% (w/w), or less than about 0.2% (w/w).

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Crystalline mesylate Form 7 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 7 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 7 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 7 salt is characterized by exhibits an X-ray powder diffraction reflection at a 2-theta value of 16.3°±0.3. In some embodiments, the crystalline form exhibits an X-ray powder diffraction reflection at a 2-theta value of 20.6°±0.3 and 22.9°±0.3. In some embodiments, the crystalline form exhibits an X-ray powder diffraction reflection at a 2-theta value of 15.6°±0.3 and 21.4°±0.3. In some embodiments, the crystalline form exhibits an X-ray powder diffraction reflection at a 2-theta value of 6.7°±0.3, 10.4°±0.3, 23.3°±0.3, and 25.2°±0.3.

Provided herein is crystalline mesylate Form 7 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 7 salt is characterized by at least one X-ray diffraction pattern reflection selected from a 2 theta value of 6.7°±0.3, 10.4°±0.3, 15.6°±0.3, 16.3°±0.3, 20.6°±0.3, 21.4°±0.3, 22.9°±0.3, 23.3°±0.3, and 25.2°±0.3. In some embodiments, the crystalline mesylate Form 7 salt is characterized by at least two X-ray diffraction pattern reflections selected from a 2 theta value of 6.7°±0.3, 10.4°±0.3, 15.6°±0.3, 16.3°±0.3, 20.6°±0.3, 21.4°±0.3, 22.9°±0.3, 23.3°±0.3, and 25.2°±0.3. In some embodiments, the crystalline mesylate Form 7 salt is characterized by at least three X-ray diffraction pattern reflections selected from a 2 theta value of 6.7° 0.3, 10.4°±0.3, 15.6°±0.3, 16.3°±0.3, 20.6°±0.3, 21.4°±0.3, 22.9°±0.3, 23.3°±0.3, and 25.2°±0.3. In some embodiments, the crystalline mesylate Form 7 salt is characterized by at least four X-ray diffraction pattern reflections selected from a 2 theta value of 6.7°±0.3, 10.4°±0.3, 15.6°±0.3, 16.30 0.3, 20.6°±0.3, 21.4°±0.3, 22.9°±0.3, 23.3°±0.3, and 25.2°±0.3. In some embodiments, the crystalline mesylate Form 7 salt is characterized by at least five X-ray diffraction pattern reflections selected from a 2 theta value of 6.7°±0.3, 10.4°±0.3, 15.6°±0.3, 16.3° 0.3, 20.6°±0.3, 21.4°±0.3, 22.9°±0.3, 23.3°±0.3, and 25.2°±0.3.

Figure 31:
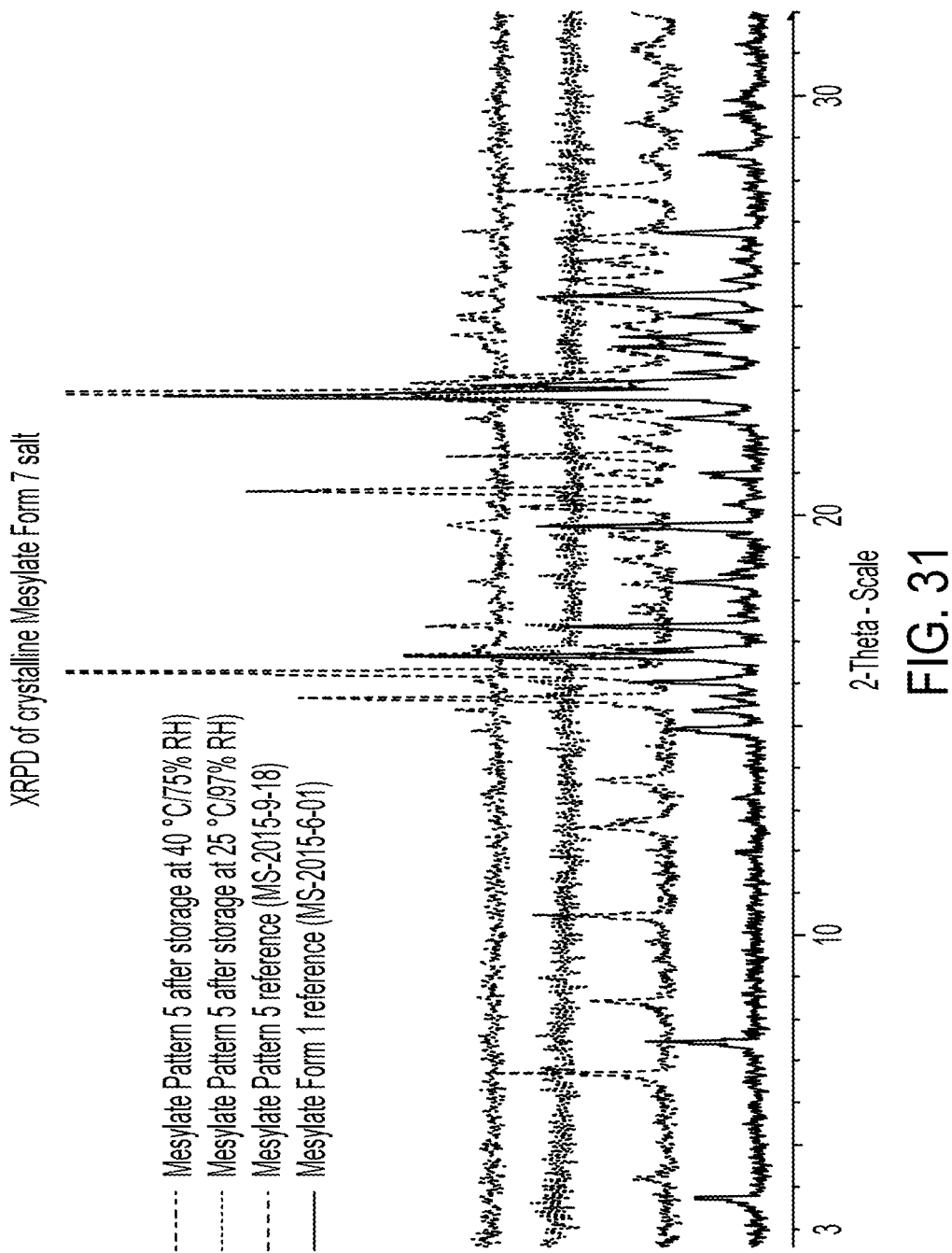
FIG. 31 shows the X-ray powder diffractogram of crystalline mesylate Form 7 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 7 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 31.

Provided herein is the crystalline mesylate Form 7 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Crystalline mesylate Form 8 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 8 salt is characterized by exhibits an X-ray powder diffraction reflection at a 2-theta value of 4.4°±0.3. In some embodiments, the crystalline form exhibits an X-ray powder diffraction reflection at a 2-theta value of 6.8°±0.3 and 16.2°±0.3. In some embodiments, the crystalline form exhibits an X-ray powder diffraction reflection at a 2-theta value of 8.7°±0.3 and 14.1°±0.3. In some embodiments, the crystalline form exhibits an X-ray powder diffraction reflection at a 2-theta value of 13.1°±0.3, 18.2°±0.3, 20.4°±0.3, and 20.8°±0.3.

Provided herein is crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 8 salt is characterized by at least one X-ray diffraction pattern reflection selected from a 2 theta value of 4.4°±0.3, 6.8°±0.3, 8.7°±0.3, 13.1°±0.3, 14.1° 0.3, 16.2°±0.3, 18.2°±0.3, 20.4°±0.3, and 20.8°±0.3. In some embodiments, the crystalline mesylate Form 8 salt is characterized by at least two X-ray diffraction pattern reflections selected from a 2 theta value of 4.4°±0.3, 6.8°±0.3, 8.7°±0.3, 13.1°±0.3, 14.1°±0.3, 16.2°±0.3, 18.2°±0.3, 20.4°±0.3, and 20.8°±0.3. In some embodiments, the crystalline mesylate Form 8 salt is characterized by at least three X-ray diffraction pattern reflections selected from a 2 theta value of 4.4°±0.3, 6.8°0.3, 8.7°±0.3, 13.1°±0.3, 14.1°±0.3, 16.2°±0.3, 18.2°±0.3, 20.4°±0.3, and 20.8°±0.3. In some embodiments, the crystalline mesylate Form 8 salt is characterized by at least four X-ray diffraction pattern reflections selected from a 2 theta value of 4.4°±0.3, 6.8°±0.3, 8.7°±0.3, 13.1°±0.3, 14.1°±0.3, 16.2°±0.3, 18.2°±0.3, 20.4°±0.3, and 20.8°±0.3. In some embodiments, the crystalline mesylate Form 8 salt is characterized by at least five X-ray diffraction pattern reflections selected from a 2 theta value of 4.4°±0.3, 6.8°±0.3, 8.7°±0.3, 13.1° 0.3, 14.1° 0.3, 16.2°±0.3, 18.2°±0.3, 20.4°±0.3, and 20.8°±0.3.

Figure 32:
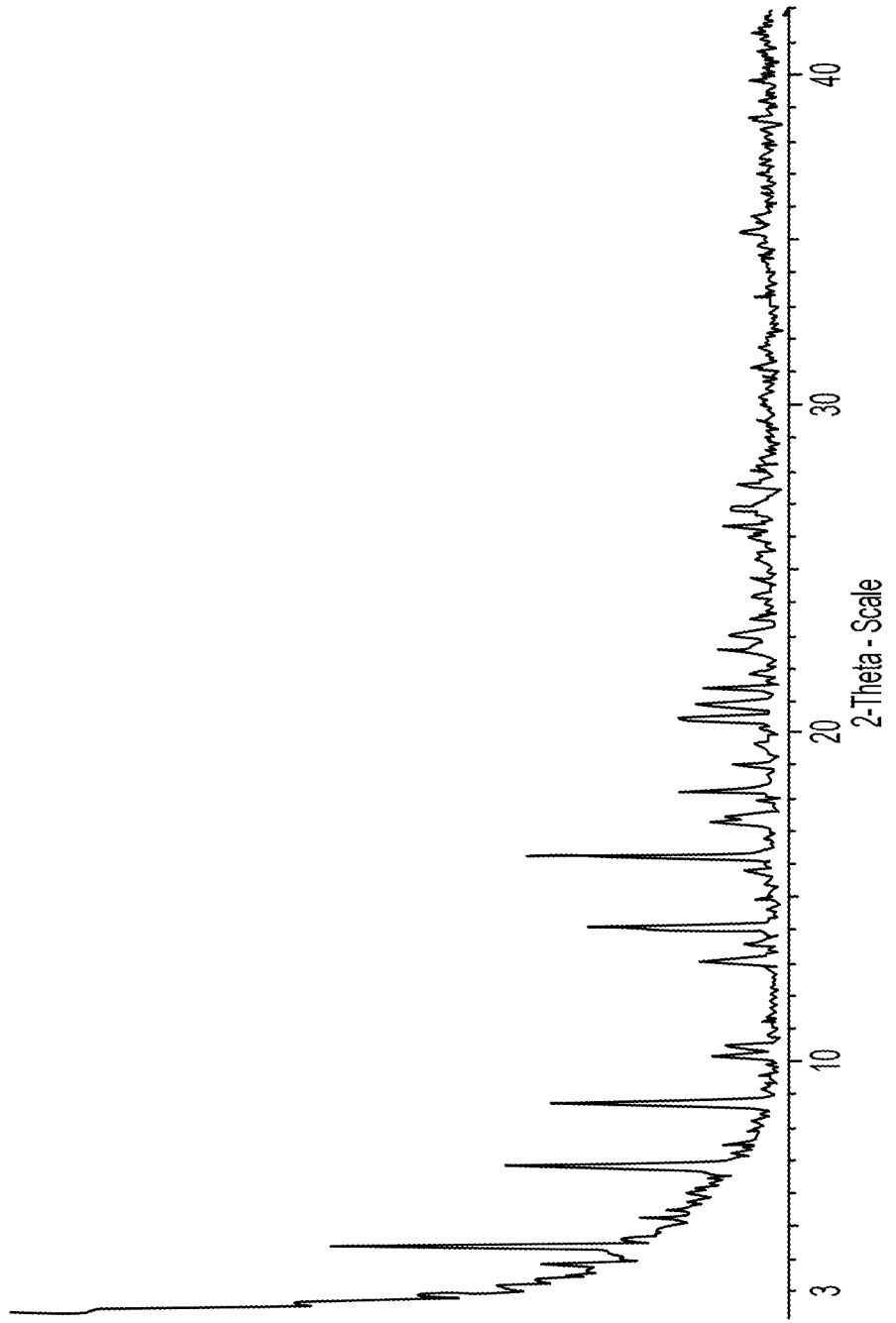
FIG. 32 shows the X-ray powder diffractogram of crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 32.

Figure 33:
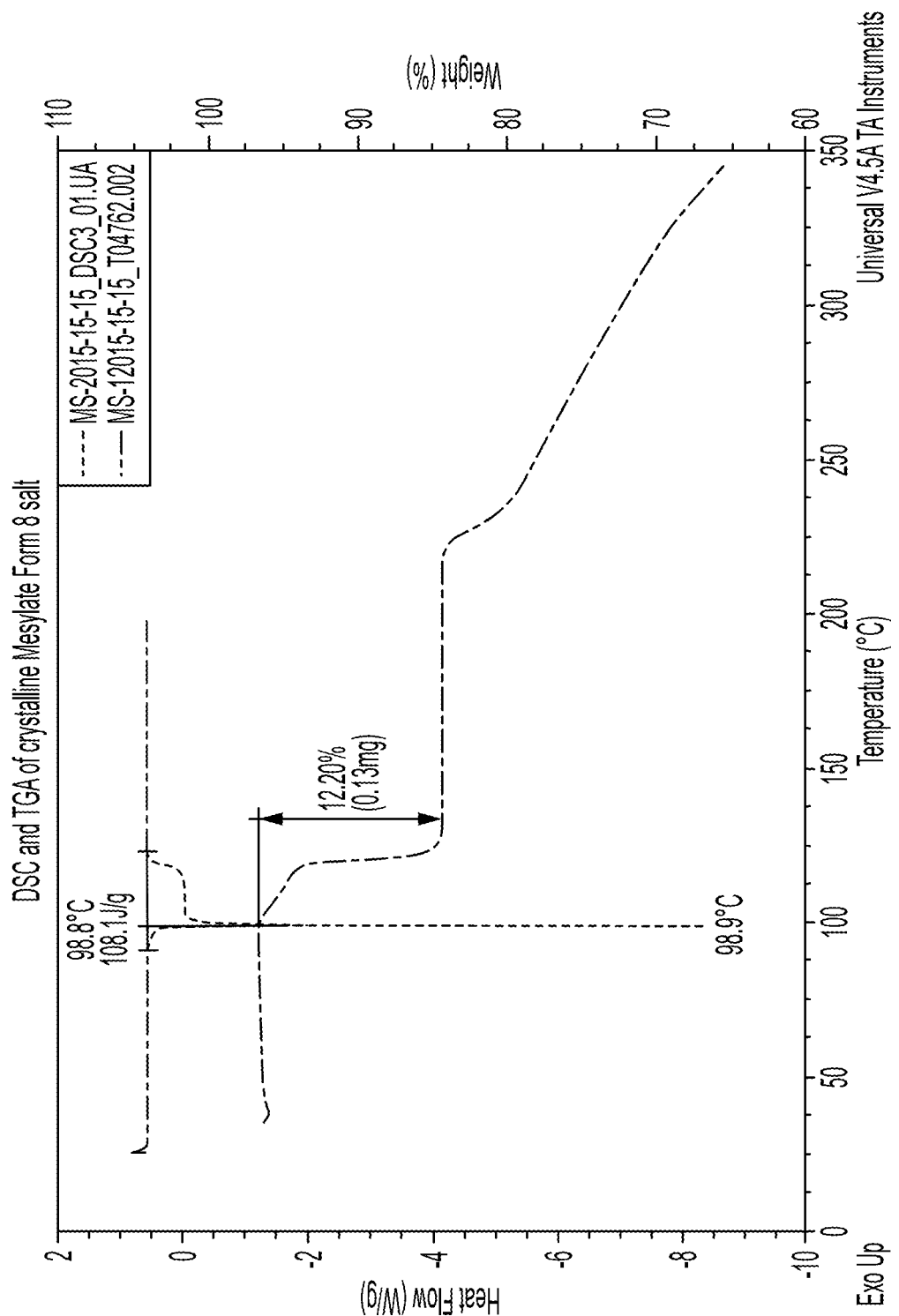
FIG. 33 shows the TGA and DSC pattern of crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 33. In some embodiments, the crystalline form exhibits less than 12.2%±0.5 weight loss up to 134° C.±10.0 as determined by thermogravimetric analysis.

Provided herein is crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by a single endothermic event with an onset temperature at 98.8° C.+5.0 (108.1 J/g) and an endothermic peak at 98.9° C.±5.0 as shown in FIG. 33.

Provided herein is the crystalline mesylate Form 8 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5%

(w/w), less than about 4.75% (w/w), less than about 4.5% (w/w), less than about 4.25% (w/w), less than about 4% (w/w), less than about 3.75% (w/w), less than about 3.5% (w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Crystalline mesylate Form 9 salt of N-Hydroxy 2-{6-[(6-fluoro-quinolin-2-ylmethyl)-amino]-3-aza-bicyclo[3.1.0]hex-3-yl}pyrimidine-5-carboxamide Provided herein is crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 9 salt is characterized by exhibits an X-ray powder diffraction reflection at a 2-theta value of 17.2°±0.3. In some embodiments, the crystalline form exhibits an X-ray powder diffraction reflection at a 2-theta value of 4.2°±0.3 and 8.4°±0.3. In some embodiments, the crystalline form exhibits an X-ray powder diffraction reflection at a 2-theta value of 8.6°±0.3 and 15.0°±0.3. In some embodiments, the crystalline form exhibits an X-ray powder diffraction reflection at a 2-theta value of 22.2°±0.3 and 24.1°±0.3.

Provided herein is crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide, wherein the crystalline mesylate Form 9 salt is characterized by at least one X-ray diffraction pattern reflection selected from a 2 theta value of 4.2°±0.3, 8.4°±0.3, 8.6°±0.3, 15.0°±0.3, 17.2°±0.3, 22.2°±0.3 and 24.1°±0.3. In some embodiments, the crystalline mesylate Form 9 salt is characterized by at least two X-ray diffraction pattern reflections selected from a 2 theta value of 4.2°±0.3, 8.4°±0.3, 8.6°±0.3, 15.0°±0.3, 17.2°±0.3, 22.2°±0.3 and 24.1°±0.3. In some embodiments, the crystalline mesylate Form 9 salt is characterized by at least three X-ray diffraction pattern reflections selected from a 2 theta value of 4.2°±0.3, 8.4°±0.3, 8.6°±0.3, 15.0°±0.3, 17.2°±0.3, 22.2°±0.3 and 24.1°±0.3. In some embodiments, the crystalline mesylate Form 9 salt is characterized by at least four X-ray diffraction pattern reflections selected from a 2 theta value of 4.2°±0.3, 8.4°±0.3, 8.6°±0.3, 15.0°±0.3, 17.2°±0.3, 22.2°±0.3 and 24.1°±0.3. In some embodiments, the crystalline mesylate Form 9 salt is characterized by at least five X-ray diffraction pattern reflections selected from a 2 theta value of 4.2°±0.3, 8.4°±0.3, 8.6°±0.3, 15.0°±0.3, 17.2°±0.3, 22.2°±0.3 and 24.1°±0.3.

Figure 34:
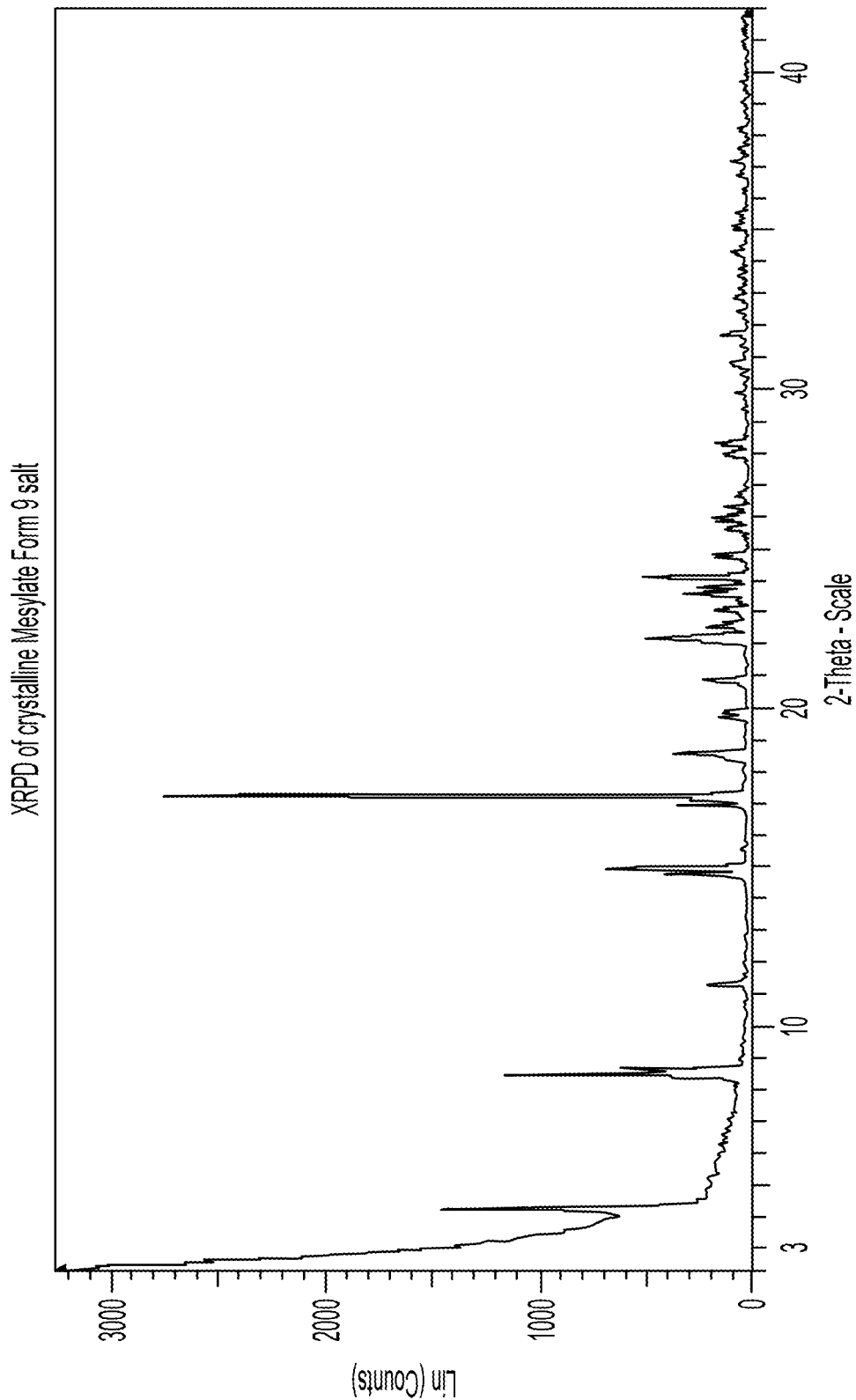
FIG. 34 shows the X-ray powder diffractogram of crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 34.

Figure 35:
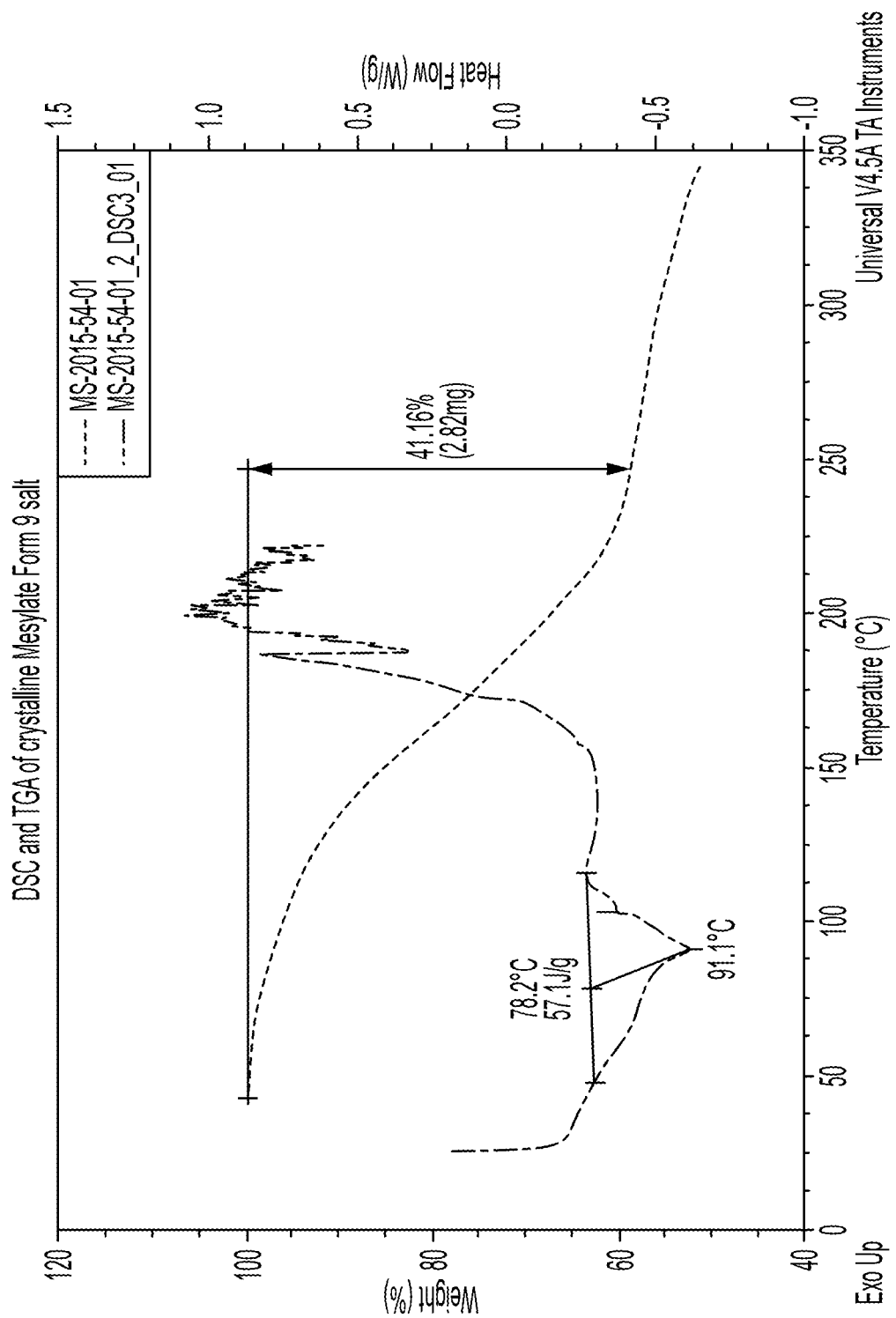
FIG. 35 shows the TGA and DSC pattern of crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide.

Provided herein is crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 35. In some embodiments, the crystalline form exhibits less than 41.2%±0.5 weight loss up to 247° C.±10.0 as determined by thermogravimetric analysis.

Provided herein is crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by an endothermic event with an onset temperature at 78.2° C.±5.0 (57.7 J/g) and an endothermic peak at 91.1° C.±5.0 as shown in FIG. 35.

Provided herein is the crystalline mesylate Form 9 salt N-hydroxy 2-{6-[(6-fluoro-quinolin-2-ylmethyl)-amino]-3-aza-bicyclo[3.1.0]hex-3-yl}pyrimidine-5-carboxamide or a pharmaceutically acceptable salt, solution or hydrate thereof, substantially free of impurities. In some embodiments, the compound is substantially free of structurally related impurities. One embodiment provides a composition wherein the amount of impurities is less than 1% (w/w). One embodiment provides a composition wherein the amount of impurities is less than 0.5% (w/w). One embodiment provides a composition wherein the amount of impurities is less than 0.4% (w/w). One embodiment provides a composition wherein the amount of impurities is less than 0.3% (w/w). One embodiment provides a composition wherein the amount of impurities is less than 0.25% (w/w). One embodiment provides a composition wherein the amount of impurities is less than 0.20% (w/w). One embodiment provides a composition wherein the amount of impurities is less than 0.15% (w/w). One embodiment provides a composition wherein the amount of impurities is less than 0.10% (w/w). One embodiment provides a composition wherein the amount of impurities is less than 0.08% (w/w). One embodiment provides a composition wherein the amount of impurities is less than 0.05% (w/w). One embodiment provides a composition wherein the amount of impurities is not more than 1% (w/w). One embodiment provides a composition wherein the amount of impurities is not more than 0.5% (w/w). One embodiment provides a composition wherein the amount of impurities is not more than 0.4% (w/w). One embodiment provides a composition wherein the amount of impurities is not more than 0.3% (w/w). One embodiment provides a composition wherein the amount of impurities is not more than 0.25% (w/w). One embodiment provides a composition wherein the amount of impurities is not more than 0.20% (w/w). One embodiment provides a composition wherein the amount of impurities is not more than 0.15% (w/w). One embodiment provides a composition wherein the amount of impurities is not more than 0.10% (w/w). One embodiment provides a composition wherein the amount of impurities is not more than 0.08% (w/w). One embodiment provides a composition wherein the amount of impurities is not more than 0.05% (w/w). One embodiment provides a composition wherein the amount of impurities is not detectable.

One embodiment provides a composition wherein substantially free means less than about 10% (w/w), less than about 9% (w/w), less than about 8% (w/w), less than about 7% (w/w), less than about 6% (w/w), less than about 5% (w/w), less than about 4.75% (w/w), less than about 4.5% (w/w), less than about 4.25% (w/w), less than about 4% (w/w), less than about 3.75% (w/w), less than about 3.5%

(w/w), less than about 3.25% (w/w), less than about 3% (w/w), less than about 2.75% (w/w), less than about 2.5% (w/w), less than about 2.25% (w/w), less than about 2% (w/w), less than about 1.75% (w/w), less than about 1.5% (w/w), less than about 1.25% (w/w), less than about 1% (w/w), less than about 0.9% (w/w), less than about 0.8% (w/w), less than about 0.7% (w/w), less than about 0.6% (w/w), less than about 0.5% (w/w), less than about 0.4% (w/w), less than about 0.3% (w/w), less than about 0.25% (w/w), less than about 0.20% (w/w), less than about 0.15% (w/w), less than about 0.1% (w/w), less than about 0.08% (w/w), or less than about 0.05% (w/w). One embodiment provides a composition wherein substantially free means an undetectable amount. One embodiment provides a composition wherein substantially free means less than about 5% (w/w), less than about 3% (w/w), less than about 1% (w/w), less than about 0.5% (w/w), or less than about 0.2% (w/w).

Pharmaceutical Compositions

Provided herein is a pharmaceutical composition comprising any crystalline mesylate salt Forms 1-9 of N-hydroxy 2-{6-[(6-fluoro-quinolin-2-ylmethyl)-amino]-3-aza-bicyclo[3.1.0]hex-3-yl}pyrimidine-5-carboxamide or combinations thereof, and one or more pharmaceutically acceptable excipients or carriers. In various embodiments, the pharmaceutical composition further comprises at least one pharmaceutically acceptable vehicle, carrier, diluent, or excipient, or a mixture thereof. In some embodiments, provided herein is a pharmaceutical composition comprising any crystalline mesylate salt Forms 1-9 of N-hydroxy 2-{6-[(6-fluoro-quinolin-2-ylmethyl)-amino]-3-aza-bicyclo[3.1.0]hex-3-yl}pyrimidine-5-carboxamide or combinations thereof, one or more pharmaceutically acceptable excipients or carriers and one or more additional active pharmaceutical ingredients (API). In some embodiments, the additional API is valganciclovir.

Provided herein is a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, and one or more pharmaceutically acceptable excipients or carriers. In various embodiments, the pharmaceutical composition further comprises at least one pharmaceutically acceptable vehicle, carrier, diluent, or excipient, or a mixture thereof. Provided herein is a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide, one or more pharmaceutically acceptable excipients or carriers, and one or more additional active pharmaceutical ingredients (API). In some embodiments, the additional API is valganciclovir.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 7.5, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 3.7, and 14.9, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by an X-ray diffraction pattern reflection at a 2 theta value of 3.7, 7.5, and 14.9, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by at least one X-ray diffraction pattern reflection selected from a 2 theta value of 3.7, 7.5, 14.9, 17.3, 19.7, 22.5, 22.9, or 30.1, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by at least two X-ray diffraction pattern reflections selected from a 2 theta value of 3.7, 7.5, 14.9, 17.3, 19.7, 22.5, 22.9, or 30.1, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by at least three X-ray diffraction pattern reflections selected from a 2 theta value of 3.7, 7.5, 14.9, 17.3, 19.7, 22.5, 22.9, or 30.1, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by at least four X-ray diffraction pattern reflections selected from a 2 theta value of 3.7, 7.5, 14.9, 17.3, 19.7, 22.5, 22.9, or 30.1, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide as characterized by at least five X-ray diffraction pattern reflections selected from a 2 theta value of 3.7, 7.5, 14.9, 17.3, 19.7, 22.5, 22.9, or 30.1, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the X-ray powder diffraction pattern as shown in FIG. 1, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide exhibiting the TGA pattern as shown in FIG. 3, and one or more pharmaceutically acceptable excipients or carriers.

One embodiment provides a pharmaceutical composition comprising crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide wherein the DSC is characterized by a single endothermic event with an onset temperature at about 222.1° C. (433 J/g), and one or more pharmaceutically acceptable excipients or carriers.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted overtime according to the individual need and the professional judgment of the person administering or supervising the administration of the formulations.

Treatment dosages generally may be titrated to optimize safety and efficacy. Typically, dosage-effect relationships from in vitro studies initially can provide useful guidance on the proper doses for patient administration. Studies in animal models also generally may be used for guidance regarding effective dosages for treatment in accordance with the present disclosure. In terms of treatment protocols, it should be appreciated that the dosage to be administered will depend on several factors, including the particular agent that is administered, the route administered, the condition of the particular patient, etc. Determination of these parameters is well within the skill of the art. These considerations, as well as effective formulations and administration procedures are well known in the art and are described in standard textbooks. One embodiment provides a method of treating Epstein Bar Virus Associated Lymphoid Malignancies in a patient need thereof, comprising administering to the patient a pharmaceutical composition comprising a solid state form of a mesylate slat of Compound 1. In some embodiments, the solid state form of the mesylate salt of Compound 1 is the amorphous form. In some embodiments, the solid state form of the mesylate salt of Compound 1 is any one of crystalline Forms 1-9. In some embodiments, the solid state form of the mesylate salt of Compound 1 is crystalline Form 1. In some embodiments, the method comprises administering the solid state form of Compound 1 in combination with valganciclovir.

The pharmaceutical compositions provided herein are formulated in various dosage forms for oral administration. These dosage forms can be prepared according to conventional methods and techniques known to those skilled in the art (see, *Remington: The Science and Practice of Pharmacy*, Loyd V., Jr, Allen, Ed., Pharmaceutical Press.: New York, NY, 2002; Vol. 22).

As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, orally disintegrating tablets, dispersible tablets, bulk powders, and effervescent or non-effervescent powders or granules. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents. In some embodiments, the oral dosage form is a tablet, capsule, or pill. In further embodiments, the oral dosage form is a liquid, tablet for oral suspension or packet of powder to be dissolved in a beverage.

In further embodiments, the pharmaceutical compositions provided herein may be provided as compressed tablets, tablet triturates, chewable lozenges, rapidly dissolving tablets, multiple compressed tablets, or enteric-coating tablets, sugar-coated, or film-coated tablets.

Enteric-coated tablets are compressed tablets coated with substances that resist the action of stomach acid but dissolve or disintegrate in the intestine, thus protecting the active ingredients from the acidic environment of the stomach.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule, consists of two sections, one slipping over the other, thus completely enclosing the active ingredient. The soft elastic capsule is a soft, globular shell, such as a gelatin shell, which is plasticized by the addition of glycerin, sorbitol, or a similar polyol. The liquid, semisolid, and solid dosage forms provided herein may be encapsulated in a capsule. Suitable liquid and semisolid dosage forms include solutions and suspensions in propylene carbonate, vegetable oils, or triglycerides.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

The examples and preparations provided below further illustrate and exemplify the salt forms of the present disclosure and methods of preparing such salt forms. It is to be understood that the scope of the present disclosure is not limited in any way by the scope of the following examples and preparations.

EXAMPLES

The present disclosure is further illustrated by the following examples, which should not be construed as limiting in any way. The experimental procedures to generate the data shown are discussed in more detail below. The disclosure has been described in an illustrative manner, and it is to be understood that the terminology used is intended to be in the nature of description rather than of limitation.

General Experimental, Instrument, and Methodology Details
X-Ray Powder Diffraction
Bruker AXS D8 Advance XRPD diffractograms were collected on a Bruker D8 diffractometer using Cu Kα, radiation (40 kV, 40 mA) and a 0-2θ goniometer fitted with a Ge monochromator. The incident beam passes through a 2.0 mm divergence slit followed by a 0.2 mm anti-scatter slit and knife edge. The diffracted beam passes through an 8.0 mm receiving slit with 2.5° Soller slits followed by the Lynxeye Detector. The software used for data collection and analysis was Diffrac Plus XRD Commander and Diffrac Plus EVA respectively.

Samples were run under ambient conditions as flat plate specimens using powder as received. The sample was prepared on a polished, zero-background (510) silicon wafer by gently pressing onto the flat surface or packed into a cut cavity. The sample was rotated in its own plane.

The details of the collection method are:
Angular range: 2 to 42° 2θ; Step size: 0.05° 2θ; Collection time: 0.5 s/step (total collection time: 6.40 min).

PANalytical Empyrean

XRPD diffractograms were collected on a PANalytical Empyrean diffractometer using Cu Kα, radiation (45 kV, 40 mA) in transmission geometry. A 0.5° slit, 4 mm mask and 0.04 rad Soller slits with a focusing mirror were used on the incident beam. A PIXcel3D detector, placed on the diffracted beam, was fitted with a receiving slit and 0.04 rad Soller slits. The software used for data collection was X'Pert Data Collector using X'Pert Operator Interface. The data were analyzed and presented using Diffrac Plus EVA or High-Score Plus.

Samples were prepared and analyzed in a metal well-plate in transmission mode. X-ray transparent film was used between the metal sheets on the metal well-plate and powders (approximately 1-2 mg) were used as received. The scan mode for the metal plate used the gonio scan axis. The details of the standard screening data collection method are: Angular range: 2.5 to 32.0° 2θ; Step size: 0.013° 2θ; Collection time: 12.75 s/step (total collection time of 2.07 min).

Nuclear Magnetic Resonance (NMR)
NMR Using DRX400 Console $^1$H NMR spectra were collected on a Bruker 400 MHz instrument equipped with an auto-sampler and controlled by a DRX400 console. Samples were prepared in DMSO-$d_6$ solvent, unless otherwise stated. Automated experiments were acquired using ICON-NMR configuration within Topspin software, using standard Bruker-loaded experiments ($^1$H). Off-line analysis was performed using ACD Spectrus Processor.

NMR Using Avance NEO Nanobay Console $^1$H NMR spectra were collected on a Bruker 400 MHz instrument equipped with an auto-sampler and controlled by a Avance NEO nanobay console. Samples were prepared in DMSO-$d_6$ solvent, unless otherwise stated. Automated experiments were acquired using ICON-NMR configuration within Topspin 4.1.1 software, using standard Bruker-loaded experiments ($^1$H). Off-line analysis was performed using ACD Spectrus Processor 2016.

Differential Scanning Calorimetry (DSC)
TA Instruments Q2000

DSC data were collected on a TA Instruments Q2000 equipped with a 50 position auto-sampler. Typically, 0.5-3 mg of each sample, in a pin-holed aluminium pan, was heated at 10° C./min from 25° C. to max 245° C. A purge of dry nitrogen at 50 ml/min was maintained over the sample. Modulated temperature DSC was carried out using an underlying heating rate of 2° C./min and temperature modulation parameters of 0.636° C. (amplitude) every 60 seconds (period). The instrument control software was Advantage for Q Series and Thermal Advantage and the data were analysed using Universal Analysis or TRIOS.

TA Instruments Discovery DSC

DSC data were collected on a TA Instruments Discovery DSC equipped with a 50 position auto-sampler. Typically, 0.5-3 mg of each sample, in a pin-holed aluminium pan, was heated at 10° C./min from 25° C. to 200° C. A purge of dry nitrogen at 50 ml/min was maintained over the sample. The instrument control software was TRIOS and the data were analysed using TRIOS or Universal Analysis.

Thermo-Gravimetric Analysis (TGA)
TA Instruments Q500

TGA data were collected on a TA Instruments Q500 TGA, equipped with a 16 position auto-sampler. Typically, 5-10 mg of each sample was loaded onto a pre-tared aluminium DSC pan and heated at 10° C./min from ambient temperature to 350° C. A nitrogen purge at 60 ml/min was maintained over the sample. The instrument control software was Advantage for Q Series and Thermal Advantage and the data were analysed using Universal Analysis or TRIOS.

TA Instruments Discovery TGA

TGA data were collected on a TA Instruments Discovery TGA, equipped with a 25 position auto-sampler. Typically, 5-10 mg of each sample was loaded onto a pre-tared aluminium DSC pan and heated at 10° C./min from ambient temperature to 350° C. A nitrogen purge at 25 ml/min was maintained over the sample. The instrument control software was TRIOS and the data were analysed using TRIOS or Universal Analysis.

Polarised Light Microscopy (PLM)

Samples were studied on a Nikon SMZ1500 polarized light microscope with a digital video camera connected to a DS Camera control unit DS-L2 for image capture. The sample was viewed with appropriate magnification and partially polarised light, coupled to a λ false-colour filter.

Scanning Electron Microscopy (SEM)

Data were collected on a Phenom Pro Scanning Electron Microscope. A small quantity of sample was mounted onto an aluminium stub using conducting double-sided adhesive tape. A thin layer of gold was applied using a sputter coater (20 mA, 120 s).

Gravimetric Vapour Sorption (GVS)

Sorption isotherms were obtained using a SMS DVS Intrinsic moisture sorption analyser, controlled by DVS Intrinsic Control software. The sample temperature was maintained at 25° C. by the instrument controls. The humidity was controlled by mixing streams of dry and wet nitrogen, with a total flow rate of 200 ml/min. The relative humidity was measured by a calibrated Rotronic probe (dynamic range of 1.0-100% RH), located near the sample. The weight change, (mass relaxation) of the sample as a function of % RH was constantly monitored by a microbalance (accuracy ±0.005 mg).

Typically, 20-30 mg of sample was placed in a tared mesh stainless steel basket under ambient conditions. The sample was loaded and unloaded at 40% RH and 25° C. (typical room conditions). A moisture sorption isotherm was performed as outlined below (2 scans per complete cycle). The standard isotherm was performed at 25° C. at 10% RH intervals over a 0-90% RH range. Typically, a double cycle (4 scans) was carried out. Data analysis was carried out within Microsoft Excel using the DVS Analysis Suite.

TABLE 1

| Method for SMS DVS Intrinsic experiments | |
|---|---|
| Parameter | Value |
| Adsorption - Scan 1 | 40-90 |
| Desorption, Adsorption - Scan 2 | 90-0, 0-40 |
| Intervals (% RH) | 10 |
| Number of Scans | 4 |
| Flow rate (ml/min) | 200 |
| Temperature (° C.) | 25 |
| Stability (° C./min) | 0.2 |
| Sorption Time (hours) | 6 hour time out |
| Number of cycles | 2 |

Chemical Purity Determination by HPLC

Purity analysis was performed on an AgilentHP1100/Infinity 111260 series system equipped with a diode array detector and using OpenLAB software. The full method details are provided below:

TABLE 2

HPLC method for chemical purity determinations

| Parameter | Value |
| --- | --- |
| Type of method | Reverse phase with gradient elution |
| Sample Preparation | 0.2 (equivalent free base) mg/ml in acetonitrile: water 1:1 |
| | Sample sonicated for ca. 1 h to ensure complete dissolution |
| Column | Supelco Ascends Express C18 2.7 μm 100 × 4.6 mm |
| Column Temperature (° C.) | 25 |
| Injection (μl) | 5 |
| Detection: Wavelength, Bandwidth, (nm) | 255, 90 |
| Flow Rate (ml/min) | 2 |
| Phase A | 0.1% TFA in water |
| Phase B | 0.085% TFA in acetonitrile |

| | Time (min) | % Phase A | % Phase B |
| --- | --- | --- | --- |
| Timetable | 0 | 95 | 5 |
| | 6 | 5 | 95 |
| | 6.2 | 95 | 5 |
| | 8 | 95 | 5 |

Water Determination by Karl Fischer Titration (KF)

The water content of each sample was measured on a Metrohm 874 Oven Sample Processor at 150° C. with 851 Titrano Coulometer using Hydranal Coulomat AG oven reagent and nitrogen purge. Weighed solid samples were introduced into a sealed sample vial. Approximately 10 mg of sample was used per titration and duplicate determinations were made. An average of these results is presented unless otherwise stated. Data collection and analysis were performed using Tiamo software.

Ion Chromatography (IC)

Data were collected on a Metrohm 930 Compact IC Flex with 858 Professional autosampler and 800 Dosino dosage unit monitor, using IC MagicNet software. Accurately weighed samples were prepared as stock solutions in a suitable solvent. Quantification was achieved by comparison with standard solutions of known concentration of the ion being analysed. Analyses were performed in duplicate and an average of the values is given unless otherwise stated.

TABLE 3

IC method for cation chromatography

| Parameter | Value |
| --- | --- |
| Type of method | Cation exchange |
| Column | Metrosep C 4-250 (4.0 × 250 mm) |
| Column Temperature (° C.) | Ambient |
| Injection (μl) | Various |
| Detection | Conductivity detector |
| Flow Rate (ml/min) | 0.9 |
| Eluent | 1.7 mM nitric acid 0.7 mM dipicolinic acid in a 5% acetone aqueous solution. |

TABLE 4

IC method for anion chromatography

| Parameter | Value |
| --- | --- |
| Type of method | Anion exchange |
| Column | Metrosep A Supp 5-150 (4.0 × 150 mm) |
| Column Temperature (° C.) | Ambient |
| Injection (μl) | Various |
| Detection | Conductivity detector |
| Flow Rate (ml/min) | 0.7 |
| Eluent | 3.2 mM sodium carbonate 1.0 mM sodium hydrogen carbonate in a 5% acetone aqueous solution. |

Example 1—Preparation of crystalline mesylate Form 1 of N-hydroxy 2-{6-[(6-fluoro-quinolin-2-ylmethyl)-amino]-3-aza-bicyclo[3.1.0]hex-3-yl}pyrimidine-5-carboxamide N-hydroxy 2-{6-[(6-fluoro-quinolin-2-ylmethyl)-amino]-3-aza-bicyclo[3.1.0]hex-3-yl}pyrimidine-5-carboxamide (500 mg) was weighed into a 20 ml vial and 35 vols (17.5 ml) of a selected solvent EtOH/water (9:1 v/v) was added. All samples appeared as suspensions and were stirred (500 rpm) at 50° C. Methanesulfonic acid (1.1 mole equivalent, 1.395 ml) was added as a 1 M stock solution in THF. The samples were all stirred for 1 hour at 50° C. before being cooled to 5° C. at 0.1° C./min. The samples were left to stir overnight at 5° C. Observations were made immediately after the salt addition and again once the solutions had cooled to 5° C.

Alternative Procedure 1

N-hydroxy 2-{6-[(6-fluoro-quinolin-2-ylmethyl)-amino]-3-aza-bicyclo[3.1.0]hex-3-yl}pyrimidine-5-carboxamide (100 g) was weighed into a 5 L flask and 1.5 L of ACN or EtOH was added. All samples appeared as suspensions and were stirred at 50° C. A 1.0 mole equivalent of methanesulfonic acid was added. The samples were all stirred for 1 hour at 50° C. before being cooled to 5° C. The samples were left to stir overnight at 5° C. The precipitated solid was collected by filtration to afford the crystalline mesylate Form 1 of N-hydroxy 2-{6-[(6-fluoro-quinolin-2-ylmethyl)-amino]-3-aza-bicyclo[3.1.0]hex-3-yl}pyrimidine-5-carboxamide at 85% yield.

Example 2—Characterization of Crystalline Mesylate Form 1 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 1 was successfully scaled up and XRPD confirmed good crystallinity and the material was characterized, the results of which are shown in Table 5 below.

TABLE 5

| Solvent/method | EtOH/water, cooling |
| --- | --- |
| XRPD | Mesylate Form 1, no change on drying |
| ¹H-NMR | Consistent with structure, peak shifts, methanesulfonic acid (approximately 1 mole eq, mono salt, overlaps with API), 0.01 mol. Eq. residual EtOH detected |
| HPLC purity | 99.5% |
| TGA | No weight loss prior to degradation at 220° C. |
| DSC | Large exotherm affiliated with decomposition (onset temp. 222.1° C., 433 J/g) |
| IC | 1 mol. Eq. mesylate |
| 7 days at 40° C./75% RH | No change, Mesylate Form 1 |

TABLE 5-continued

| Solvent/method | EtOH/water, cooling |
|---|---|
| 14 weeks at 40° C./75% RH | Mixture of Mesylate Form 1 and Mesylate Form 2 (94.7% purity) |
| 7 days at 25° C./97% RH | No change, Mesylate Form 1 |
| 14 weeks at 25° C./97% RH | Mesylate Form 1 (93.5% purity) |
| GVS | Appeared stable by GVS, no hysteresis, and 0.35% reversible uptake from 0-90% RH: Slightly hygroscopic. XRPD remains unchanged |
| KF | 0.1% water content |
| form | Small crystalline rods ca. 20-50 μm |

The API acid stoichiometry was determined as 1:1 by $^1$H-NMR and 0.01 mole eq. EtOH was identified. The retention of the parent structure was also confirmed by NMR following salt formation. The material was isolated in good purity at 99.5% by HPLC. The crystal habit for the mesylate salt was defined as small crystalline rods which were ca. 20-50 μm in size.

There were no thermal events observed in the TGA thermogram until the onset of decomposition from ca. 220° C. The DSC was characterized by a single exothermic event with an onset temperature at 222.1° C. (433 J/g) associated with the decomposition event by TGA.

Mesylate Form 1 appeared to be stable under variable humidity environments. The material was slightly hygroscopic by GVS with ~0.35% reversible water uptake between 0-90% RH and the residue on recovery showed no change by XRPD. Mesylate Form 1 was unchanged by XRPD after 7 days at 25° C./97% RH and 40° C./75% RH and no significant drop in purity was noted.

Mesylate Form 1 is a crystalline non-solvated mesylate mono-salt that is a slightly hygroscopic and displayed stability up to 7 days under static stability conditions (25° C./97% RH, 40° C./75% RH).

Example 2a—XRPD Characterization of Crystalline Mesylate Form 1 of N-hydroxy 2-{6-[(6-fluoro-quinolin-2-ylmethyl)-amino]-3-aza-bicyclo[3.1.0]hex-3-yl}pyrimidine-5-carboxamide The peak table and XRPD for Mesylate Form 1 can be found below (Table 6, FIG. 1). The values for 2Θ are considered to have an error of ±0.3 degrees.

TABLE 6

| Angle (2θ°) | Intensity % |
|---|---|
| 3.7 | 100.0 |
| 7.5 | 31.9 |
| 13.3 | 1.4 |
| 14.9 | 57.4 |
| 15.4 | 2.7 |
| 15.7 | 1.4 |
| 16.1 | 2.7 |
| 16.7 | 9.4 |
| 16.8 | 3.8 |
| 17.3 | 13.5 |
| 17.7 | 1.4 |
| 18.0 | 2.3 |
| 18.4 | 4.0 |
| 18.7 | 5.7 |
| 19.5 | 2.3 |
| 19.7 | 13.0 |
| 20.3 | 3.9 |
| 21.0 | 4.2 |
| 22.5 | 15.2 |
| 22.9 | 14.1 |
| 23.1 | 8.1 |
| 23.4 | 11.2 |
| 24.0 | 5.2 |
| 24.2 | 5.6 |
| 24.6 | 2.3 |
| 24.8 | 2.8 |
| 25.3 | 8.6 |
| 25.6 | 1.9 |
| 26.4 | 2.5 |
| 26.8 | 4.6 |
| 27.2 | 1.3 |
| 28.3 | 2.4 |
| 28.6 | 2.5 |
| 29.5 | 2.5 |
| 30.1 | 17.3 |

Example 2b—Intrinsic Dissolution Rate of Crystalline Mesylate Form 1 of N-hydroxy 2-{6-[(6-fluoro-quinolin-2-ylmethyl)-amino]-3-aza-bicyclo[3.1.0]hex-3-yl}pyrimidine-5-carboxamide Aqueous solubility was determined by suspending sufficient compound in 0.5 ml deionized water to give a maximum final concentration of 40 mg/mi of the parent free-form of the compound. The suspension was equilibrated at 25° C., on a Heidolph plate shaker set to 750 rpm for 24 hours. After equilibration, the appearance was noted and the pH of the saturated solution was measured. Samples forming suspensions were centrifuged for 4 min at 13,500 rpm. Samples were then filtered through a glass fiber C filter (particle retention 1.2 μm), before dilution with $H_2O$ as appropriate.

Quantitation was by HPLC (see Table 2 for parameters) with reference to a standard solution of approximately 0.15 mg/ml in DMSO. Different volumes of the standard, diluted and undiluted sample solutions were injected. The solubility was calculated using the peak areas determined by integration of the peak found at the same retention time as the principal peak in the standard injection. Analysis was performed on an AgilentHPl 100/Infinity II 1260 series system equipped with a diode array detector and using OpenLAB software.

TABLE 7

| Parameter | Value | | |
|---|---|---|---|
| Type of method | Reverse phase with gradient elution | | |
| Column | Phenomenex Luna, C18 (2) 5 μm 50 × 4.6 mm | | |
| Column Temperature (° C.) | 25 | | |
| Standard Injections (μl) | 1, 2, 3, 4, 5, 7 | | |
| Test Injections (μl) | 1, 2, 3, 10, 15, 20 | | |
| Detection: Wavelength, Bandwidth (nm) | 260, 90 | | |
| Flow Rate (ml/min) | 2 | | |
| Phase A | 0.1% TFA in water | | |
| Phase B | 0.085% TFA in acetonitrile | | |
| | Time (min) | % Phase A | % Phase B |
| Timetable | 0.0 | 95 | 5 |
| | 1.0 | 80 | 20 |
| | 2.3 | 5 | 95 |
| | 3.3 | 5 | 95 |
| | 3.5 | 95 | 5 |
| | 4.4 | 95 | 5 |

Thermodynamic aqueous solubility of mesylate and free base forms are significantly different, as shown in Table 8. Free base is essentially insoluble in water. The mesylate shows excellent solubility at 40 mg/mL and the final pH of saturated solution was ~3.2.

The intrinsic dissolution rates (TDR) for the Mesylate Form 1 salt was determined in Fasted State Simulated Gastric Fluid FaSSGF media and compared with both Free Form A and Free Form B of N-hydroxy 2-{6-[(6-fluoro-quinolin-2-ylmethyl)-amino]-3-aza-bicyclo[3.1.0]hex-3-yl}pyrimidine-5-carboxamide. The IDR were not determined in Fasted State Simulated Intestinal Fluid (FaSSIF) or Fed State Simulated Intestinal Fluid (FeSSIF) media after a low absorbance values were noted for the parent free form compound that did not allow for complete data analysis. The Mesylate Form 1 salt exhibited a high IDR with an intrinsic dissolution rate of 9.1 mg/min/cm$^2$ (ca 8 times of free base form A) and the majority of the disc disintegrated in this media.

TABLE 8

Solubility and intrinsic dissolution rates in water or FaSSGF for salt forms and free form polymorphs

| Form | Solubility in water mg/mL (pH of saturated solution) | IDR (mg/min/cm$^2$) in FaSSGF |
|---|---|---|
| Free Base Form A | 0.001 (pH = 7.4) | 1.1 |
| Free Base Form B | 0.001 (pH = 7.4) | 1.8 |
| Mesylate Form 1 | 40 (pH = 3.2) | 9.1 |

FIG. 1 shows the X-ray powder diffractogram of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Figure 2:
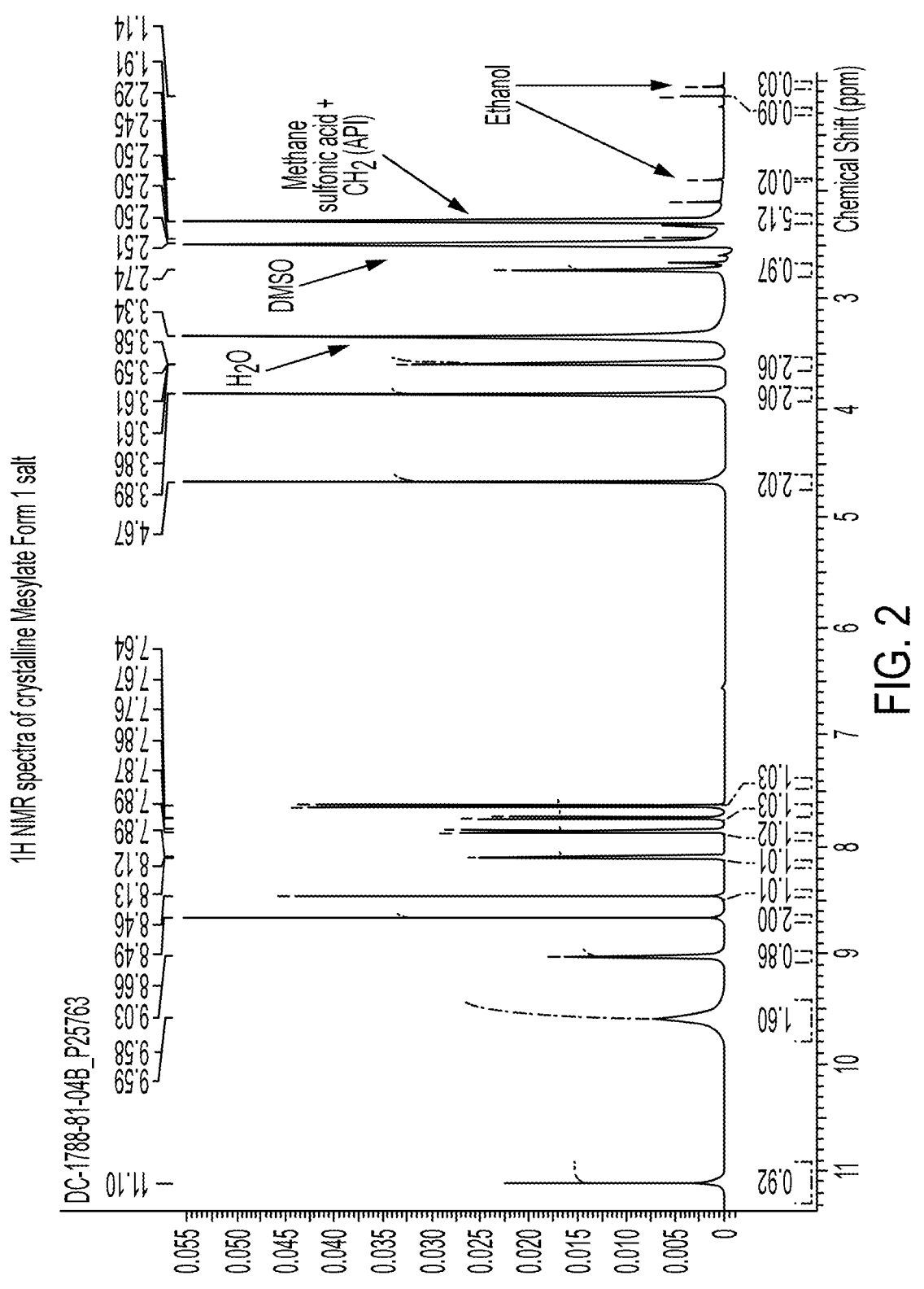

FIG. 2 shows the $^1$H NMR spectra of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 3 shows the thermal gravimetric analysis pattern of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Figure 4:
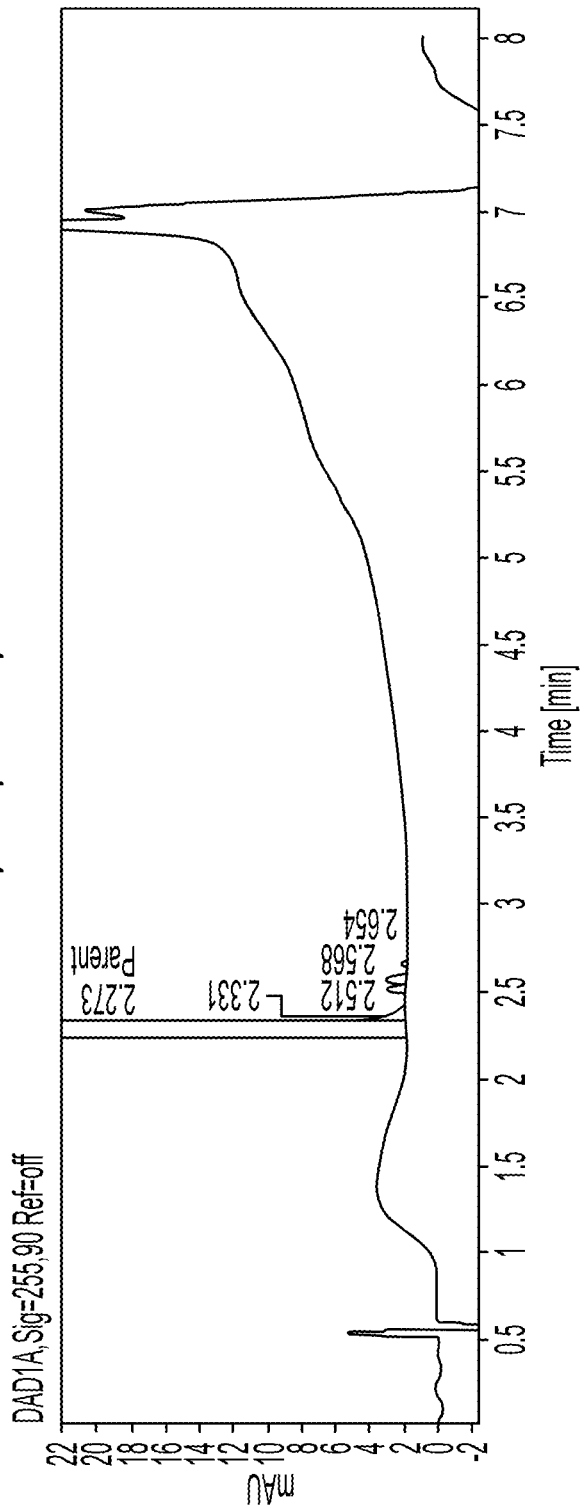
FIG. 4 shows the HPLC analysis of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 4 shows the HPLC analysis of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Figure 5:
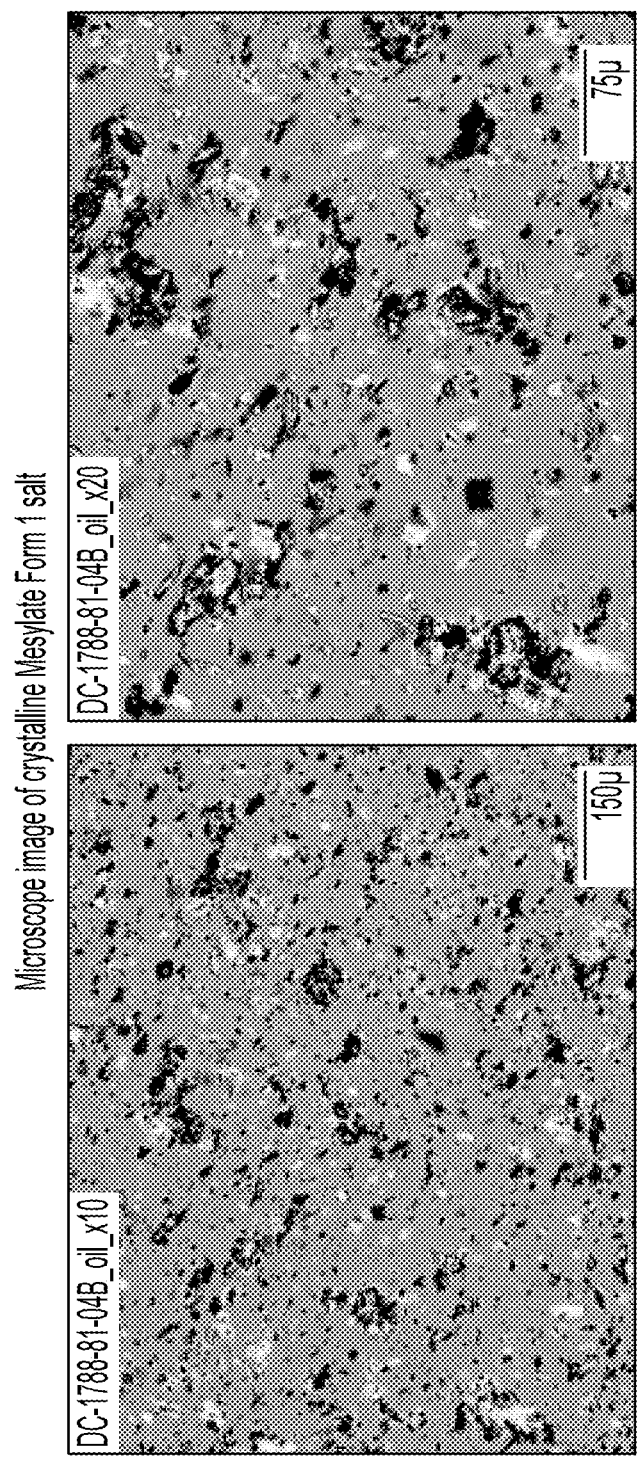
FIG. 5 shows the microscope image of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 5 shows the microscope image of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Figure 6:
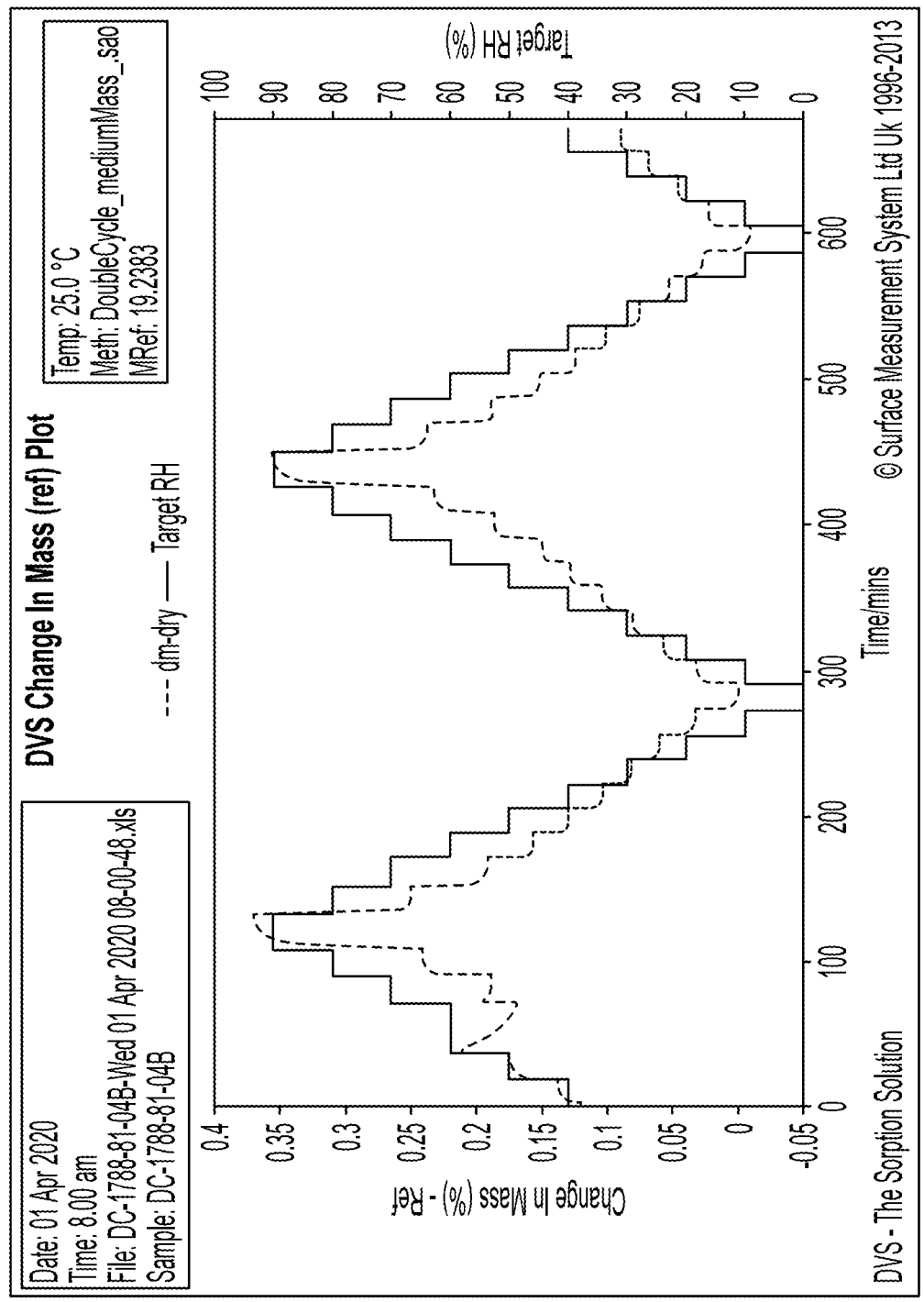
FIG. 6 shows the GVS kinetic plot of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 6 shows the GVS kinetic plot of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Figure 7:
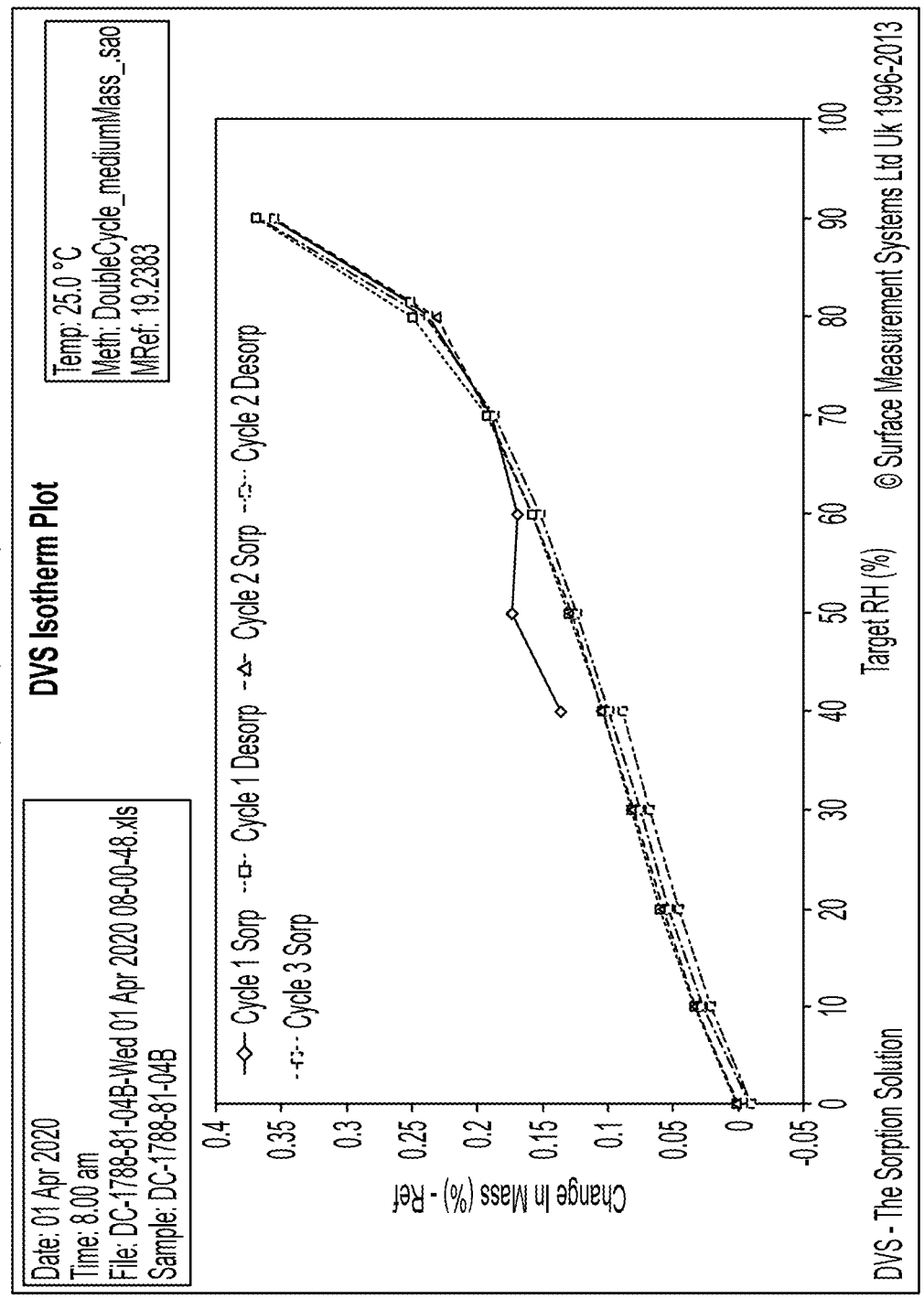
FIG. 7 shows the GVS isotherm plot of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 7 shows the GVS isotherm plot of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide.

Figure 8:
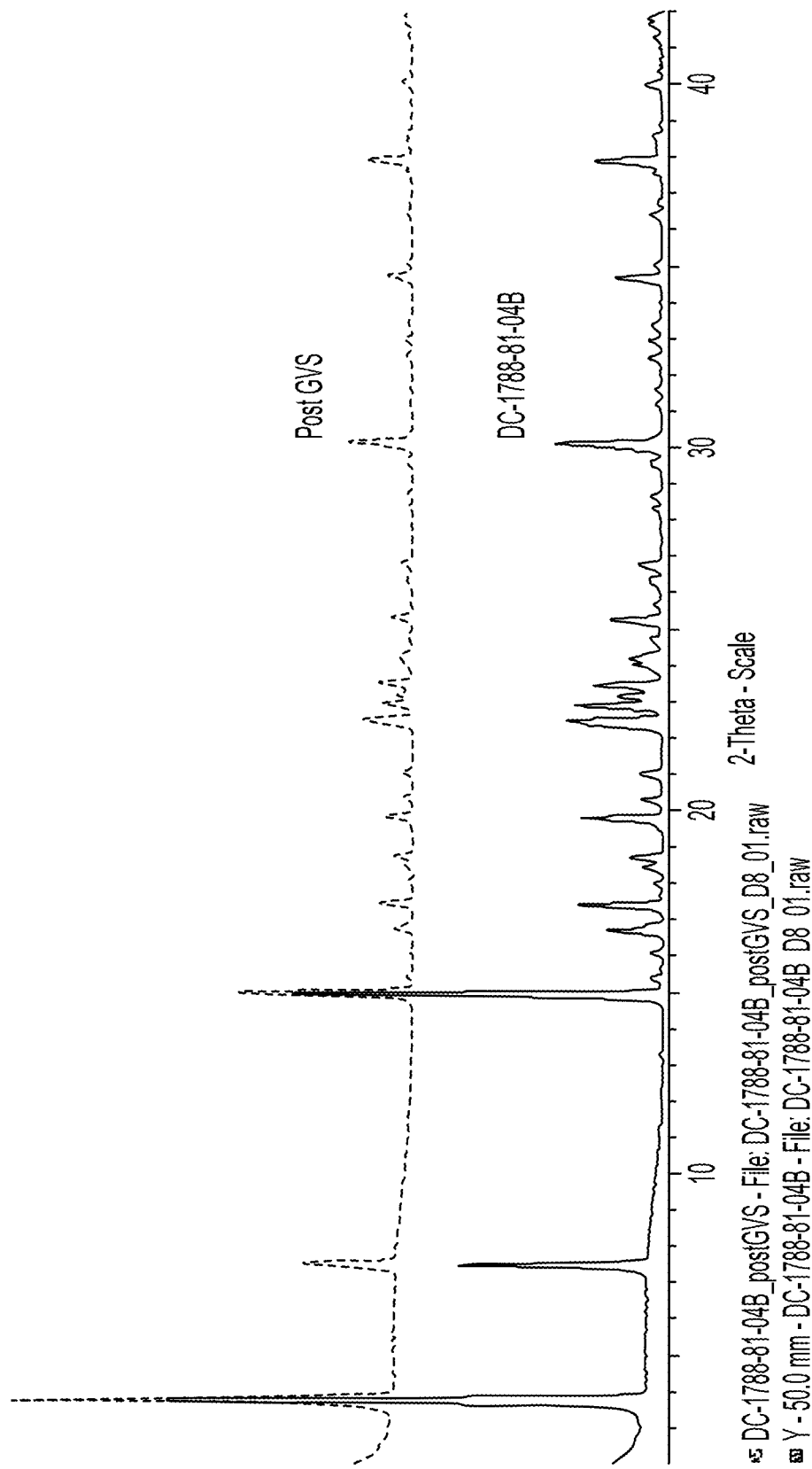
FIG. 8 shows the X-ray powder diffractogram of crystalline mesylate Form 1 salt after GVS analysis of N-hydroxy 2-{6-[(6-fluoro-quinolin-2-ylmethyl)-amino]-3-aza-bicyclo[3.1.0]hex-3-yl}pyrimidine-5-carboxamide.

FIG. 8 shows the X-ray powder diffractogram of crystalline mesylate Form 1 salt after GVS analysis of N-hydroxy 2-{6-[(6-fluoro-quinolin-2-ylmethyl)-amino]-3-aza-bicyclo[3.1.0]hex-3-yl}pyrimidine-5-carboxamide.

Figure 9:
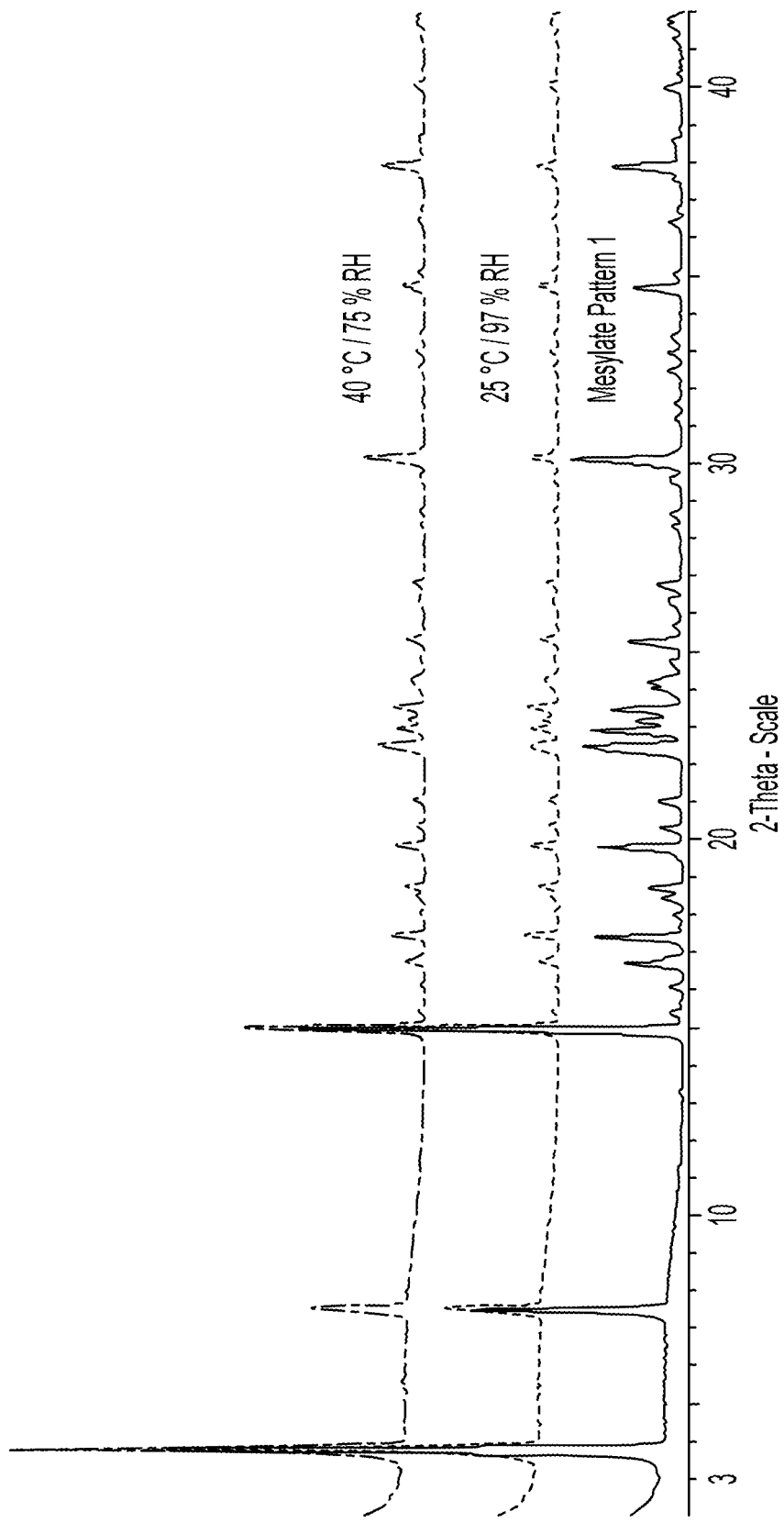
FIG. 9 shows the X-ray powder diffractogram of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide after storage under the indicated conditions.

FIG. 9 shows the X-ray powder diffractogram of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide after storage under the indicated conditions.

FIG. 10 shows the HPLC analysis of crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide after storage under the indicated conditions.

Example 3—Characterization of Amorphous Mesylate of N-hydroxy 2-{6-[(6-fluoro-quinolin-2-ylmethyl)-amino]-3-aza-bicyclo[3.1.0]hex-3-yl}pyrimidine-5-carboxamide Crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide (10 mg) was weighed into 4 HPLC vials. The relevant solvent (200 µl, 20 volumes) was added and the samples mixed on a vortex mixer to aid dissolution, observations were then made. If a clear, transparent solution was obtained, the solution was filtered using a 0.45 m PTFE membrane Acrodisc filter to remove any remaining solid particles. The solutions were then flash-frozen in an acetone/dry ice bath, and placed on the freeze dryer overnight. The next day, samples were removed from the freeze dryer, and analyzed by XRPD to confirm the amorphous solid state. The sample was further analyzed by mDSC and $^1$H NMR to determine residual solvent content and identify the glass transition of the amorphous solid. The results can be found in Table 9. The NMR identified 0.07 mol. eq. residual THF and the modulated DSC identified a high glass transition temperature, Tg=126.7° C. The purity was not significantly impacted by the lyophilization process and the amorphous showed moderate stability up to 7 days at 25° C./97% RH and 40° C./75% RH with appearing largely amorphous with a small reflection appearing at 3.7° 2θ.

TABLE 9

Characterization of amorphous mesylate salt by lyophilization from THF/H$_2$O (1:1)

| | XRPD | Amorphous |
|---|---|---|
| | $^1$H-NMR | Residual THF (0.07 mol. eq.) |
| | mDSC* | T$_g$: 126.7° C. |
| | HPLC Purity | 97.7% |
| Static storage 1 week | 40° C./ 75% RH | Amorphous, with low-level peak at 3.7° 2θ |
| | 25° C./ 97% RH | Amorphous, with low-level peak at 3.7° 2θ |

Figure 11:
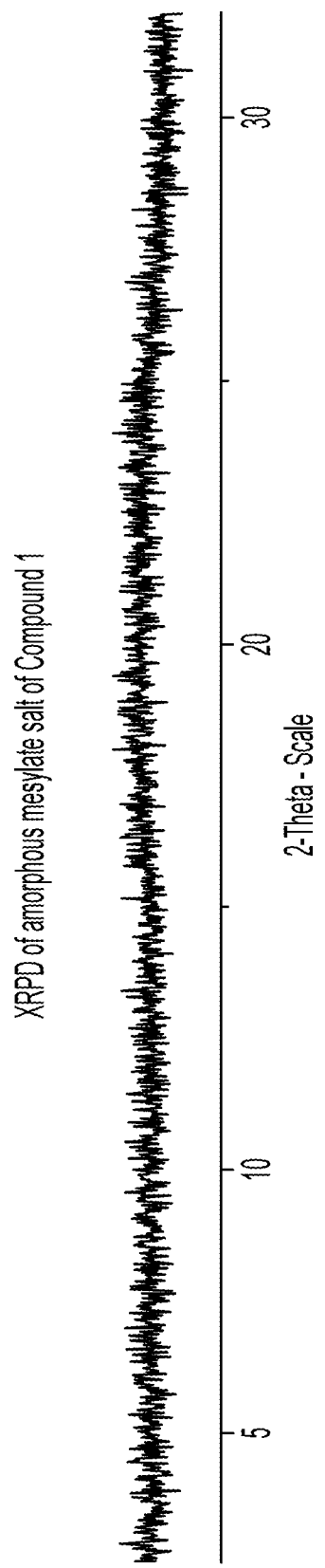
FIG. 11 shows the X-ray powder diffractogram of the amorphous mesylate salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 11 shows the X-ray powder diffractogram of the amorphous mesylate salt of N-hydroxy 2-{6-[(6-fluoro-quinolin-2-ylmethyl)-amino]-3-aza-bicyclo[3.1.0]hex-3-yl}pyrimidine-5-carboxamide.

Figure 12:
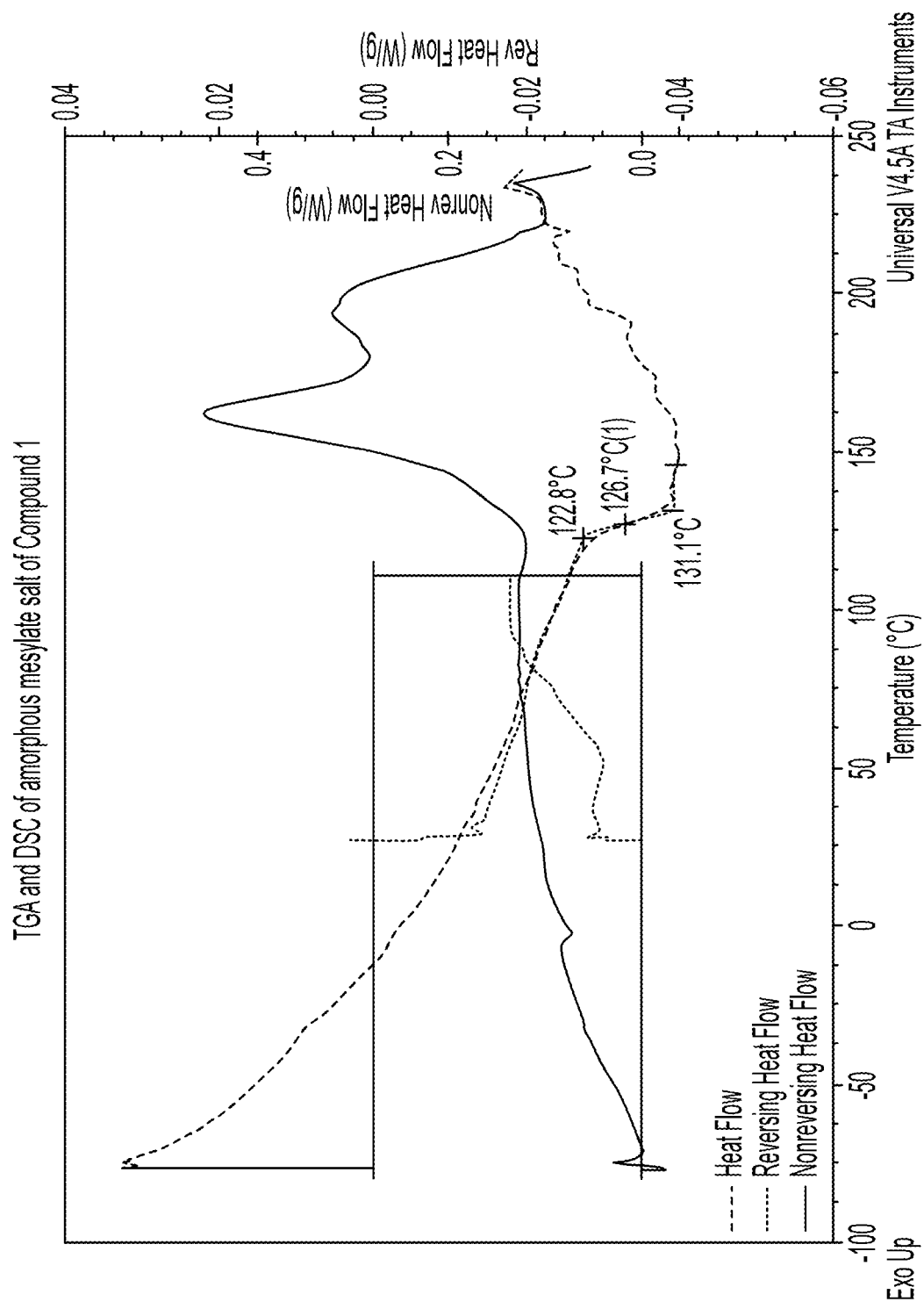
FIG. 12 shows the TGA and DSC pattern of the amorphous mesylate salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 12 shows the TGA and DSC pattern of the amorphous mesylate salt of N-hydroxy 2-{6-[(6-fluoro-quinolin-2-ylmethyl)-amino]-3-aza-bicyclo[3.1.0]hex-3-yl}pyrimidine-5-carboxamide.

Example 4—Characterization of Crystalline Mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 1 (400 mg) was placed in a 100 ml round-bottomed flask. To it was added THF/water (9:1 v/v) (28 ml, 70 volumes) and the sample was stirred at 50° C. The sample was partially soluble, and the temperature increased to 60° C. A white precipitate was observed, the amount of which seemed to increase with increased temperature/further dissolution of the initial solid. An aliquot was taken of the suspension, placed on a flat XRPD holder, and allowed to dry, to leave behind a thin residue. This was then analyzed by XRPD and found to be amorphous.

The sample was then heated to 70° C., where the solution remained turbid. The suspension was cooled again to 60° C., where an additional 1 ml was added, followed by further 1 ml aliquots added until an additional 9 ml had been added (total solvent: 38 ml, 95 volumes). The solution remained turbid and the temperature was again increased to 70° C., where a clear, colorless solution was obtained. The solution was cooled to 5° C. at 0.1° C./minute with stirring overnight.

The next morning, a thin suspension was observed. A small aliquot was taken and allowed to dry on a flat XRPD holder. The sample was observed to dry to a glass-like appearance, the solid was collected and flattened for analysis by XRPD. The sample appeared amorphous, with low-level crystalline peaks. The sample was stirred at 5° C. for a further two days, after which another aliquot was taken, and allowed to dry on a flat XRPD holder. The sample was isolated on a Buchner funnel with drying for ~5 minutes to afford Mesylate Form 2.

TABLE 10

| Characterization of Mesylate Form 2 | |
|---|---|
| Solvent | 10% H$_2$O/THF |
| XRPD | Mesylate Form 2 |
| $^1$H-NMR | Consistent with structure. Mesylate present (~0.9 mol. eq. - overlapping peaks with API CH$_2$). Residual THF (0.008 mol. eq., 0.1% w/w) |
| HPLC Purity | 99.5% |
| DSC | Broad endotherm, onset 124.7° C. (240 J/g), two small exotherms with onset at 155.4° C. (2 J/g) and 171.4° C. (2 J/g) |
| TGA | 3.7% mass loss ambient - 170° C. furthermass loss >170° C. |
| 40° C./75% RH | Mesylate Form 2, 99.5% purity |
| 25° C./97% RH | Mesylate Form 2, 99.5% purity |
| KF | 3.6% water (1 mol. eq.) |
| IC | 17.7% mesylate (0.9 mol. eq.) |
| GVS | ~0.4% reversible water uptake between 0-90% RH XRPD Post-GVS: Mesylate Form 2 |
| SEM | Large agglomerates (<200 µm in size) comprised of irregular-shaped primary particles (≤10 µm in size) |
| PLM | Large agglomerates observed (~200 µm in size), smaller particles/agglomerates observed (~100 µm). Smaller, individual particles too small to be observed. |
| Assignment | Monohydrate |

The $^1$H NMR was consistent with the structure, containing ~0.9 mol. eq. mesylate, and there was low residual THF (0.008 mol. eq.). The IC analysis confirmed 0.9 mol. eq. Mesylate to be present. There was a 3.7% mass loss ambient—170° C. by TGA which was confirmed as water where KF identified 3.6% water (equating to 1 mol. Eq. water). The DSC thermogram showed a broad endotherm with onset at 124.7° C., which overlapped with the water loss, and was followed by two small exotherms with onsets at 155.4° C. and 171.4° C. From GVS analysis, Mesylate Form 2 was slightly hygroscopic, with ~0.4% reversible water uptake between 0-90% RH and the hydrate appears to be relatively stable as the 1 mol. eq. of bound water was not lost during the desorption cycles. This was supported by the XRPD post-GVS being unchanged as Mesylate Form 2 to remain.

After storage at 25° C./97% RH and 40° C./75% RH) for 1 week the form was unchanged by XRPD with no significant drop in HPLC purity noted. Analysis of particle size and morphology by microscopy showed the presence of agglomerates of ~200 µm in size, comprised of primary irregular-shaped particles (≤10 µm) in size. HPLC showed a purity of 99.5%. In summary Mesylate Form 2 is a crystalline monohydrate mono-mesylate salt that is slightly hygroscopic.

Example 4a—XRPD Characterization of Crystalline Mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide The peak table for Mesylate Form 2 and XRPD for the sample can be found below (Table 11, FIG. 14). The values for 2θ are considered to have an error of 1.3 degrees.

TABLE 11

| XRPD peak table for Mesylate Form 2 | | | |
|---|---|---|---|
| Angle (°2θ) | Intensity % | Angle (°2θ) | Intensity % |
| 7.3 | 27.5 | 25.0 | 19.9 |
| 12.4 | 6.2 | 26.3 | 29.4 |
| 14.6 | 100.0 | 26.9 | 83.1 |
| 14.8 | 51.3 | 27.7 | 28.6 |
| 15.6 | 13.1 | 28.4 | 26.1 |
| 16.4 | 47.4 | 28.6 | 17.8 |
| 17.4 | 38.1 | 29.4 | 22.8 |
| 18.4 | 53.2 | 29.7 | 13.8 |
| 19.2 | 19.1 | 31.0 | 9.9 |
| 19.5 | 57.9 | 31.5 | 4.9 |
| 20.5 | 39.7 | 32.9 | 12.4 |
| 20.7 | 28.5 | 33.1 | 7.9 |
| 21.2 | 20.2 | 34.6 | 21.6 |
| 21.9 | 44.1 | 35.4 | 21.4 |
| 22.2 | 23.2 | 36.9 | 27.2 |
| 22.5 | 4.9 | 38.5 | 8.5 |
| 23.5 | 38.3 | 39.0 | 5.7 |
| 23.8 | 9.7 | 39.7 | 6.6 |
| 24.1 | 22.0 | 41.2 | 6.9 |
| 24.3 | 98.8 | 41.8 | 24.6 |

FIG. 13 shows the XRPD of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

FIG. 14 shows the TGA and DSC of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

Figure 15:
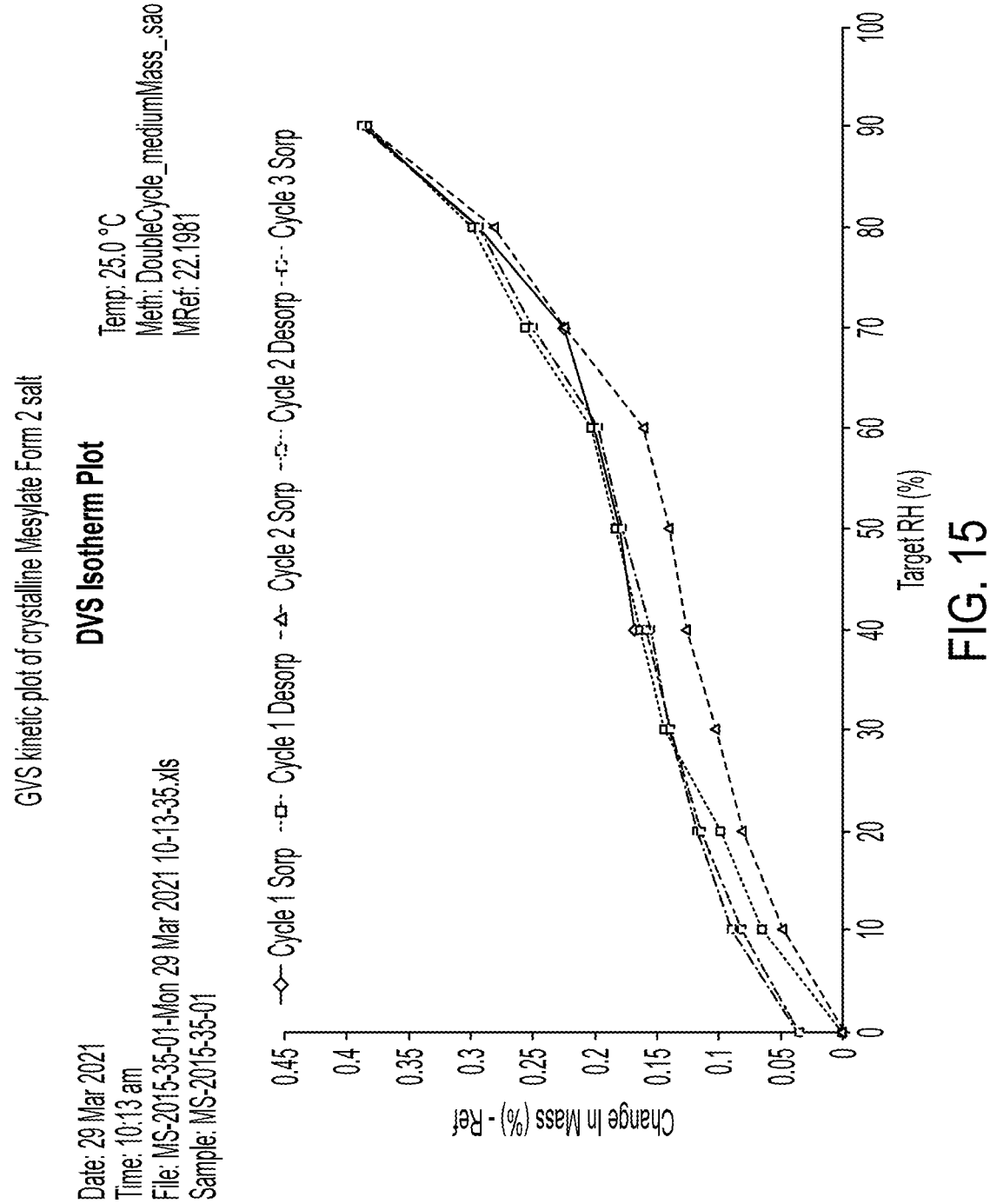
FIG. 15 shows the GVS kinetic plot of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

FIG. 15 shows the GVS kinetic plot of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

Figure 16:
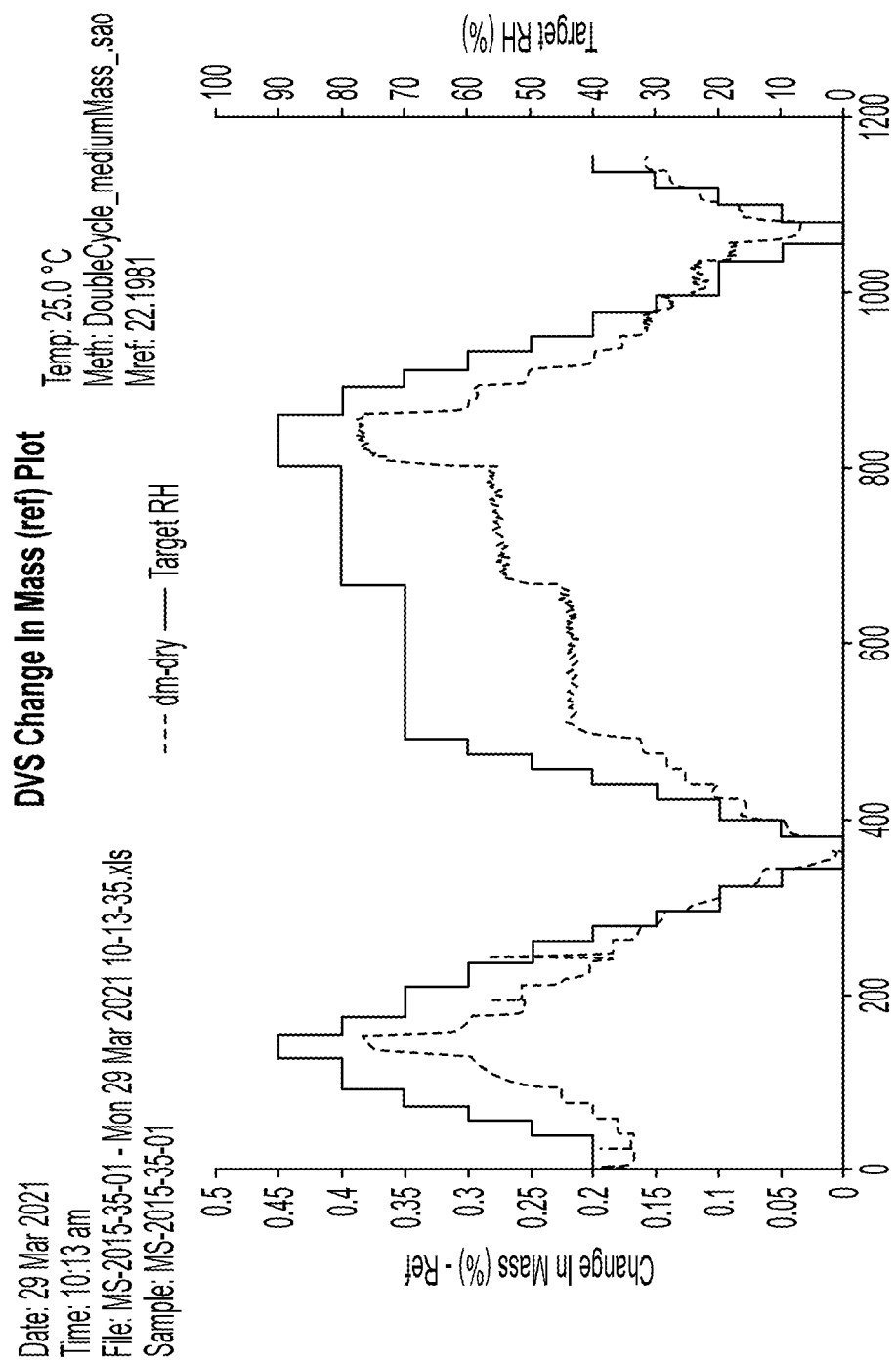
FIG. 16 shows the GVS isotherm plot of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

FIG. 16 shows the GVS isotherm plot of crystalline mesylate Form 2 of N-hydroxy 2-{6-[(6-fluoro-quinolin-2-ylmethyl)-amino]-3-aza-bicyclo[3.1.0]hex-3-yl}pyrimidine-5-carboxamide.

Example 5—Characterization of Crystalline Mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 1 was dissolved in H$_2$O (15 ml, ~20 volumes) in a 20 ml scintillation vial at 50° C. to produce a clear, transparent solution. Undissolved particulates were observed (possible fibers from filter paper), and so the solution was filtered through an acrodisc filter (0.45 µm pore size). The sample was cooled to 5° C. at 0.1° C./minute and stirred at 5° C. overnight. The next day, the sample was observed to be a clear, transparent yellow solution, which turned turbid throughout the day. The next day, a peachy-colored thick suspension was observed. A small aliquot of the suspension was taken and analyzed by XRPD. The sample was isolated over gentle vacuum to remove excess water. The wet filter cake was air dried only. A small amount of the damp solid was then taken, which dried slightly on the holder prior to analysis by XRPD (indicated by color change from darker to lighter). The XRPD holder containing the aliquot taken from the suspension was re-analyzed after drying in air for ~2 hours.

Analysis of the aliquot taken from the suspension after being left to stir overnight showed it to be Mesylate Form 3, however, after leaving it to dry for ~2 hour on the XRPD holder it was shown to have become poorly crystalline. This behavior suggested that Mesylate Form 3 was likely to be a metastable hydrate. Identifying that excessive drying reduced the crystallinity resulted in the gentle isolation and air dying only of the bulk sample which successfully provided crystalline Mesylate Form 3 as summarized in Table 12.

TABLE 12

Characterization of Mesylate Form 3

| | |
|---|---|
| Solvent | Water |
| XRPD | Mesylate Form 3 |
| $^1$H-NMR | Consistent with structure |
| | 1 mol. eq. mesylate present |
| | (overlapping peaks with API $CH_2$) |
| HPLC Purity | 96.5% |
| DSC | Complex thermogram with an endotherm with |
| | onset at 48.2° C. (62 J/g), followed by additional |
| | event behavior up to a sharp endotherm, onset: |
| | 113.0° C. (59 J/g). |
| TGA | 28.8% mass loss from ambient to 135° C. |
| | Additional mass loss observed >205° C. |
| 40° C./75% RH | Mesylate Form 5, 97.0% purity |
| 25° C./97% RH | Mesylate Form 3, 96.6% purity |
| KF | 46.6% water (19.1 mol. eq.)* |
| IC | 13.2% mesylate (0.9 mol. eq.) assuming |
| | 9 water molecules |
| GVS | Sorption 1 cycle: starting at 25.1% |
| | water content at 40% RH and has 2% |
| | water uptake up to 90% RH |
| | Desorption Cycle 1 22% |
| | water loss from 30-20% RH |
| | Sorption/desorption cycle 2~12% water |
| | uptake from 0-90% RH with |
| | hysteresis between 0-60% RH. |
| | XRPD Post-GVS: Poorly crystalline broad |
| | reflections may match Mesylate Form 1 |
| SEM | Agglomerates (>200 μm) comprised of |
| | microcrystalline particles (laths, <1-6 μm in |
| | size - longest length, primary particle size). |
| PLM | Large agglomerates observed (~200 μm) consisting |
| | of smaller particles also observed (<10 μm) |
| Assignment | Metastable nonahydrate |

Mesylate Form 3 was isolated in good crystallinity and there was a drop in purity to 96.5%. The $^1$H NMR remained consistent with the structure and 1 mol. eq. mesylate identified present. IC analysis confirmed there to be 0.9 Mol. eq. mesylate (assuming 9 water molecules in the mass calculation. The TGA thermogram had a 28.8% mass loss ambient to 135° C. This was suspected to be bound water and potentially some residual surface water from the gentle sample drying. The Karl Fisher confirmed water was present with 46.6% water content. It is plausible the difference with respect to the TGA was due to the time difference between the analyses which could have resulted in the sample drying to a more stable level of water content. The DSC thermogram was complex displaying a broad endotherm with onset at 48.2° C. followed by a modulating baseline that was likely due to other thermal behavior. This was followed by sharp endotherm with an onset at 113.0° C.

The GVS analysis was critical in determining the nature of Mesylate Form 3. At the start of the GVS experiment at 40% RH the kinetic plot shows a loss of water mass until it stabilizes at 25.1% water content. Nine water molecules were calculated to be 23.5% w/w. the first sorption cycle from 40%-90% RH shows that 2% water uptake from the atmosphere occurs. The desorption cycle then loses incremental water down to 30% RH (to 24.30% water, close to ideal 9 mol. eq. water). The further drop in humidity to 20% RH is where the majority of this water is then lost which then further drops to down to 0% RH. The second sorption profile is different with ~12% water uptake observed between 0-90% RH which is lost on the desorption cycle. The final sorption cycle up to 40% RH looks similar to sorption cycle 2 and suggests a hysteresis between 0-60% RH. The XRPD post-GVS was poorly crystalline with broad reflections that didn't match well with any of the known hydrates and has some reflection in common which may match Mesylate Form 1. From the combination of TGA, KF and GVS data Mesylate Form 3 is assigned as a nonahydrate (nine water molecules).

Mesylate Form 3 remained unchanged by XRPD when placed under static storage for 1 week at 25° C./97% RH showed conversion to Mesylate Form 5 at 40° C./75% RH again indicating some metastability to the form.

In summary, Mesylate Form 3 is assigned as a metastable nonahydrate of the mono-mesylate salt. The metastable nature of the form has been displayed through the drying processes on isolation, the different sorption profiles observed between the first and second cycle of the GVS (and post-GVS XRPD) and its conversion to the sesquihydrate Mesylate Form 5 after storage at 40° C./75% RH.

Example 5a—XRPD Characterization of Crystalline Mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide The peak table and XRPD for Mesylate Form 3 can be found below (Table 12, FIG. 17). The values for 2Θ are considered to have an error of ±0.3 degrees.

TABLE 12

XRPD peak table for Mesylate Form 3

| Angle (°2Θ) | Intensity % | Angle (°2Θ) | Intensity % |
|---|---|---|---|
| 6.3 | 24.3 | 23.8 | 6.5 |
| 8.4 | 9.5 | 24.2 | 8.3 |
| 9.5 | 100.0 | 24.8 | 27.0 |
| 10.3 | 50.4 | 25.4 | 9.6 |
| 13.0 | 1.9 | 25.8 | 10.4 |
| 13.4 | 2.7 | 26.2 | 12.4 |
| 14.8 | 28.6 | 26.7 | 10.3 |
| 15.4 | 3.4 | 27.2 | 16.6 |
| 15.8 | 10.1 | 27.5 | 12.4 |
| 16.5 | 19.7 | 27.9 | 5.6 |
| 16.8 | 14.6 | 28.3 | 5.7 |
| 17.4 | 2.8 | 28.6 | 7.5 |
| 18.7 | 11.5 | 29.4 | 8.4 |
| 19.0 | 15.9 | 29.8 | 7.6 |
| 19.4 | 49.2 | 30.5 | 9.3 |
| 20.7 | 11.9 | 31.3 | 9.2 |

TABLE 12-continued

XRPD peak table for Mesylate Form 3

| Angle (°2θ) | Intensity % | Angle (°2θ) | Intensity % |
|---|---|---|---|
| 21.3 | 8.3 | 31.8 | 14.8 |
| 21.6 | 11.8 | 32.5 | 8.6 |
| 22.5 | 12.3 | 32.8 | 9.2 |
| 22.8 | 7.0 | 33.3 | 13.4 |
| 23.3 | 24.3 | | |

FIG. 17 shows the XRPD of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

FIG. 18 shows the TGA and DSC of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

Figure 19:
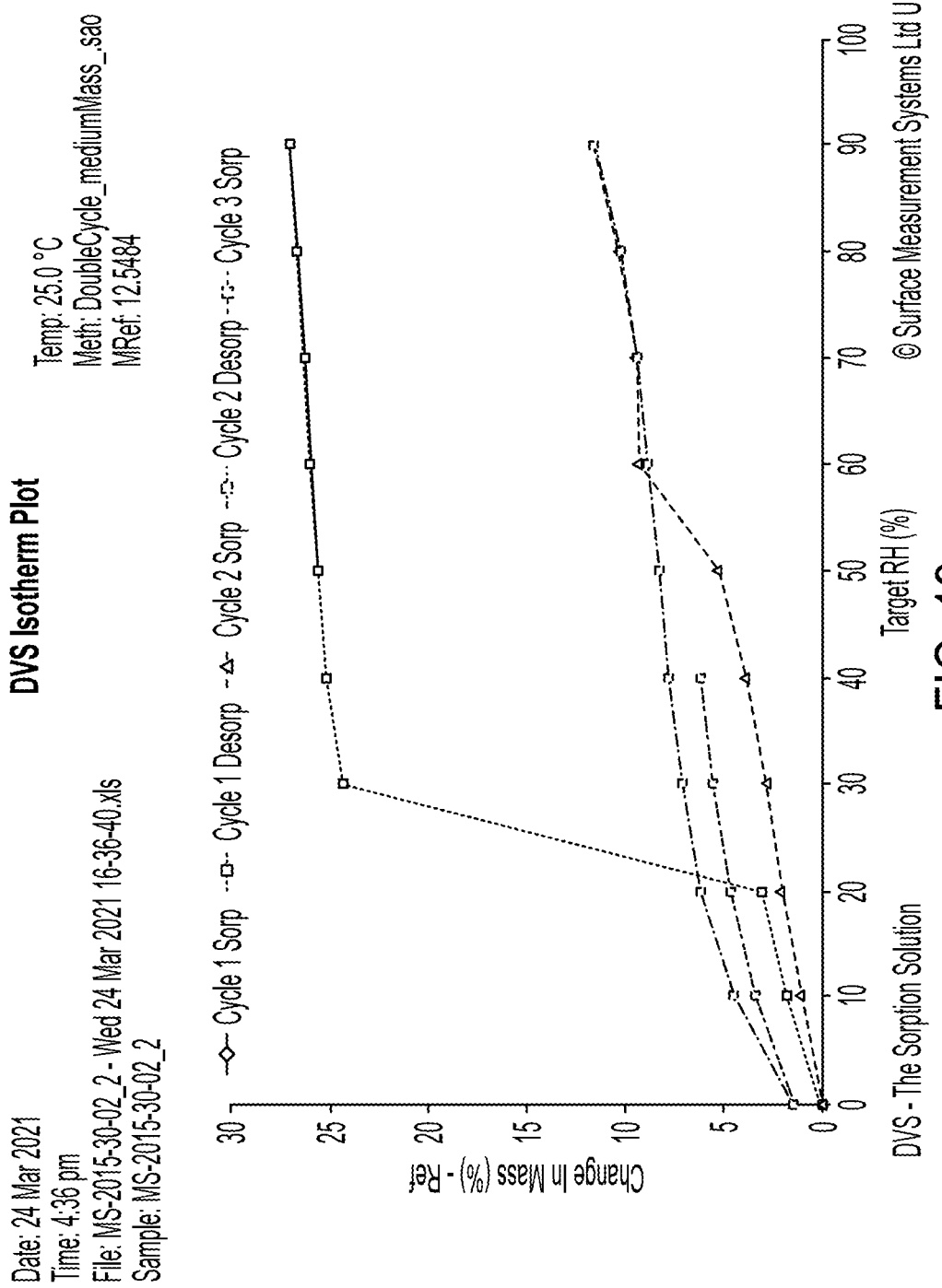
FIG. 19 shows the GVS kinetic plot of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

FIG. 19 shows the GVS kinetic plot of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

Figure 20:
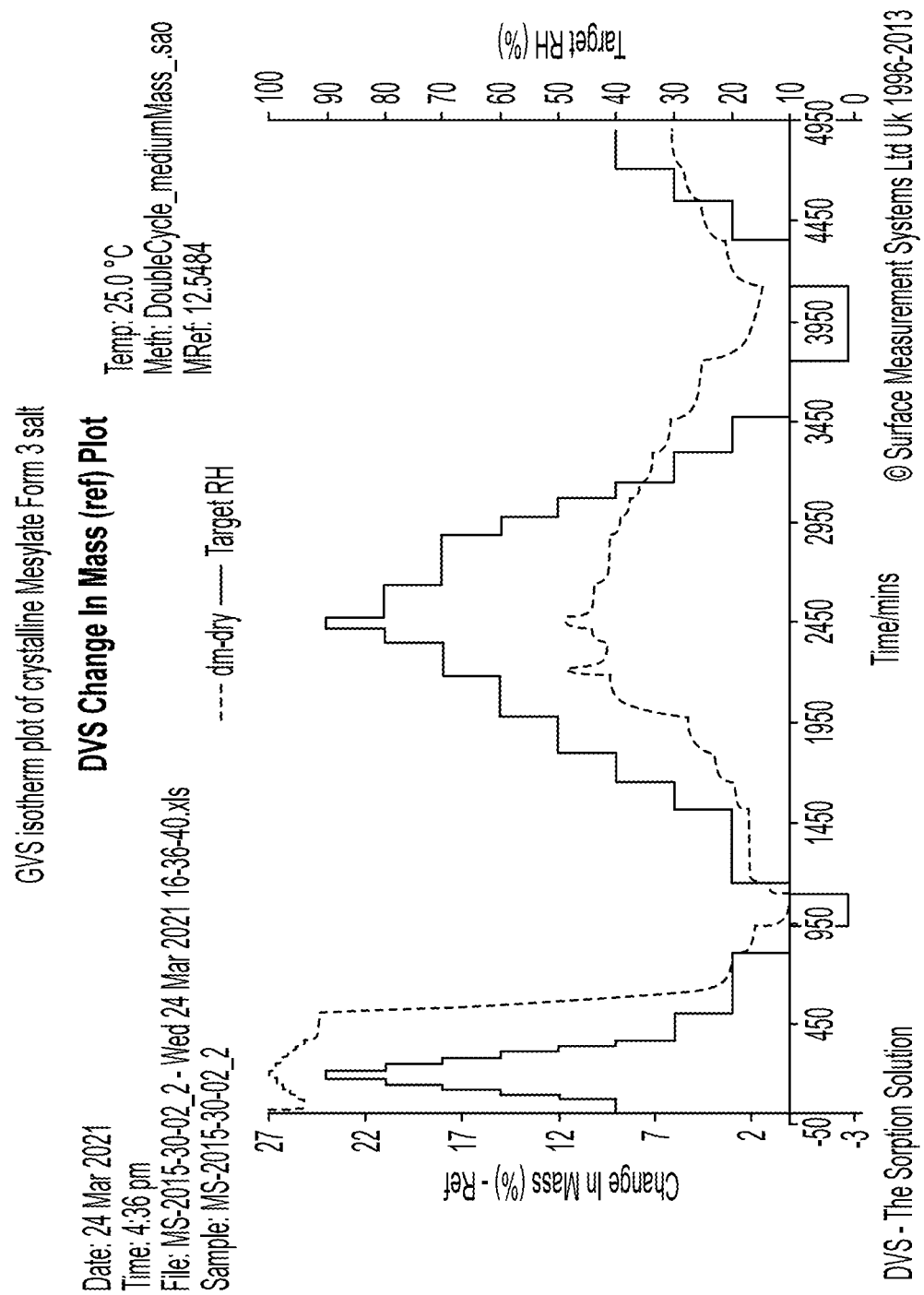
FIG. 20 shows the GVS isotherm plot of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

FIG. 20 shows the GVS isotherm plot of crystalline mesylate Form 3 of N-hydroxy 2-{6-[(6-fluoro-quinolin-2-ylmethyl)-amino]-3-aza-bicyclo[3.1.0]hex-3-yl}pyrimidine-5-carboxamide.

Example 6—Characterization of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide The amorphous mesylate salt was generated using lyophilization as described in Example 3. The amorphous solid (750 mg) was suspended in THF/water (9:1 v/v) (15 ml, 20 volumes) and stirred at 5° C. producing a white suspension. The suspension was stirred overnight at 5° C. and the next morning, an aliquot was taken, placed on a flat XRPD holder and analyzed by XRPD. The suspension was then isolated over a Buchner funnel and dried for ~15 minutes under vacuum. The solid was re-analyzed by XRPD post-isolation and drying.

TABLE 13

Characterization of Mesylate Form 4

| | |
|---|---|
| Solvent | 10% H₂O/THF |
| XRPD | Crystalline-Mesylate Form 4 |
| ¹H-NMR | Consistent with structure, (0.9 mol. eq. mesylate). THF signal not observed |
| HPLC purity | 99.3% |
| DSC | Overlapping endothermic event with onset 51.0° C. (269 J/g) No further events observed. |
| TGA | 9.6% mass loss ambient - 92° C. Furthermass loss above 200° C. |
| 40° C./75% RH | Mixture Mesylate Form 4 and Mesylate Form 1, 99.4% purity |
| 25° C./97% RH | Mesylate Form 1, 99.5% purity |
| KF | 12.6% water (3.2 mol. eq.)* |
| IC | 17% mesylate (1.0 mol. eq.) |
| GVS | Different behavior displayed on cycle 1 and cycle 2 Cycle 1: 9.4% starting water content, 0.7% water uptake from 40-90% RH, significant step loss from 20 to 10% RH on desorption Cycle 2: 3.6% water uptake between 0-90% RH displaying hysteresis loop Post-GVS: Converted to Mesylate Form 1 by XRPD |
| SEM | Large agglomerates observed ~600 μm in size, comprised of smaller lath-type particles~30 μm in size. Particles >5 μm present. |
| PLM | Large agglomerates observed ~600 μm in size, smaller particles present ~10 μm in size |
| Assignment | Metastable trihydrate |

The sample was isolated in good crystallinity with high purity at 99.3% by HPLC. The ¹H NMR confirmed there to be at least 0.9 mol. eq. mesylate and the ¹H-NMR spectrum was consistent with the structure. The TGA had a mass loss of 9.6% ambient to 92° C. which was suspected to be water die to the absence of residual THF. KF analysis showed 12.6% water (equating to ~ 4 mol. eq. water). The DSC displayed overlapping endothermic events with an onset at 51.0° C. and overlapped with the water loss event by TGA.

The GVS analysis showed different behaviors between cycle 1 and cycle 2. The starting water content at 40% RH was 9.4% water with an additional 0.7% water uptake in the first sorption cycle (40-90% RH). During the desorption cycle there was gradual water loss (0.8% water) down to 20% RH with a significant loss (~9% water content) between 20 to 10% RH. During the second cycle, a total water uptake of 3.6% is observed between 0-90% RH, with hysteresis observed between the sorption/desorption steps. The GVS data was in closer agreement to the TGA loss than the KF and the assessment was made that Mesylate Form 4 contained 3 mol. eq. water. The discrepancy with the KF may have been due to differences in sampling time when the sample may have had additional residual water from the initial isolation. The XRPD post-GVS showed conversion to Mesylate Form 1.

Mesylate Form 4 was unchanged by XRPD after static storage at 40° C./75% RH for 1 week with good purity of 99.4%. By contrast conversion to Mesylate Form 1 after storage at 25° C./97% RH was observed and retained a good purity of 99.5%. The microscopy analysis showed the presence of large agglomerates ~600 μm in size, comprised of smaller lath-type particles ~30 μm in size. Finer particles of 5-10 μm in size were also observed.

In summary, Mesylate Form 4 is a metastable trihydrate of the mono-mesylate salt as supported by the GVS and TGA analysis. Evidence of limited stability were displayed by conversion to Mesylate Form 1 post GVS analysis and after storage at 25° C./97% RH.

Example 6a—XRPD Characterization of Crystalline Mesylate Form 4 of N-hydroxy 2-{6-[(6-fluoro-quinolin-2-ylmethyl)-amino]-3-aza-bicyclo[3.1.0] hex-3-yl}pyrimidine-5-carboxamide The peak table and XRPD for Mesylate Form 4 can be found below (Table 14, FIG. 21). The values for 2Θ are considered to have an error of 0.3 degrees.

TABLE 14

XRPD peak table for Mesylate Form 4

| Angle (°2θ) | Intensity % |
|---|---|
| 3.5 | 100.0 |
| 6.9 | 10.8 |
| 10.3 | 55.7 |
| 13.8 | 10.2 |
| 15.2 | 15.2 |
| 16.5 | 6.8 |
| 17.2 | 39.8 |

TABLE 14-continued

XRPD peak table for Mesylate Form 4

| Angle (°2θ) | Intensity % |
|---|---|
| 17.7 | 36.5 |
| 18.8 | 5.4 |
| 19.1 | 8.9 |
| 20.6 | 10.9 |
| 21.9 | 9.3 |
| 22.4 | 25.5 |
| 23.0 | 7.2 |
| 23.5 | 17.8 |
| 24.2 | 10.7 |
| 24.7 | 25.7 |
| 25.1 | 9.0 |
| 25.5 | 10.1 |
| 26.4 | 23.7 |
| 27.4 | 9.0 |
| 28.0 | 7.0 |
| 28.9 | 5.9 |

FIG. 21 shows the XRPD of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

FIG. 22 shows the TGA and DSC of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

Figure 23:
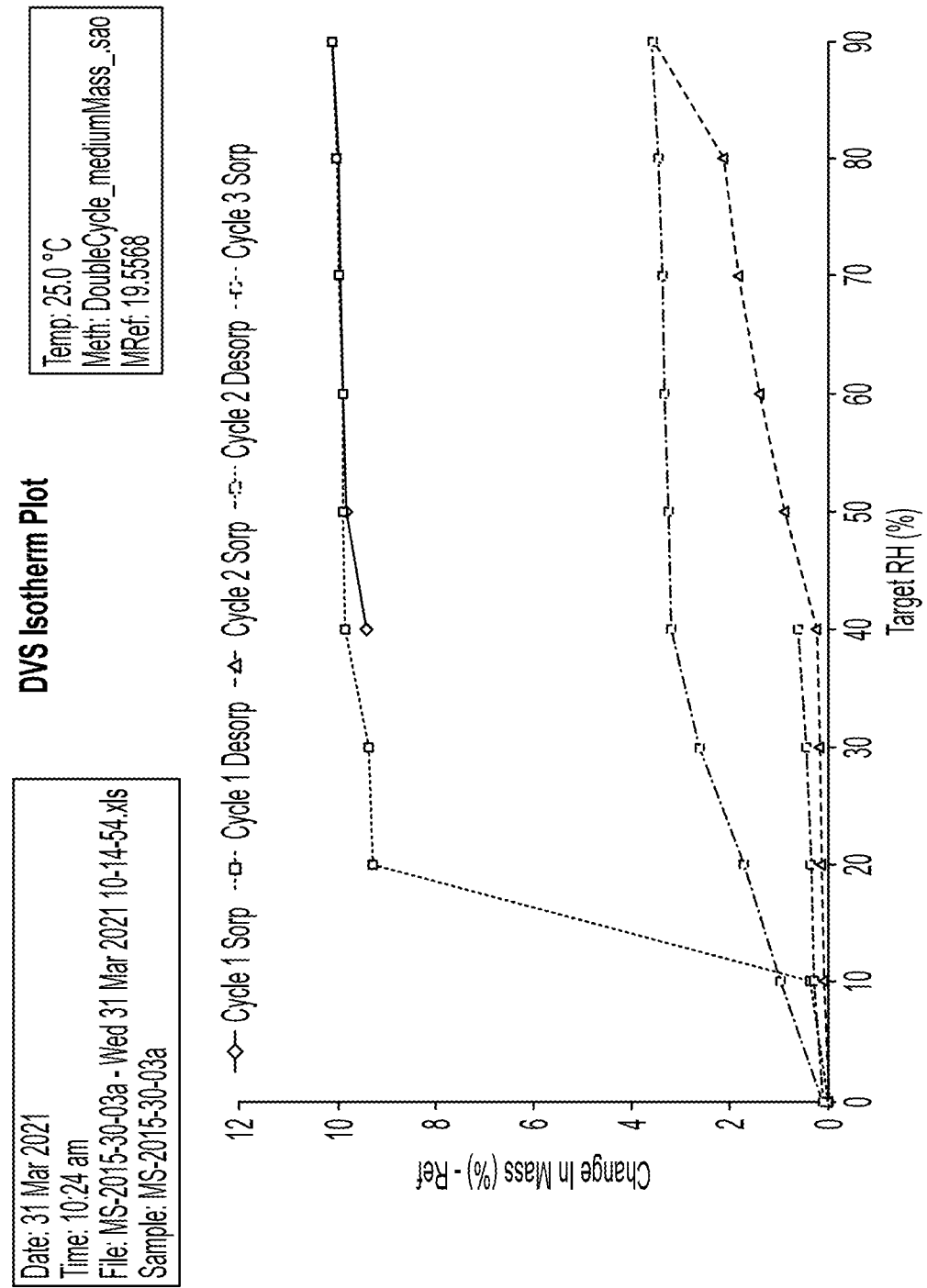
FIG. 23 shows the GVS kinetic plot of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

FIG. 23 shows the GVS kinetic plot of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

Figure 24:
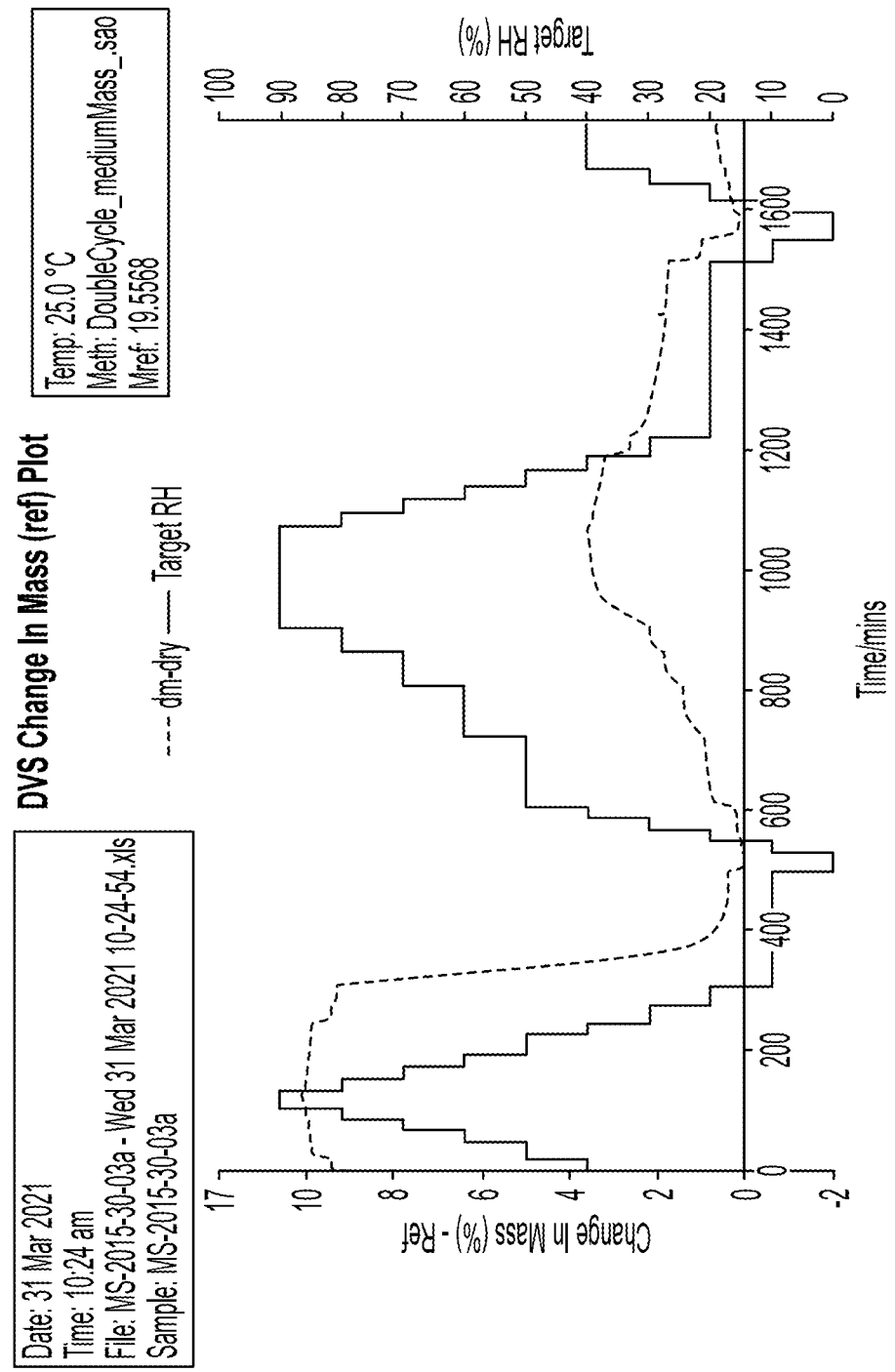
FIG. 24 shows the GVS isotherm plot of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

FIG. 24 shows the GVS isotherm plot of crystalline mesylate Form 4 of N-hydroxy 2-{6-[(6-fluoro-quinolin-2-ylmethyl)-amino]-3-aza-bicyclo[3.1.0]hex-3-yl}pyrimidine-5-carboxamide.

Example 7—Characterization of Crystalline Mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 5 was obtained during an attempted preparation of Mesylate Form 2, from a solution in THF/water (9:1 v/v). Mesylate Form 5 was also observed when Mesylate Form 3 was held at 40° C./75% RH for 1 week. The characterization of mesylate Form 5 is shown below.

TABLE 15

Characterization of Mesylate Form 5

| | |
|---|---|
| Solvent | 10% H₂O/THF |
| XRPD | Mesylate Form 5 |
| ¹H-NMR | Consistent with structure Mesylate present (~0.9 mol. eq. overlapping peaks with API CH₂) No THF signal detected |
| HPLC Purity | 99.4% |
| DSC | Small endotherm onset 28.4° C. (6 J/g), broad endotherm onset 56.8° C. (52 J/g) Endotherm, onset 152.3° C. (6 J/g) followed by exotherm, onset 163.3° C. (14 J/g) |
| TGA | 5.9% mass loss ambient - 130° C. further mass loss > 195° C. |
| 40° C./75% RH | Unchanged: Mesylate Form 5, 99.5% purity |
| 25° C./97% RH | Unchanged: Mesylate Form 5, 99.5% purity |
| KF | 5.6% water (1.6 mol. eq.) |
| IC* | 21.8% mesylate (1.1 mol. eq) |
| GVS | 4.7% reversible water uptake from 0-90% RH. Hysteresis observed 60-30% RH XRPD Post-GVS: Mesylate Form 5 |
| SEM | Agglomerates comprised of irregular particles and laths (~100 μm in size). Primary particle size ≤10 μm |
| PLM | Large agglomerates present (~300 μm). Smaller particles not easily seen |
| Assignment | Sesquihydrate |

The ¹H NMR was consistent with the structure with ~0.9 mol. eq. mesylate present and no residual THF signal was detected. The sample was recovered in good purity at 99.4% by HPLC. The TGA thermogram had a two-step mass loss of 5.9% which was suspected to be water. Karl Fisher analysis confirmed there to be 5.6% water content (equating to 1.6 mo. eq. water). The DSC had a small endotherm with an onset at 28.4° C. followed by a broad endotherm with onset at 56.8° C. These two endotherms overlapped well with the two-step mass loss. These were followed by an endotherm with onset at 152.3° C. and a subsequent exotherm with onset at 163.3° C. The GVS analysis indicated Mesylate Form 5 to be hygroscopic with 4.7% reversible water uptake from 0-90% RH. From the GVS isotherm and kinetic plots it appears that the form is quite stable with no indication the bound water was lost. This was corroborated with the XRPD post-GVS analysis which was unchanged as Mesylate Form 5. The microscopy analysis shows the presence of agglomerates ~100 μm in size, comprised of irregular particles and laths, with a primary particle size 10 μm. When placed under static storage conditions for 1 week, Mesylate Form 5 was unchanged by XRPD at both 25° C./97% RH and 40° C./75% RH.

In summary, Mesylate Form 5 has been identified as a stable sesquihydrate (q.5 mol. eq. water) of the monomesylate salt that is hygroscopic, as determined by GVS. The form showed short-term solid form stability, remaining unchanged by XRPD after GVS and static storage at elevated conditions up to 1 week.

Example 7a—XRPD Characterization of Crystalline Mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide The peak table and XRPD for Mesylate Form 5 can be found below (Table 16, FIG. 25). The values for 2Θ are considered to have an error of ±0.3 degrees.

TABLE 16

XRPD peak table for Mesylate Form 5

| Angle (°2θ) | Intensity % | Angle (°2θ) | Intensity % |
|---|---|---|---|
| 7.8 | 7.0 | 26.4 | 16.2 |
| 11.5 | 3.3 | 26.9 | 25.4 |
| 11.7 | 4.6 | 27.4 | 44.0 |
| 12.0 | 21.7 | 28.1 | 16.4 |
| 14.1 | 12.7 | 28.6 | 8.5 |
| 14.6 | 12.0 | 29.0 | 11.2 |
| 15.7 | 63.7 | 29.9 | 12.4 |
| 16.1 | 7.5 | 30.5 | 9.1 |
| 16.8 | 83.7 | 30.9 | 24.1 |
| 17.5 | 5.6 | 31.7 | 7.9 |
| 18.0 | 72.1 | 32.0 | 6.0 |
| 19.2 | 5.4 | 32.5 | 8.9 |
| 20.2 | 16.5 | 32.9 | 10.7 |
| 20.4 | 19.9 | 33.1 | 7.9 |
| 20.7 | 100.0 | 33.9 | 30.1 |

TABLE 16-continued

XRPD peak table for Mesylate Form 5

| Angle (°2θ) | Intensity % | Angle (°2θ) | Intensity % |
|---|---|---|---|
| 21.1 | 33.2 | 34.2 | 27.4 |
| 21.5 | 33.8 | 34.6 | 36.8 |
| 22.5 | 31.8 | 35.2 | 12.4 |
| 23.2 | 21.8 | 35.6 | 12.4 |
| 23.6 | 22.3 | 36.7 | 30.0 |
| 24.0 | 9.1 | 38.1 | 10.6 |
| 24.3 | 31.8 | 39.0 | 10.1 |
| 24.9 | 19.3 | 39.3 | 8.4 |
| 25.2 | 21.2 | 40.3 | 10.7 |
| 25.5 | 11.5 | 40.9 | 22.1 |

FIG. 25 shows the XRPD of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

FIG. 26 shows the TGA and DSC of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

Figure 27:
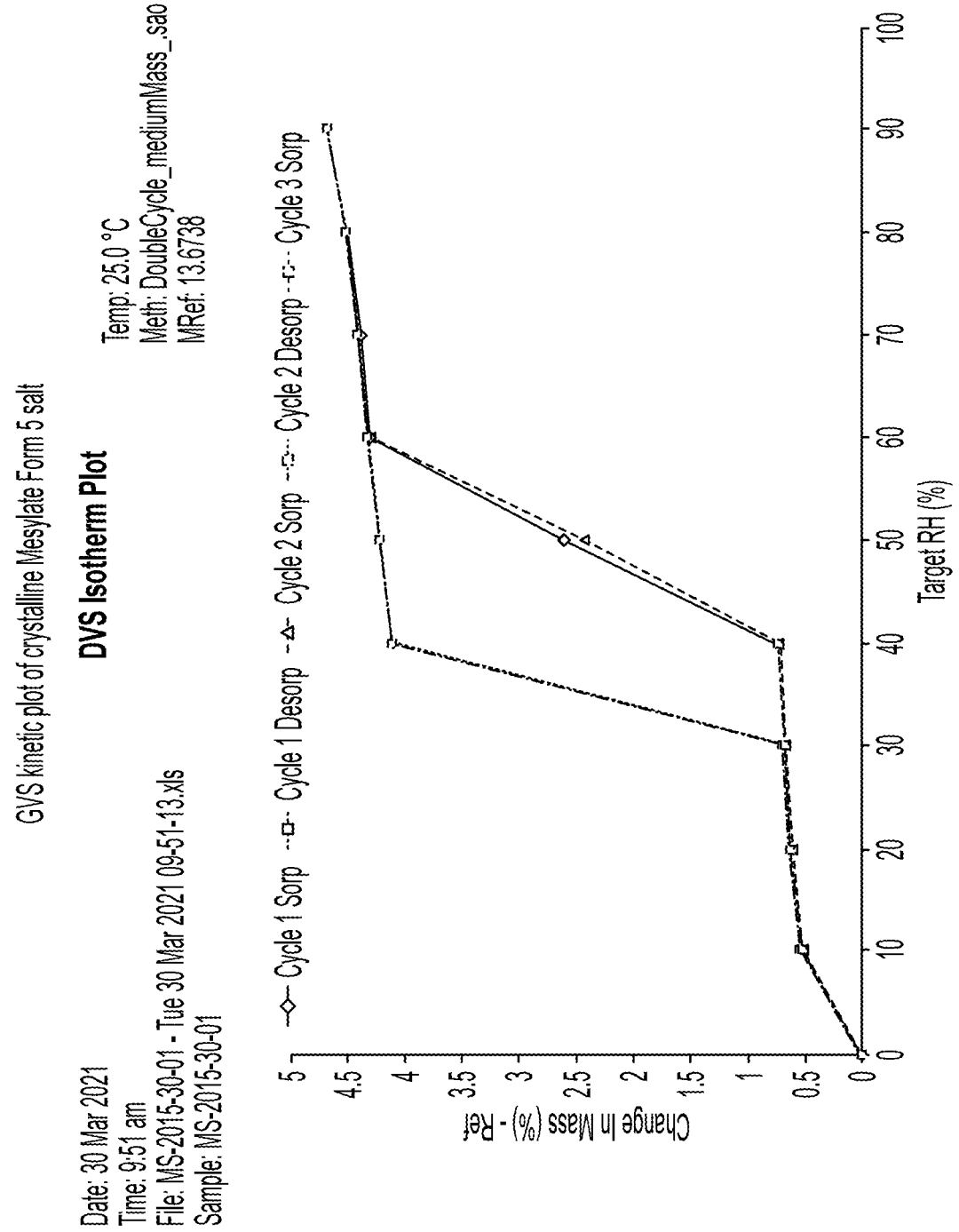
FIG. 27 shows the GVS kinetic plot of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

FIG. 27 shows the GVS kinetic plot of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

Figure 28:
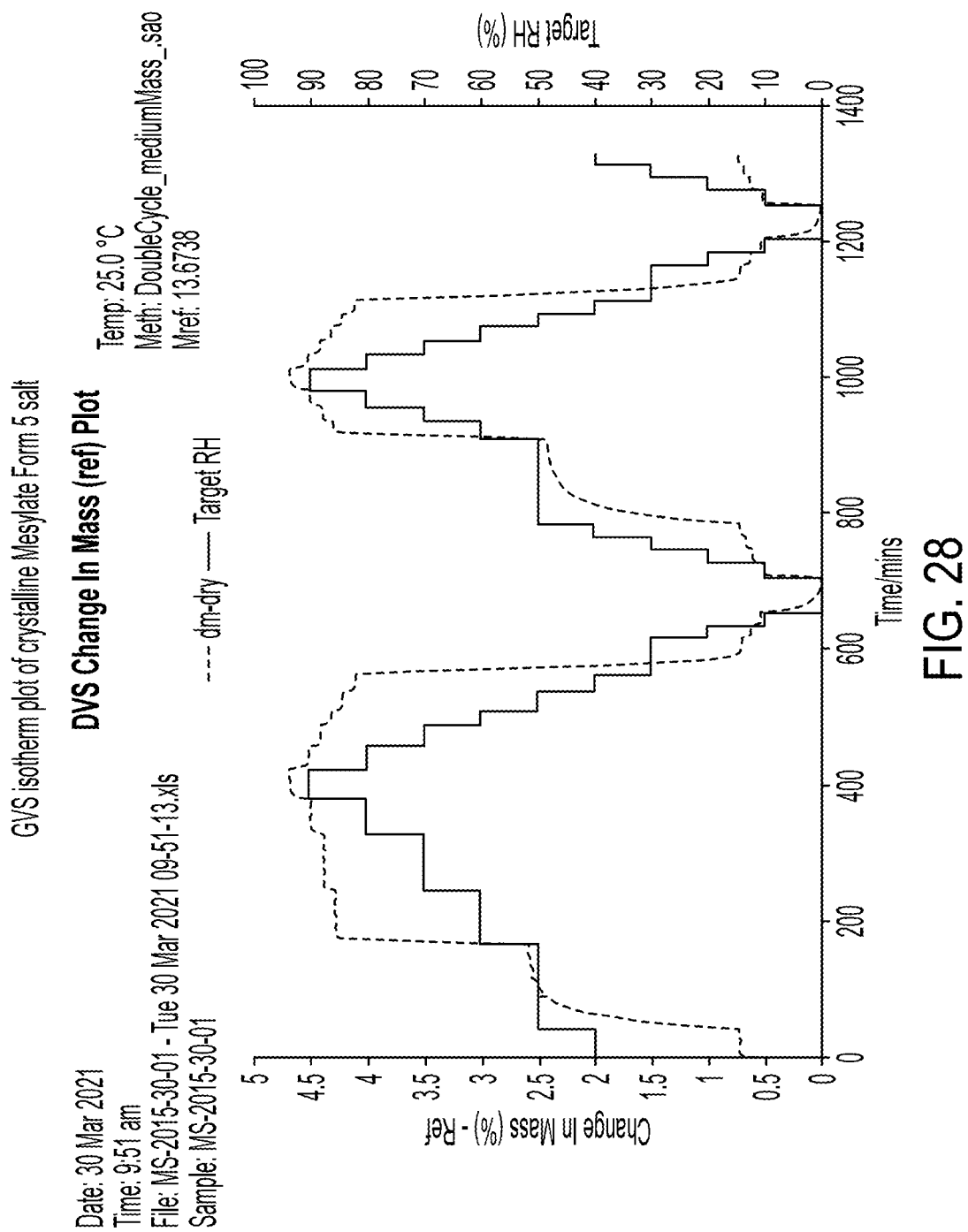
FIG. 28 shows the GVS isotherm plot of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

FIG. 28 shows the GVS isotherm plot of crystalline mesylate Form 5 of N-hydroxy 2-{6-[(6-fluoro-quinolin-2-ylmethyl)-amino]-3-aza-bicyclo[3.1.0]hex-3-yl}pyrimidine-5-carboxamide.

Example 8—Characterization of Crystalline Mesylate Form 6 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 6 was obtained from cooling a turbid solution in DMF to 5° C. The characterization data is summarized in Table 17. The $^1$H NMR showed 0.7 mol. eq. DMF ~0.8 mol. eq. mesylate present in the solid. The TGA had 9.0% mass loss that matched the DMF content by NMR. A small endotherm was observed with onset at 51.1° C. by DSC, followed by a broad endotherm at 84.7° C., which corresponded to the mass loss observed by TGA. An additional, smaller endotherm was observed at 124.7° C. The form converted to Mesylate Form 1 after 1 week at both 40° C./75% RH and 25° C./97% RH. Mesylate Form 6 was tentatively assigned as a DMF solvate that can desolvate under certain conditions.

TABLE 17

Characterization of Mesylate Form 6

| | |
|---|---|
| Solvent | DMF |
| XRPD | Crystalline, mesylate Form 6 |
| $^1$H-NMR | Consistent with proposed structure, shifted peaks. 0.7 mol. eq. DMF, 1.5 mol. eq mesylate |
| DSC | Small endothermic event, onset 51.1° C. (0.2 J/g), broad endotherm onset 84.7° C. (79.8 J/g), corresponding with mass loss. Small endotherm onset 124.7° C. (0.7 J/g) |
| TGA | 9.0% mass loss ~78-113° C., additional mass loss observed >215° C. |
| 40° C./75% RH | Mesylate Form 1 |
| 25° C./97% RH | Mesylate Form 1 |
| Tentative assignment | DMF solvate |

Example 8a—XRPD Characterization of Crystalline Mesylate Form 6 of N-hydroxy 2-{6-[(6-fluoro-quinolin-2-ylmethyl)-amino]-3-aza-bicyclo[3.1.0]hex-3-yl}pyrimidine-5-carboxamide The peak table for Mesylate Form 6 and XRPD for the sample can be found below (Table 18, FIG. 29). The values for 2θ are considered to have an error of 1.3 degrees.

TABLE 18

XRPD peak table for Mesylate Form 6

| Angle (°2θ) | Intensity % | Angle (°2θ) | Intensity % |
|---|---|---|---|
| 4.3 | 22.4 | 20.3 | 18.1 |
| 6.7 | 35.3 | 20.7 | 32.8 |
| 8.7 | 19.7 | 21.3 | 15.8 |
| 10.4 | 19.7 | 21.7 | 12.4 |
| 12.5 | 14.9 | 22.4 | 13.3 |
| 12.9 | 14.6 | 22.9 | 100.0 |
| 13.6 | 18.9 | 23.5 | 21.0 |
| 14.0 | 16.3 | 25.2 | 19.2 |
| 15.7 | 26.6 | 25.4 | 22.6 |
| 16.2 | 43.7 | 25.7 | 21.0 |
| 17.2 | 25.1 | 25.9 | 27.6 |
| 18.9 | 18.8 | 27.4 | 20.8 |
| 19.5 | 14.4 | 27.8 | 15.4 |
| 20.1 | 12.9 | | |

FIG. 29 shows the X-ray powder diffractogram of crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 30 shows the TGA and DSC pattern of crystalline mesylate Form 6 salt of N-hydroxy 2-{6-[(6-fluoro-quinolin-2-ylmethyl)-amino]-3-aza-bicyclo[3.1.0]hex-3-yl}pyrimidine-5-carboxamide.

Example 9—Characterization of Crystalline Mesylate Form 7 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 7 was obtained from cooling a solution in NMP to 5° C. The characterization of Mesylate Form 7 is shown in Table 19. $^1$H NMR analysis showed 1 mol. eq. NMP and a lower 0.7 mol. eq. mesylate present. Due to insufficient sample remaining, thermal analysis was not possible. Mesylate Form 7 converted to Mesylate Form 1 after 1 week storage at 40° C./75% RH and 25° C./97% RH. Mesylate Form 7 was tentatively assigned as an NMP solvate.

TABLE 19

Characterization of Mesylate Form 7

| | |
|---|---|
| Solvent | NMP |
| XRPD | Crystalline, mesylate Form 7 |
| $^1$H-NMR | 1 mol. eq. NMP, 0.7 mol. eq. mesylate |
| DSC | Insufficient sample for analysis |
| TGA | Insufficient sample for analysis |
| 40° C./75% RH | Mesylate Form 1 |
| 25° C./97% RH | Mesylate Form 1 |
| Tentative assignment | NMP solvate |

Example 9a—XRPD Characterization of Crystalline Mesylate Form 7 of N-hydroxy 2-{6-[(6-fluoro-quinolin-2-ylmethyl)-amino]-3-aza-bicyclo[3.1.0]hex-3-yl}pyrimidine-5-carboxamide The peak table for Mesylate Form 7 and XRPD for the sample can be found below (Table 20, FIG. 31). The values for 2θ are considered to have an error of 1.3 degrees.

TABLE 20

XRPD peak table for Mesylate Form 7

| Angle (°2θ) | Intensity % | Angle (°2θ) | Intensity % |
|---|---|---|---|
| 4.2 | 9.7 | 20.2 | 22.5 |
| 6.7 | 27.6 | 20.6 | 56.6 |
| 8.4 | 15.1 | 21.0 | 13.6 |
| 10.4 | 22.2 | 21.4 | 31.8 |
| 12.5 | 16.0 | 21.8 | 9.8 |
| 13.7 | 13.6 | 22.3 | 13.3 |
| 15.6 | 50.3 | 22.9 | 91.9 |
| 16.3 | 100.0 | 23.3 | 29.2 |
| 16.7 | 16.8 | 23.9 | 12.0 |
| 16.9 | 14.9 | 24.5 | 11.7 |
| 17.6 | 11.1 | 25.2 | 20.6 |
| 17.8 | 9.2 | 25.6 | 15.2 |
| 18.4 | 10.0 | 26.1 | 14.2 |
| 18.9 | 11.0 | 26.6 | 18.7 |
| 19.5 | 11.6 | 27.7 | 25.7 |

FIG. 31 shows the X-ray powder diffractogram of crystalline mesylate Form 7 salt of N-hydroxy 2-{6-[(6-fluoro-quinolin-2-ylmethyl)-amino]-3-aza-bicyclo[3.1.0]hex-3-yl}pyrimidine-5-carboxamide.

Example 10—Characterization of Crystalline Mesylate Form 8 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 8 was obtained following maturation temperature cycling (RT/50° C.) of the amorphous salt in DMF. The characterization results are shown in Table 21. The ¹H NMR analysis showed approximately 0.9 mol. eq. DMF ad ~0.9 mol. eq. mesylate. The TGA had a 12.2% mass loss 98-134° C. that was in close agreement with the DMF content. The DSC showed an overlapping broad and a sharp endotherm, the latter with onset at 98.8° C. After static storage of the form converted to Mesylate Form 1 after 1 week at 40° C./75% RH and 25° C./97% RH. Mesylate Form 8 was tentatively assigned as another DMF solvate.

TABLE 21

| Characterization of Mesylate Form 8 | |
|---|---|
| Solvent | DMF |
| XRPD | Crystalline, Mesylate Form 8 |
| ¹H-NMR | ~0.9 mol. eq. DMF, ~0.9 mol. eq. mesylate |
| DSC | Broad endothermic event overlapping with very sharp endotherm, onset 98.8° C. (108 J/g) |
| TGA | 12.2% mass loss 98-134° C. (0.75 mol. eq. DMF) |
| 40° C./75% RH | Mesylate Form 1 |
| 25° C./97% RH | Mesylate Form 1 |
| Tentative assignment | DMF solvate |

Example 10a—XRPD Characterization of Crystalline Mesylate Form 8 of N-hydroxy 2-{6-[(6-fluoro-quinolin-2-ylmethyl)-amino]-3-aza-bicyclo[3.1.0]hex-3-yl}pyrimidine-5-carboxamide The peak table for Mesylate Form 8 and XRPD for the sample can be found below (Table 22, FIG. 32). The values for 2θ are considered to have an error of ±0.3 degrees.

TABLE 22

XRPD peak table for Mesylate Form 8

| Angle (°2θ) | Intensity % | Angle (°2θ) | Intensity % |
|---|---|---|---|
| 4.4 | 100.0 | 18.2 | 23.1 |
| 6.8 | 61.4 | 19.0 | 11.7 |
| 8.7 | 51.2 | 20.4 | 24.0 |
| 10.2 | 16.0 | 20.8 | 19.9 |
| 10.4 | 13.1 | 21.4 | 17.7 |
| 13.1 | 19.2 | 21.8 | 7.5 |
| 13.6 | 9.0 | 22.5 | 14.8 |
| 14.1 | 43.4 | 23.0 | 12.4 |
| 15.7 | 9.0 | 26.3 | 14.4 |
| 16.2 | 57.0 | 26.8 | 13.3 |
| 17.3 | 18.0 | 27.5 | 12.7 |

FIG. 32 shows the X-ray powder diffractogram of crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 33 shows the TGA and DSC pattern of crystalline mesylate Form 8 salt of N-hydroxy 2-{6-[(6-fluoro-quinolin-2-ylmethyl)-amino]-3-aza-bicyclo[3.1.0]hex-3-yl}pyrimidine-5-carboxamide.

Example 11—Characterization of Crystalline Mesylate Form 9 of N-hydroxy 2-{6-[(6-fluoro-quinolin-2-ylmethyl)-amino]-3-aza-bicyclo[3.1.0]hex-3-yl}pyrimidine-5-carboxamide Mesylate Form 1 was dissolved in DMSO/acetone (1:1 v/v) (35 ml, 35 volumes) at 50° C. with stirring to produce a clear, yellow solution. The sample was stirred for 1 hour further at 50° C. before cooling to 5° C. at 0.5° C./minute and was stirred at 5° C. overnight. The resulting white suspension was filtered over a Buchner funnel and dried for ca. 15 minutes. A small sample was taken and analyzed by XRPD. The solid was isolated in 57% yield, and was further characterized by ¹H NMR, TGA, DSC and KF and stored under elevated static conditions.

XRPD confirmed the isolation of Mesylate Form 9. The ¹H NMR showed the sample to contain 2.9 mol. eq. DMSO, with residual acetone also present (<0.01 mol. eq.). The TGA thermogram showed a large mass loss, of 41.2%, corresponding to 4.3 mol. eq. DMSO. Karl Fisher indicated there was 4.8% water content. The higher DMSO content in this sample in addition to water content may be due to insufficient drying of the sample at scale. The DSC thermogram had a broad endotherm at 78.2° C. (which may have possible overlapping events), overlapped with the mass loss observed by TGA. Mesylate Form 9 converted under storage at both 40° C./75% RH and 25° C./97% RH to Mesylate Form 1, with the sample stored at 40° C./75%0 RH showing a color change to yellow. The analysis indicated to Mesylate Form 9 being a DMSO solvate and with a more appropriate drying protocol, the DMSO content is likely lower similar to the screening sample.

TABLE 23

Characterization of Mesylate Form 9

| | | |
|---|---|---|
| Solvent | | DMSO/Acetone 1:1 |
| XRPD | | Crystalline, matches Mesylate Form 9 |
| $^1$H-NMR | | 2.9 mol. eq. DMSO; residual Acetone (<0.01 mol. eq.), sample likely remains wet due to insufficient drying |
| Thermal Analysis | TGA | 41.2% mass loss observed ambient - 247° C. (4.3 mol. eq. DMSO), continued mass loss up to 350° C. Additional; mass loss likely due to insufficient drying. |
| | DSC | Broad endotherm observed at 78.2° C., (poss. overlapping events, 57.1 J/g), corresponding to mass loss. Additional events >173° C., likely corresponding to degradation. |
| | KF | 4.8% water present (1.4 mol. eq.) Color change of solid observed from white to light brown |
| Static Storage/ 1 week | 40° C./ 75% RH | Sample appeared 'damp' - yellow solid present Mesylate Form 1 |
| | 25° C./ 97% RH | Sample appeared wet - white solid still present Poorly crystalline - Mesylate Form 1 |

Example 11a—XRPD Characterization of Crystalline Mesylate Form 9 of N-hydroxy 2-{6-[(6-fluoro-quinolin-2-ylmethyl)-amino]-3-aza-bicyclo[3.1.0]hex-3-yl}pyrimidine-5-carboxamide The peak table for Mesylate Form 9 and XRPD for the sample can be found below (Table 24, FIG. 34). The values for 2θ are considered to have an error of 1.3 degrees.

TABLE 24

XRPD peak table for Mesylate Form 9

| Angle (°2θ) | Intensity % | Angle (°2θ) | Intensity % |
|---|---|---|---|
| 4.2 | 52.5 | 22.7 | 5.7 |
| 8.4 | 42.6 | 23.1 | 6.4 |
| 8.6 | 22.8 | 23.6 | 11.5 |
| 11.3 | 7.7 | 23.8 | 9.6 |
| 14.7 | 14.7 | 24.1 | 18.7 |
| 15.0 | 25.4 | 24.8 | 6.3 |
| 16.9 | 13.0 | 25.6 | 4.5 |
| 17.2 | 100.0 | 25.9 | 6.5 |
| 18.5 | 13.5 | 26.1 | 4.3 |
| 19.7 | 5.6 | 26.3 | 4.5 |
| 19.9 | 5.9 | 26.7 | 2.7 |
| 20.9 | 9.3 | 28.0 | 4.6 |
| 22.2 | 18.1 | 28.3 | 6.1 |
| 22.5 | 9.1 | | |

FIG. 34 shows the X-ray powder diffractogram of crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide.

FIG. 35 shows the TGA and DSC pattern of crystalline mesylate Form 9 salt of N-hydroxy 2-{6-[(6-fluoro-quinolin-2-ylmethyl)-amino]-3-aza-bicyclo[3.1.0]hex-3-yl}pyrimidine-5-carboxamide.

Example 12—Comparative studies between crystalline mesylate forms of N-hydroxy 2-{6-[(6-fluoro-quinolin-2-ylmethyl)-amino]-3-aza-bicyclo[3.1.0]hex-3-yl}pyrimidine-5-carboxamide The polymorph studies of the mesylate salts of compound 1 yielded 10 forms: an amorphous form, an anhydrate (Form 1) 4 hydrates (Forms 2-5), 2 DMF solvates (Forms 6 and 8), an NMP solvate (Form 7), and a DMSO solvate (Form 9). The solvates were unstable, converting to Form 1 at 25° C./97% RH and 40° C./75% RH.

Form 2 was characterizes as a monohydrate, a slightly hygroscopic form that was stable after 1 week at elevated conditions. A metastable nonahydrate (Form 3) was identified and was unstable to drying (losing significant crystallinity) and would convert to Mesylate Form 5 at 40° C./75% RH (and remained as Mesylate Form 3 at 25° C./97% RH). Mesylate Form 4 was a metastable trihydrate that converted to Mesylate Form 1 at 25° C./97% RH and was a mixture of Mesylate Form 1 and Form 4 after 1 week at 40° C./75% RH. A fourth hydrate was then identified and isolated during an initial attempt to prepare the monohydrate. This new hydrate, Mesylate Form 5 was a hygroscopic sesquihydrate that was stable after GVS analysis and remained as Mesylate Form 5 after 1 week at the elevated temperature/humidity conditions.

The thermodynamic solubility of the anhydrous Mesylate Form 1 and four hydrates was measured in FaSSIF, FeSSIF and FaSSGF media. The anhydrous Form 1 typically displayed the highest solubility (1.90 mg/ml—FaSSIF; 0.34—FeSSIF; 21.0 mg/ml FaSSGF) of the forms except Form 4 (trihydrate) which had slightly higher solubility in FaSSGF (24.0 mg/ml). The solubility residues in most cases showed disproportionation of the salt to FreeForm A, although two new solubility residue patterns were identified in FaSSGF from Mesylate Form 3 and Form 5, respectively. There was insufficient residue to characterize these further.

Competitive slurries of the anhydrous and hydrated forms in different water activity at 50° C. and 5° C. were used to determine the thermodynamic stability relationships. Mesylate Form 1 was the most stable up to aw=0.6 at 50° C. and up to at least aw=0.3 at 5° C. Based on the solid form properties, thermodynamic aqueous solubility and understanding of the thermodynamic stability relationships between these forms it was recommended to proceed to initial crystallization development of the anhydrous Mesylate Form 1.

We claim:

1. A method of treating a condition in which HDAC has demonstrated a role in epigenetic regulation and pathology in an individual, the method comprising administering an effective amount of:
   (a) valganciclovir; and
   (b) Crystalline mesylate Form 1 salt of N-hydroxy 2-{6-[(6-fluoro-quinolin-2-ylmethyl)-amino]-3-aza-bicyclo[3.1.0]hex-3-yl}pyrimidine-5-carboxamide characterized by at least three X-ray diffraction pattern reflections selected from a 2 theta value of 3.7°0.3, 7.5°±0.3, 14.9°±0.3, 17.3°±0.3, 19.7°±0.3, 22.5°±0.3, 22.9°±0.3, or 30.1°±0.3
   thereby treating the condition in the individual.

2. The method of claim 1, wherein the condition is inflammation, an immune disorder, or cancer.

3. The method of claim 2, wherein the condition is cancer.

4. The method of claim 1, wherein the amount of another crystalline form is 5% (w/w) or less.

5. The method of claim 1, wherein the amount of an amorphous form is 5% (w/w) or less.

6. The method of claim 1, wherein the amount of impurities is 3% or less.

7. A method of treating a condition in which HDAC has demonstrated a role in epigenetic regulation and pathology in an individual, the method comprising administering an effective amount of:

(a) valganciclovir; and (b) Crystalline mesylate Form 1 salt of N-hydroxy 2-{6-[(6-fluoro-quinolin-2-ylmethyl)-amino]-3-aza-bicyclo [3.1.0]hex-3-yl}pyrimidine-5-carboxamide characterized by at least five X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, or 30.1°±0.3 thereby treating the condition in the individual.

8. The method of claim 7, wherein the condition is inflammation, an immune disorder, or cancer.

9. The method of claim 8, wherein the condition is cancer.

10. The method of claim 7, wherein the amount of another crystalline form is 5% (w/w) or less.

11. The method of claim 7, wherein the amount of an amorphous form is 5% (w/w) or 12 less.

12. The method of claim 7, wherein the amount of impurities is 3% or less.

13. A method of treating a condition in which HDAC has demonstrated a role in epigenetic regulation and pathology in an individual, the method comprising administering an effective amount of:

(a) valganciclovir; and (b) Crystalline mesylate Form 1 salt of N-hydroxy 2-{6-[(6-fluoro-quinolin-2-ylmethyl)-amino]-3-aza-bicyclo [3.1.0]hex-3-yl}pyrimidine-5-carboxamide, characterized by:
  (i) at least two X-ray diffraction pattern reflections selected from a 2 theta value of 3.7°±0.3, 7.5°±0.3, 14.9°±0.3, 17.3°±0.3, 19.7°±0.3, 22.5°±0.3, 22.9°±0.3, or 30.1°±0.3; and
  (ii) differential scanning calorimetry (DSC), wherein the DSC thermogram exhibits a single exothermic event with an onset temperature at about 222.1° C.±5.0 (433 J/g) or an exothermic peak at 225.8° C.±5.0;

thereby treating the condition in the individual.

14. The method of claim 13, wherein the condition is inflammation, an immune disorder, or cancer.

15. The method of claim 14, wherein the condition is cancer.

16. The method of claim 13, wherein the amount of another crystalline form is 5% (w/w) or less.

17. The method of claim 13, wherein the amount of an amorphous form is 5% (w/w) or less.

18. The method of claim 13, wherein the amount of impurities is 3% or less.

* * * * *

UNITED STATES PATENT AND TRADEMARK OFFICE
CERTIFICATE OF CORRECTION

PATENT NO. : 12,012,396 B2
APPLICATION NO. : 18/364074
DATED : June 18, 2024
INVENTOR(S) : Xiaohu Deng et al.

It is certified that error appears in the above-identified patent and that said Letters Patent is hereby corrected as shown below:

In the Claims

In Claim 11, Column 53, at Line 19, replace:
"5% (w/w) or 12 less."
With:
-- 5% (w/w) or less. --

Signed and Sealed this
Seventeenth Day of September, 2024

Katherine Kelly Vidal
*Director of the United States Patent and Trademark Office*